(12) United States Patent
Chen et al.

(10) Patent No.: US 7,649,010 B2
(45) Date of Patent: Jan. 19, 2010

(54) CARVEDILOL HYDROBROMIDE

(75) Inventors: Pingyun Y. Chen, Research Triangle Park, NC (US); Qunying Dai, King Of Prussia, PA (US); Philip C. Dell'Orco, King Of Prussia, PA (US); Claire Hisler, Meyzieu (FR); David H. Igo, Research Traingle Park, NC (US); Lee M. Katrincic, King Of Prussia, PA (US); Clifford S. Labaw, King Of Prussia, PA (US); Li-Jen J. Ping, King of Prussia, PA (US)

(73) Assignee: SmithKline Beechman Cork Limited, Currabinny, Carigaline, County Cork (IE)

( * ) Notice: Subject to any disclaimer, the term of this patent is extended or adjusted under 35 U.S.C. 154(b) by 0 days.

(21) Appl. No.: 11/548,368

(22) Filed: Oct. 11, 2006

(65) Prior Publication Data

US 2007/0142451 A1    Jun. 21, 2007

Related U.S. Application Data

(63) Continuation of application No. 10/518,206, filed as application No. PCT/US03/20346 on Jun. 27, 2003, now abandoned.

(60) Provisional application No. 60/392,374, filed on Jun. 27, 2002.

(51) Int. Cl.
  *A61K 31/403* (2006.01)
  *C07D 209/82* (2006.01)
(52) U.S. Cl. ............. 514/411; 548/440; 548/444
(58) Field of Classification Search ............ 514/411; 548/444, 440
  See application file for complete search history.

(56) References Cited

U.S. PATENT DOCUMENTS

| | | | |
|---|---|---|---|
| 4,503,067 A | 3/1985 | Wiedemann et al. | |
| 4,985,454 A | 1/1991 | Leinert | |
| 5,071,868 A | 12/1991 | Leinert | |
| 5,308,862 A | 5/1994 | Ohlstein | |
| 5,393,772 A | 2/1995 | Yue et al. | |
| 5,405,863 A | 4/1995 | Barone et al. | |
| 5,453,436 A | 9/1995 | Ohlstein | |
| 5,643,939 A | 7/1997 | Ohlstein | |
| 5,760,069 A | 6/1998 | Lukas-Laskey et al. | |
| 5,902,821 A | 5/1999 | Lukas-Laskey et al. | |
| 6,096,777 A | 8/2000 | Fcucrstcin et al. | |
| 6,214,854 B1 | 4/2001 | Wang et al. | |
| 6,358,990 B1 | 3/2002 | Howlett et al. | |
| 6,403,579 B1 | 6/2002 | Heller | |
| 6,515,010 B1 | 2/2003 | Franchini et al. | |
| 6,699,997 B2 | 3/2004 | Hildesheim et al. | |
| 6,852,337 B2 | 2/2005 | Gabel et al. | |
| 7,056,942 B2 | 6/2006 | Hildesheim et al. | |
| 7,126,008 B2 | 10/2006 | Hildesheim et al. | |
| 2001/0036959 A1 | 11/2001 | Gabel et al. | |
| 2001/0036960 A1 | 11/2001 | Decker et al. | |
| 2002/0052367 A1 | 5/2002 | Heller | |
| 2002/0068740 A1 | 6/2002 | Mylari | |
| 2002/0099013 A1 | 7/2002 | Piccariello et al. | |
| 2002/0099046 A1 | 7/2002 | Scott | |
| 2002/0107279 A1 | 8/2002 | Barone et al. | |
| 2002/0115655 A1 | 8/2002 | Mehanna et al. | |
| 2002/0143045 A1 | 10/2002 | Hildesheim et al. | |
| 2002/0169199 A1 | 11/2002 | Gruber et al. | |
| 2003/0004205 A1 | 1/2003 | Gabel et al. | |
| 2003/0004206 A1 | 1/2003 | Decker et al. | |
| 2003/0035836 A1 | 2/2003 | Shanghvi et al. | |
| 2003/0036559 A1 | 2/2003 | Beyer et al. | |
| 2003/0050301 A1 | 3/2003 | Mylari | |
| 2003/0054041 A1 | 3/2003 | Lemmens et al. | |
| 2003/0166702 A1 | 9/2003 | Kor et al. | |
| 2004/0019096 A1 | 1/2004 | Andronis et al. | |
| 2004/0152756 A1 | 8/2004 | Chen et al. | |
| 2004/0186158 A1 | 9/2004 | Oh | |
| 2004/0220250 A1 | 11/2004 | Oh | |
| 2005/0009897 A1 | 1/2005 | Anderson et al. | |
| 2005/0148779 A1 | 7/2005 | Chen et al. | |
| 2005/0169994 A1 | 8/2005 | Burke et al. | |
| 2007/0238774 A1 | 10/2007 | Brook et al. | |
| 2007/0244181 A1 | 10/2007 | Brook et al. | |
| 2007/0244182 A1 | 10/2007 | Brook et al. | |
| 2007/0259940 A1 | 11/2007 | Brook et al. | |
| 2008/0096951 A1 | 4/2008 | Chen et al. | |
| 2008/0262069 A1 | 10/2008 | Brook et al. | |

FOREIGN PATENT DOCUMENTS

WO    WO98/02157    1/1998

(Continued)

OTHER PUBLICATIONS

Jain et al., Polymorphism in Pharmacy, Indian Drugs, vol. 23 (6), pp. 315-329, 1986.

(Continued)

*Primary Examiner*—Charanjit S Aulakh
(74) *Attorney, Agent, or Firm*—Grace C. Hsu; John Lemanowicz; Charles M. Kinzig

(57) ABSTRACT

The present invention relates to a salt of carvedilol, corresponding compositions containing such a carvedilol salt or corresponding solvates thereof, and/or methods of using the aforementioned compound(s) in the treatment of certain disease states in mammals, in particular man. The present invention further relates to a novel crystalline form of carvedilol hydrobromide, which is the hydrobromide salt of 1-(carbazol-4-yloxy-3-[[2-(o-methoxyphenoxy)ethyl]amino]-2-propanol, and/or other carvedilol solvates thereof, compositions containing salts or solvates of carvedilol hydrobromide, and methods of using the aforementioned compound(s) to treat hypertension, congestive heart failure, and angina, etc.

30 Claims, 82 Drawing Sheets

FOREIGN PATENT DOCUMENTS

| WO | WO99/05105 | 2/1999 |
|----|------------|--------|
| WO | WO99/52526 | 10/1999 |
| WO | WO00/04902 | 2/2000 |
| WO | WO00/32174 | 6/2000 |
| WO | WO01/74356 | 10/2001 |
| WO | WO01/87837 | 11/2001 |
| WO | WO02/00216 | 1/2002 |
| WO | WO02/092078 | 11/2002 |
| WO | WO03/007962 | 1/2003 |
| WO | WO03/024426 | 3/2003 |
| WO | WO03/024429 | 3/2003 |
| WO | WO03/028645 | 4/2003 |
| WO | WO03/028718 | 4/2003 |
| WO | WO2004/009120 | 1/2004 |
| WO | WO2004/014304 | 2/2004 |
| WO | WO2004/016249 | 2/2004 |
| WO | WO2004/041252 | 5/2004 |
| WO | WO2004/056336 | 7/2004 |

OTHER PUBLICATIONS

Rouhi et al., The Right Stuff—From Research and Development to the Clinic, Getting Drug Crystals Right is Full of Pitfalls, Science and Technology, Chemical & Engineering News, pp. 32-35, Feb. 24, 2003.

U.S. Appl. No. 10/513,234, filed May 3, 2002, Oh, PCT/US03/14021 Filed: May 3, 2002, WO03/092626 Pub. Date: Nov. 13, 2003.

U.S. Appl. No. 10/513,235, filed Nov. 2, 2004, Oh et al., PCT/US03/14020 Filed: May 3, 2002, WO03/092626 Pub. Date: Nov. 13, 2003.

U.S. Appl. No. 10/518,206, filed Dec. 16, 2004, Chen et al., PCT/US03/20346 Filed: Jun. 27, 2002, WO04/002472 Pub. Date: Jan. 8, 2004.

U.S. Appl. No. 10/997,230, filed Nov. 24, 2004, Brook et al., PCT/US04/039528 Filed: Nov. 24, 2004, WO05/051383 Pub. Date: Jun. 9, 2005.

PCT/US04/039614 Filed: Nov. 24, 2004, Pub. Date: Aug. 11, 2005, Castan et al., WO05/051322 Pub. Date: Jun. 9, 2005.

U.S. Appl. No. 11/137,261, filed May 25, 2005, Burke et al., CIP U.S. Appl. No. 10/996,904, filed Nov. 24, 2004.

Concise Encyclopedia Chemistry, 1994, p. 873.

Phadnis et al., "Identification of Drugs in Pharmaceutical Dosage Forms by X-Ray Powder Diffractometry", J. of Pharm. and Biomed. Analysis, 1997,15, 929-943.

Taday et al., "Using Terahertz Pulse Spectroscopy to Study the Crystalline Structure of a Drug: A Case Study of the Polymorphs of Ranitidine Hydrochloride", J. of Pharm. Sci., 2003, vol. 92, No. 4, 831-838 (2003).

Chakravarty et al., Crystal Forms of Tolbutamide from Acetonitrile and 1-Octanol: Effect of Solvent, Humidity and Compression Pressure, Intern.'l J. of Pharmaceutics, 2005, 288, 335-348.

TransForm Pharmaceuticals, "Carvedilol Phosphate Solid Form Screening, Final Report", Apr. 19, 2004, pp. 1-67.

KSR v. Teleflex, Wikipedia, The Free Encyclopedia, pp. 1-3 (see Footnote 6 at p. 3, lines 14-17)., 2007.

Berge et. al., "Pharmaceutical Salts", J. Pharm. Sciences, 66: 1-19, 1977.

Shanker et al., "Selection of Appropriate Salt Form(s) for New Drug Candidates", Pharm. Res. 11:S-236, 1995.

Bryn et al., "Pharmaceutical Solids: A Strategic Approach to Regulatory Considerations", Pharmaceutical Research (1995), 12 (7), pp. 945-954.

Davies et al., Changing the Salt Form of a Drug Affects Its Clinical Efficacy and Safety, The Pharmaceutical Journal (2001), 266(7), pp. 322-323.

U.S. Office Action of U.S. Appl. No. 11/767,573, Dated: Mar. 31, 2008.

U.S. Office Action of U.S. Appl. No. 11/767,581, Dated: Apr. 10, 2008 (.

U.S. Office Action of U.S. Appl. No. 11/767,586, Dated: Mar. 31, 2008.

U.S. Office Action of U.S. Appl. No. 11/767,566, Dated: Apr. 4, 2008.

U.S. Office Action of U.S. Appl. No. 10/483,217, Dated: Jul. 18, 2006.

U.S. Office Action of U.S. Appl. No. 10/512,628, Dated: Oct. 4, 2007 and Mar. 30, 2007.

U.S. Office Action of U.S. Appl. No. 10/518,206, Dated: Dec. 5, 2005 and Jul. 13, 2006.

U.S.P.T.O. Biotechnology/Chemical/Pharmaceutical Customer Partnership Meeting, Jun. 13, 2006, Slide Lecture on: Polymorphs in Pharmaceutical Products, Presenter: Christopher Low, tQAS, TC1600.

Chemical & Engineering News, Feb. 24, 2003, pp. 32-35.

CARVEDILOL HYDROBROMIDE

CROSS REFERENCE TO PRIOR APPLICATIONS

This application is a continuation of Ser. No. 10/518,206 filed 16 Dec. 2004 now abandoned which is a 371 application of PCT/US2003/020346 filed 27 Jun. 2003 which claims the benefit of U.S. provisional 60/392,374 filed 27 Jun. 2002.

FIELD OF THE INVENTION

The present invention relates to a salt of carvedilol, corresponding compositions containing such a carvedilol salt or corresponding solvates thereof, and/or methods of using the aforementioned compound(s) in the treatment of certain disease states in mammals, in particular man.

The present invention further relates to a novel crystalline form of carvedilol hydrobromide, which is the hydrobromide salt of 1-(carbazol-4-yloxy-3-[[2-(o-methoxyphenoxy)ethyl] amino]-2-propanol, and/or other carvedilol hydrobromide solvates thereof, compositions containing such salts and/or solvates of carvedilol hydrobromide, and methods of using the aforementioned salt(s) and/or solvate(s) to treat hypertension, congestive heart failure, and angina, etc.

BACKGROUND OF THE INVENTION

The compound, 1-(carbazol-4-yloxy-3-[[2-(o-methoxyphenoxy)ethyl]-amino]-2-propanol is known as Carvedilol. Carvedilol is depicted by the following chemical structure:

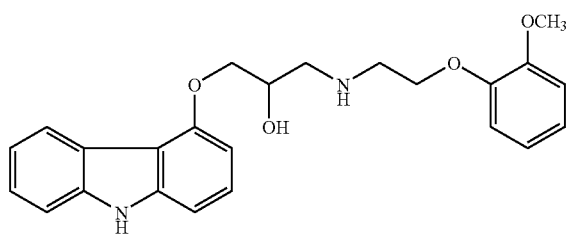

Carvedilol is disclosed in U.S. Pat. No. 4,503,067 to Wiedemann et al. (i.e., assigned to Boehringer Mannheim, GmbH, Mannheim-Waldhof, Fed. Rep. of Germany), which was issued on Mar. 5, 1985.

Currently, Carvedilol is synthesized as free base for incorporation in medication that is available commercially. The aforementioned free base form of Carvedilol is a racemic mixture of R(+) and S(−) enantiomers, where nonselective β-adrenoreceptor blocking activity is exhibited by the S(−) enantiomer and α-adrenergic blocking activity is exhibited by both R(+) and S(−) enantiomers. Those unique features or characteristics associated with such a racemic Carvedilol mixture contributes to two complementary pharmacologic actions: i.e., mixed venous and arterial vasodilation and non-cardioselective, beta-adrenergic blockade.

Carvedilol is used for treatment of hypertension, congestive heart failure and angina. The currently commercially available carvedilol product is a conventional, tablet prescribed as a twice-a-day medication in the United States.

Carvedilol contains an α-hydroxyl secondary amine functional group, which has a pKa of 7.8. Carvedilol exhibits predictable solubility behaviour in neutral or alkaline media, i.e. above a pH of 9.0, the solubility of carvedilol is relatively low (<1 μg/mL). The solubility of carvedilol increases with decreasing pH and reaches a plateau near pH=5, i.e. where saturation solubility is about 23 μg/mL at pH 7 and about 100 μg/mL at pH=5 at room temperature. At lower pH values (i.e., at a pH of 1 to 4 in various buffer systems), solubility of carvedilol is limited by the solubility of its protonated form or its corresponding salt formed in-situ. The hydrochloride salt of carvedilol generated in-situ in an acidic medium, such as in a simulated gastric fluid, is less soluble in such medium than the protonated form of carvedilol.

In light of the foregoing, a salt, and/or novel crystalline form of carvedilol (i.e., such as carvedilol hydrobromide monohydrate, carvedilol hydrobromide anhydrate, and/or other solvates thereof) with greater aqueous solubility, chemical stability, etc. would offer many potential benefits for provision of medicinal products containing the drug carvedilol. Such benefits would include products with the ability to achieve desired or prolonged drug levels in a systemic system by sustaining absorption along the gastrointestinal tract of mammals (i.e., such as humans), particularly in regions of neutral pH, where a drug, such as carvedilol, has minimal solubility.

Surprisingly, it has now been shown that a novel crystalline form of carvedilol hydrobromide salt, can be isolated as a pure, crystalline solid, which exhibits much higher aqueous solubility than the corresponding free base or other prepared crystalline salts of carvedilol, such as the hydrochloride salt. This novel crystalline form also has potential to improve the stability of carvedilol in formulations due to the fact that the secondary amine functional group attached to the carvedilol core structure, a moiety pivotal to degradation processes, is protonated as a salt.

In light of the above, a need exists to develop different carvedilol forms and/or different compositions respectively, which have greater aqueous solubility, chemical stability, sustained or prolonged drug or absorption levels (i.e., such as in neutral gastrointestinal tract pH regions, etc.).

There also exists a need to develop methods of treatment for hypertension, congestive heart failure or angina, etc. which comprises administration of the aforementioned compounds and/or compositions.

The present invention is directed to overcoming these and other problems encountered in the art.

SUMMARY OF THE INVENTION

In general, the present invention relates to a salt of carvedilol, corresponding compositions containing such a carvedilol salt or corresponding solvates thereof, and/or methods of using the aforementioned compound(s) in the treatment of certain disease states in mammals, in particular man.

More specifically, the present invention provides a salt, and/or novel crystalline form of carvedilol hydrobromide (i.e., such as carvedilol hydrobromide monohydrate, carvedilol hydrobromide anhydrate), and/or other solvates thereof.

The present invention further relates to pharmaceutical compositions, which contain the aforementioned salt and/or novel crystalline forms and/or solvates of carvedilol hydrobromide.

The present invention relates to a method of treating hypertension, congestive heart failure or angina, which comprises administering to a subject in need thereof an effective amount of a salt and/or novel crystalline form of carvedilol (i.e., as defined by the aforementioned salts and/or solvates) or a corresponding pharmaceutical composition, which contains such aforementioned salt, and/or novel crystalline forms of carvedilol., etc.

DETAILED DESCRIPTION OF THE INVENTION

Figure 1:
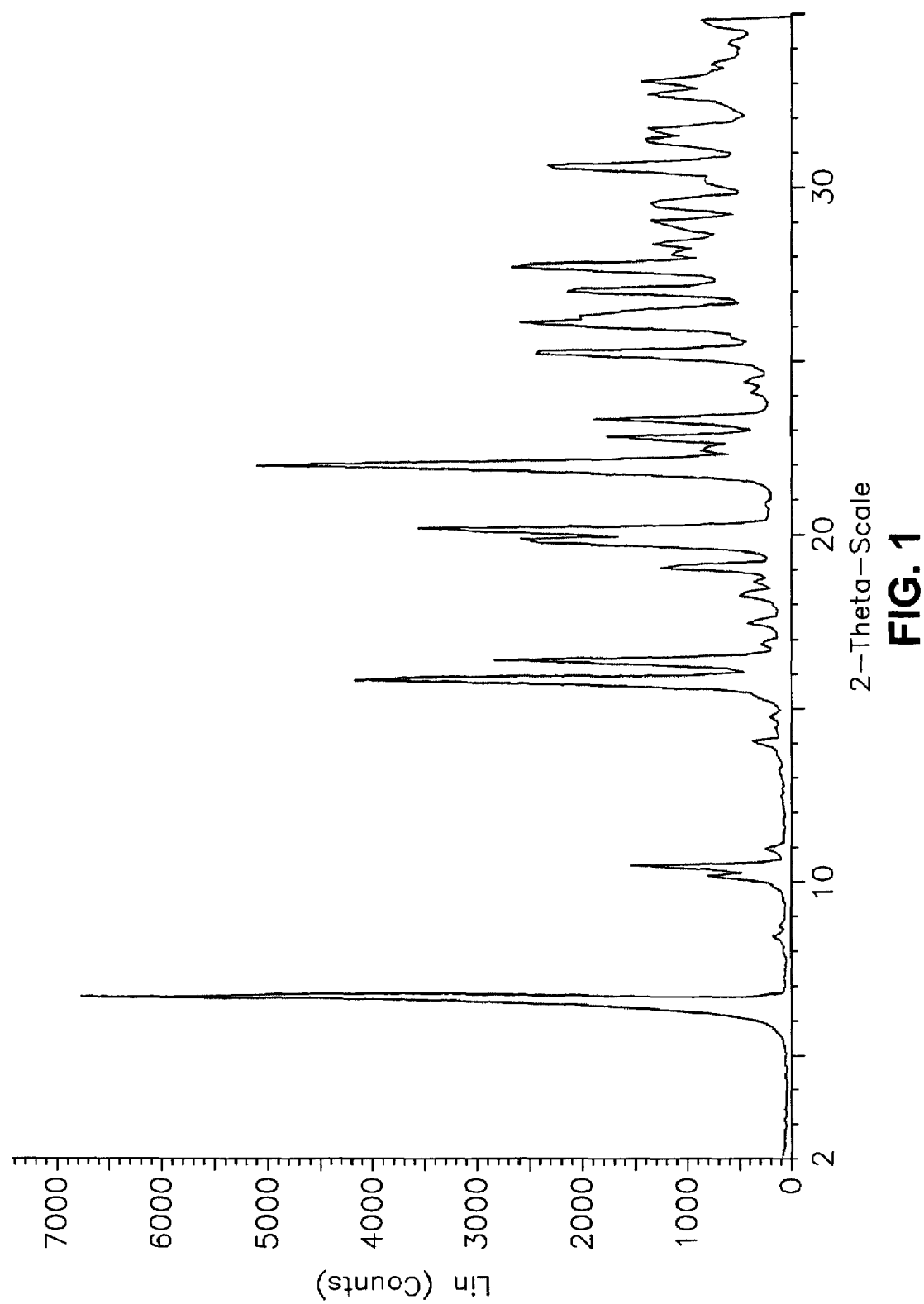
FIG. 1 is an x-ray powder diffractogram for carvedilol hydrobromide monohydrate.
Figure 2:
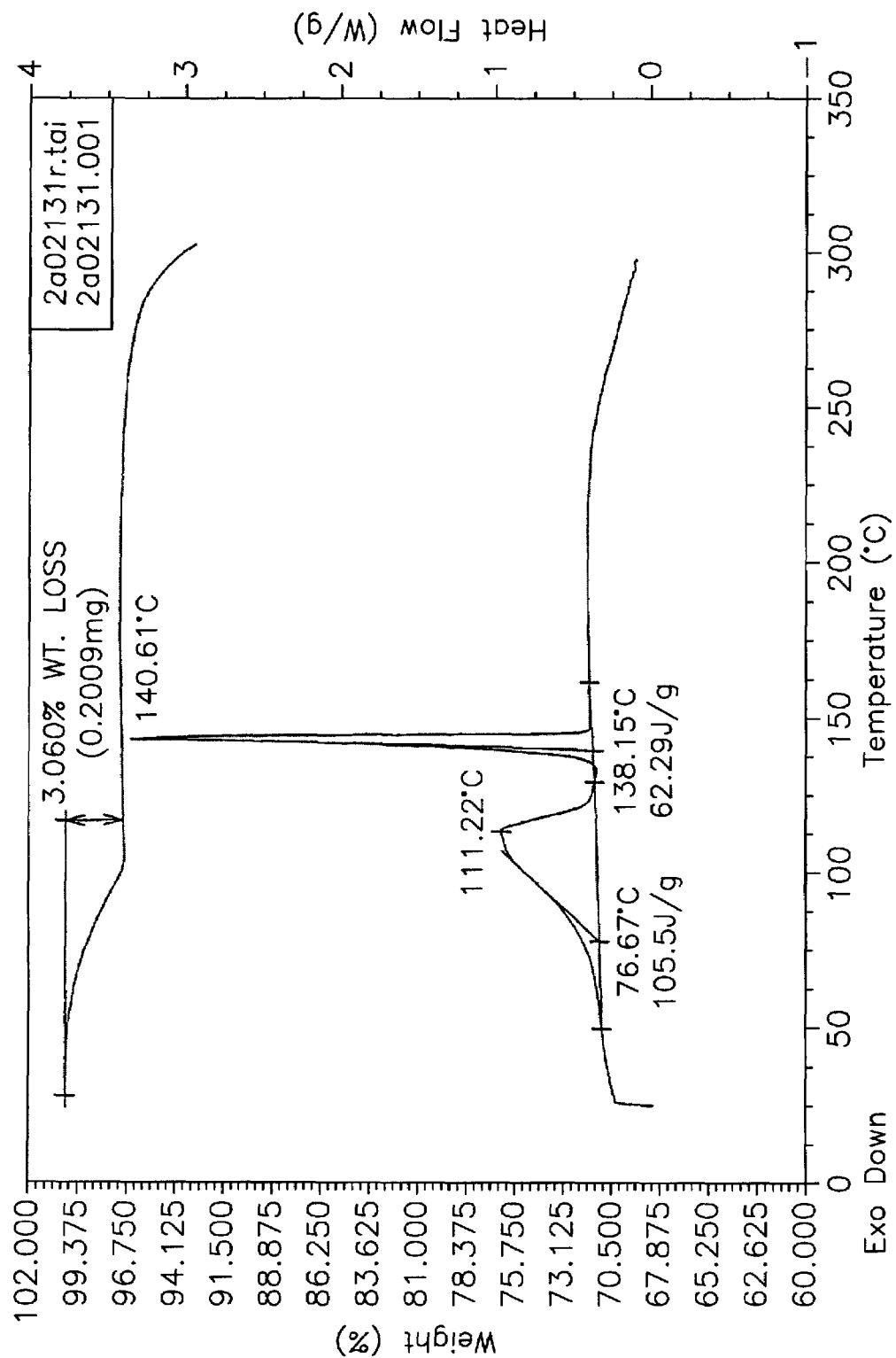
FIG. 2 is a differential scanning calorimetry thermogram for carvedilol hydrobromide monohydrate.

The present invention provides a salt and/or novel crystalline form of carvedilol, i.e., such as carvedilol hydrobromide monohydrate, carvedilol hydrobromide anhydrate, and/or other solvates thereof.

The present invention relates to a pharmaceutical composition, which comprises the aforementioned salts and/or solvates of carvedilol and a pharmaceutically acceptable carrier.

The present invention relates to a method of treating hypertension, congestive heart failure or angina, which comprises administering to a subject in need thereof an effective amount of a salt and/or novel crystalline form of carvedilol (i.e., as defined by the aforementioned salts and/or solvates) or a corresponding pharmaceutical composition, which contains such aforementioned salt, and/or novel crystalline forms of carvedilol.

Carvedilol is disclosed and claimed in U.S. Pat. No. 4,503,067 to Wiedemann et al. ("U.S. '067 Patent"). Reference should be made to U.S. '067 Patent for its full disclosure, which include methods of preparing and/or using the carvedilol compound, etc. The entire disclosure of the U.S. '067 Patent is incorporated hereby by reference in its entirety.

The present invention relates to a compound, which is a salt of carvedilol hydrobromide (such as crystalline carvedilol hydrobromide monohydrate), and/or a carvedilol solvate thereof.

In accordance with the present invention, it has been found unexpectedly that carvedilol hydrobromide can be isolated readily as a novel crystalline form, which displays much higher solubility when compared to the free base of carvedilol.

In particular, crystalline carvedilol hydrobromide monohydrate of the present invention can be prepared by crystallization from an acetone-water solvent system containing carvedilol and hydrobromic acid.

In accordance with the present invention suitable solvates of the instant invention may be prepared by preparing a slurry of the carvedilol hydrobromide salt in a solvent, such as dioxane, 1-pentanol, 2-methyl-1-propanol, trifluoroethanol, 2-propanol and n-propanol.

Suitable solvates of carvedilol as defined in the present invention, include, but are not limited to carvedilol hydrobromide 1-pentanol solvate, carvedilol hydrobromide 2-methyl-1-pentanol solvate, carvedilol hydrobromide trifluoroethanol solvate, carvedilol hydrobromide 2-propanol solvate, carvedilol hydrobromide n-propanol solvate #1, carvedilol hydrobromide n-propanol solvate #2, carvedilol hydrobromide ethanol solvate, carvedilol hydrobromide anhydrate, etc.

In the present invention, carvedilol hydrobromide anhydrate can be prepared by dissolving carvedilol in a solvent, such as dichloromethane, acetonitrile or isopropyl acetate, followed by the addition of anhydrous HBr (HBr in acetic acid or gaseous HBr).

It is recognized that the compounds of the present invention may exist in forms as stereoisomers, regioisomers, or diastereiomers, etc. These compounds may contain one or more asymmetric carbon atoms and may exist in racemic and optically active forms. For example, carvedilol may exist as as racemic mixture of R(+) and S(−) enantiomers, or in separate respectively optically forms, i.e., existing separately as either the R(+) enantiomer form or in the S(+) enantiomer form. All of these individual compounds, isomers, and mixtures thereof are included within the scope of the present invention.

According to the instant invention, the various forms of carvedilol hydrobromide and/or corresponding solvates are distinguished from each other using different spectroscopic identification techniques, such as Infrared (IR), Raman, Differential Scanning Calorimetry (DSC) and X-ray powder diffraction, etc.

Figure 82:
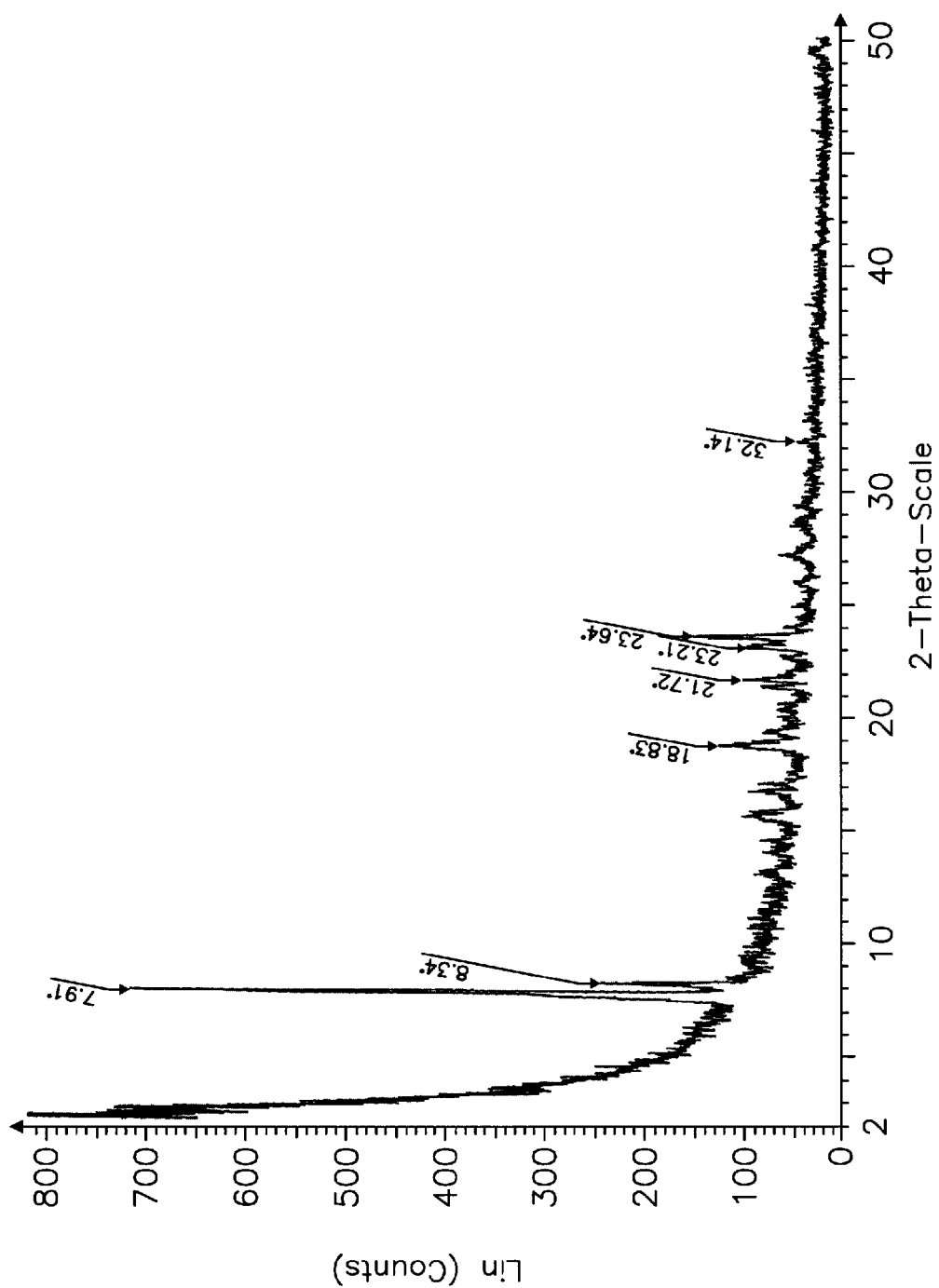
FIG. 82 is an x-ray powder diffractogram for carvedilol hydrobromide 2-propanol solvate.

Specifically, a salt or novel crystalline form of carvedilol, which includes carvedilol hydrobromide monohydrate, anhydrate, and/or other solvates thereof, are characterized by spectroscopic data as described below and depicted in FIGS. 1-82.

For example, crystalline carvedilol hydrobromide monohydrate (see, Example 1: Form 1) is identified by an x-ray diffraction pattern as shown substantially in FIG. 1, which depicts characteristic peaks in degrees two-theta (2θ): i.e., 6.5±0.2 (2θ), 10.3±0.2 (2θ), 15.7±0.2 (2θ), 16.3±0.2 (2θ), 19.8±0.2 (2θ), 20.1±0.2 (2θ), 21.9±0.2 (2θ), 25.2±0.2 (2θ), and 30.6±0.2 (2θ).

Figure 78:
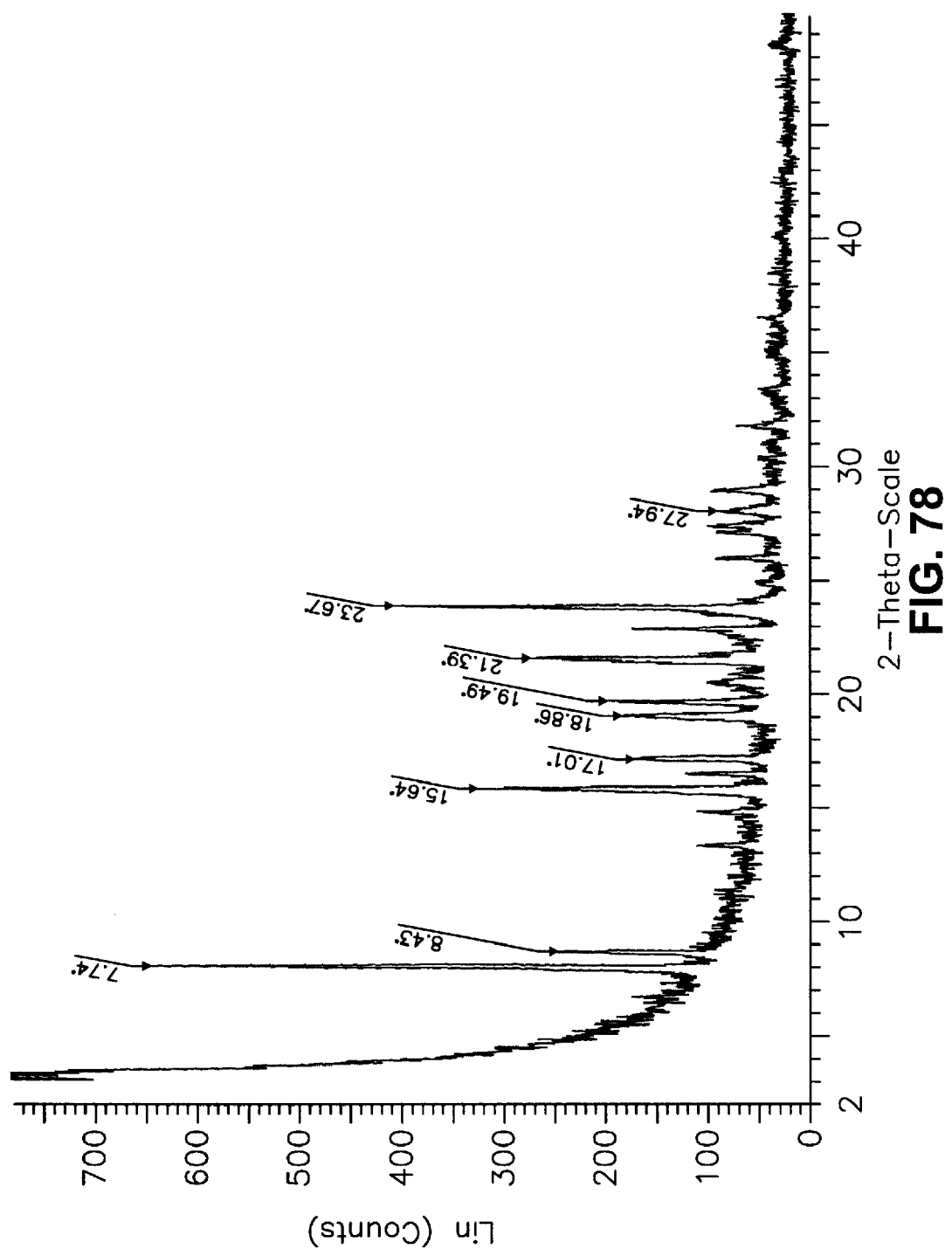
FIG. 78 is an x-ray powder diffractogram for carvedilol hydrobromide dioxane solvate.

Crystalline carvedilol hydrobromide dioxane solvate (see, Example 2: Form 2) also is identified by an x-ray diffraction pattern as shown substantially in FIG. 78, which depicts characteristic peaks in degrees two-theta (2θ): i.e., 7.7±0.2 (2θ), 8.4±0.2 (2θ), 15.6±0.2 (2θ), 17.0±0.2 (2θ), 18.7±0.2 (2θ), 19.5±0.2 (2θ), 21.4±0.2 (2θ), 23.7±0.2 (2θ), and 27.9±0.2 (2θ).

Figure 79:
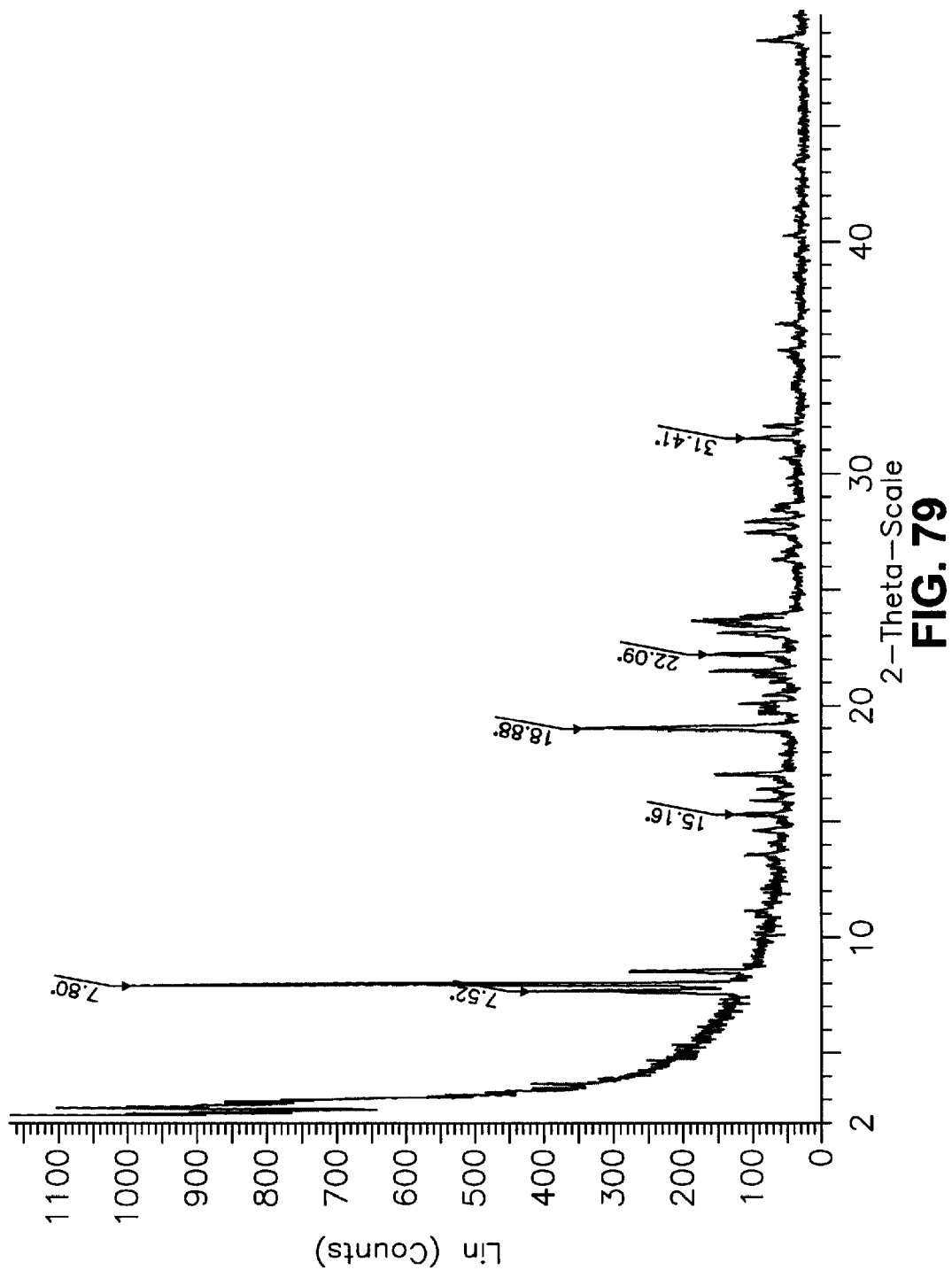
FIG. 79 is an x-ray powder diffractogram for carvedilol hydrobromide 1-pentanol solvate.

Crystalline carvedilol hydrobromide 1-pentanol solvate (see, Example 3: Form 3) also is identified by an x-ray diffraction pattern as shown substantially in FIG. 79, which depicts characteristic peaks in degrees two-theta (2θ): i.e., 77.5±0.2 (2θ), 7.8±0.2 (2θ), 15.2±0.2 (2θ), 18.9±0.2 (2θ), 22.1±0.2 (2θ), and 31.4±0.2 (2θ).

Figure 80:
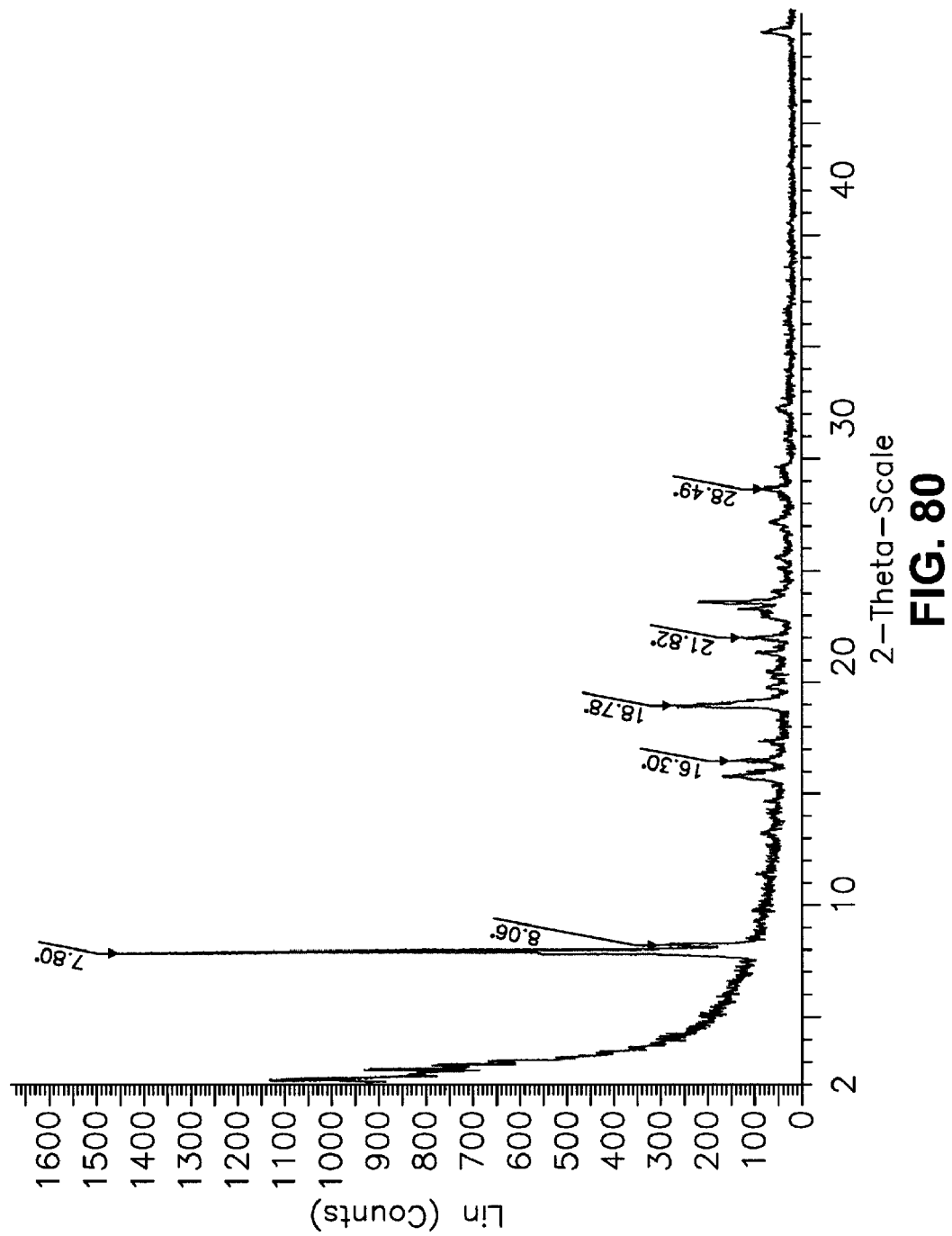
FIG. 80 is an x-ray powder diffractogram for carvedilol hydrobromide 2-methyl-1-propanol solvate.

Crystalline carvedilol hydrobromide 2-methyl-1-propanol solvate (see, Example 4: Form 4) also is identified by an x-ray diffraction pattern as shown substantially in FIG. 80, which depicts characteristic peaks in degrees two-theta (2θ): i.e., 7.8±0.2 (2θ), 8.1±0.2 (2θ), 16.3±0.2 (2θ), 18.8±0.2 (2θ), 21.8±0.2 (2θ), and 28.5±0.2 (2θ).

Figure 81:
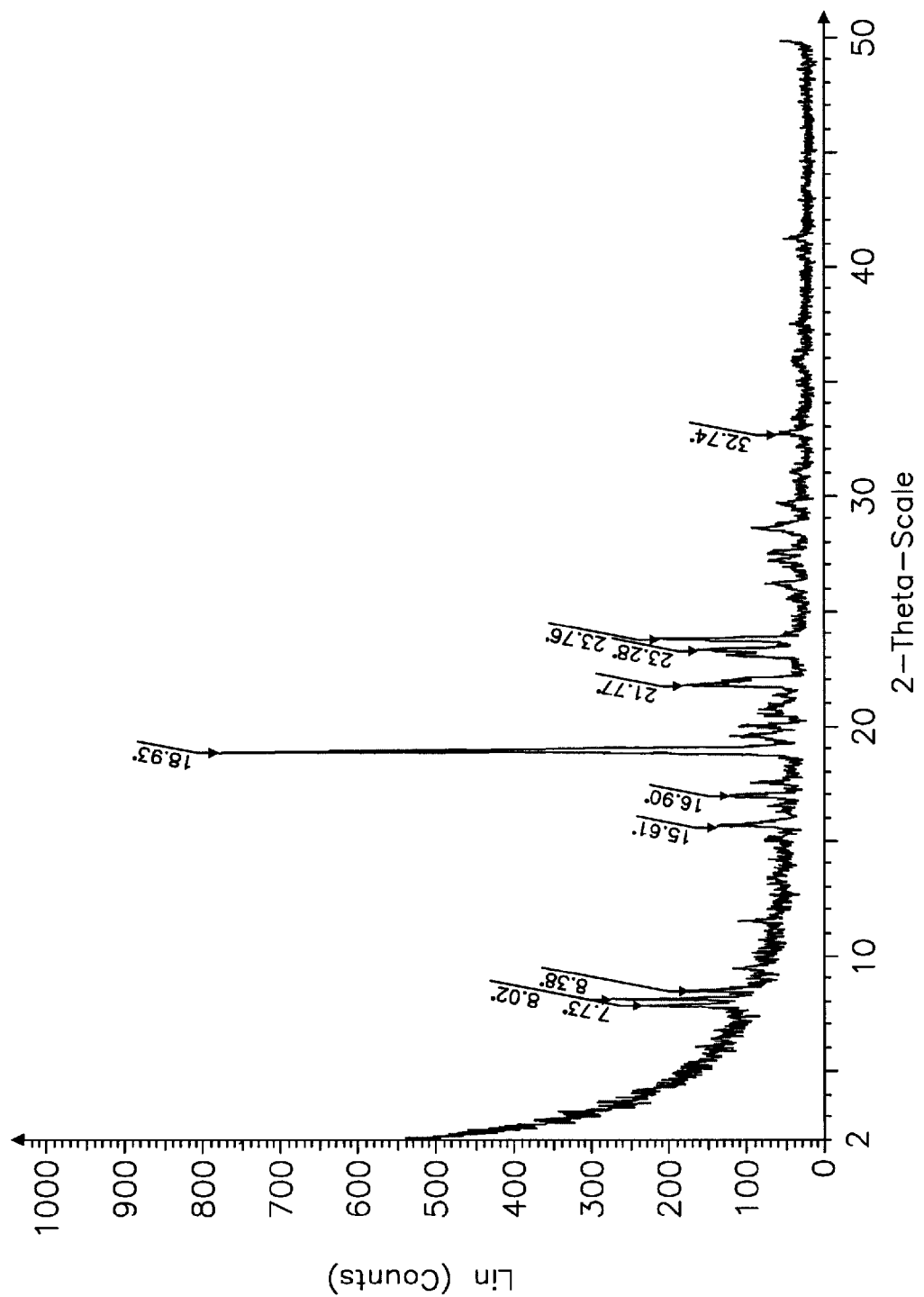
FIG. 81 is an x-ray powder diffractogram for carvedilol hydrobromide trifluoroethanol solvate.

Crystalline carvedilol hydrobromide trifluoroethanol solvate (see, Example 5: Form 5) also is identified by an x-ray diffraction pattern as shown substantially in FIG. 81, which depicts characteristic peaks in degrees two-theta (2θ): i.e., 7.7±0.2 (2θ), 8.4±0.2 (2θ), 15.6±0.2 (2θ), 16.9±0.2 (2θ), 18.9±0.2 (2θ), 21.8±0.2 (2θ), 23.8±0.2 (2θ), 23.7±0.2 (2θ), and 32.7±0.2 (2θ).

Crystalline carvedilol hydrobromide 2-propanol solvate (see, Example 6: Form 6) also is identified by an x-ray diffraction pattern as shown substantially in FIG. 82, which depicts characteristic peaks in degrees two-theta (2θ): i.e., 7.9±0.2 (2θ), 8.3±0.2 (2θ), 18.8±0.2 (2θ), 21.7±0.2 (2θ), 23.2±0.2 (2θ), 23.6±0.2 (2θ), and 32.1±0.2 (2θ).

Figure 46:
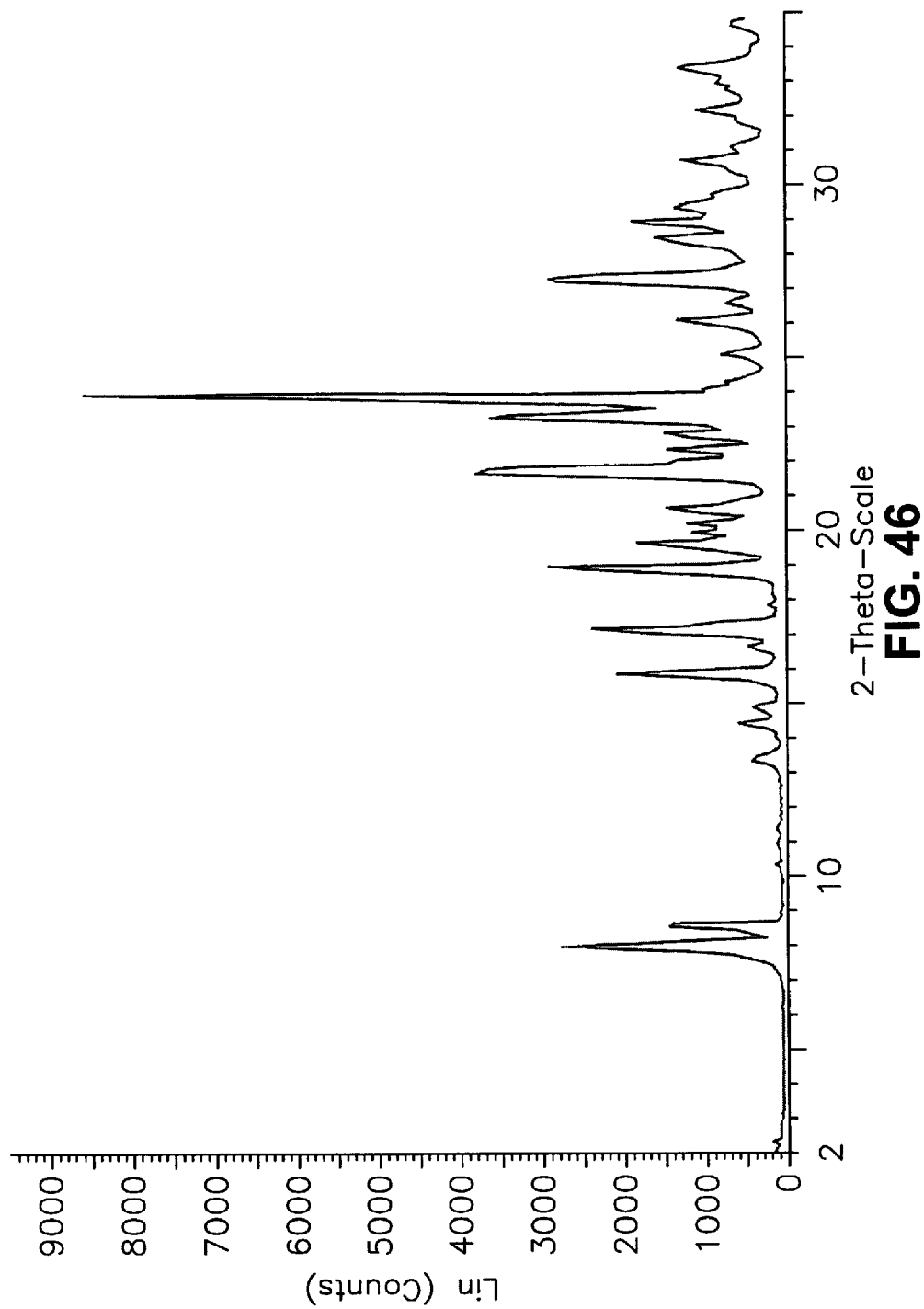
FIG. 46 is an x-ray powder diffractogram for carvedilol hydrobromide n-propanol solvate #1.
Figure 47:
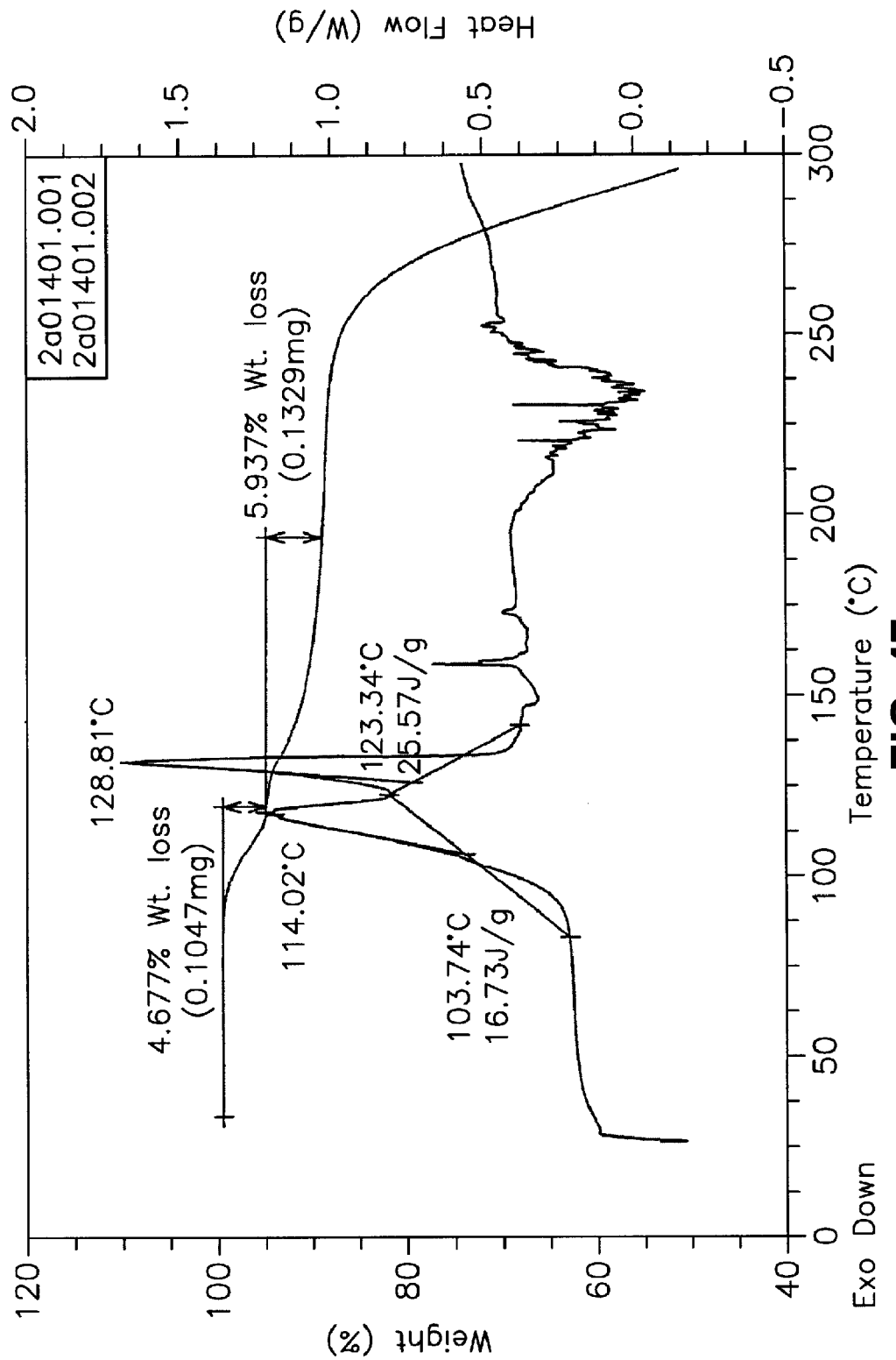
FIG. 47 shows the thermal analysis results for carvedilol hydrobromide n-propanol solvate #1.
Figure 48:
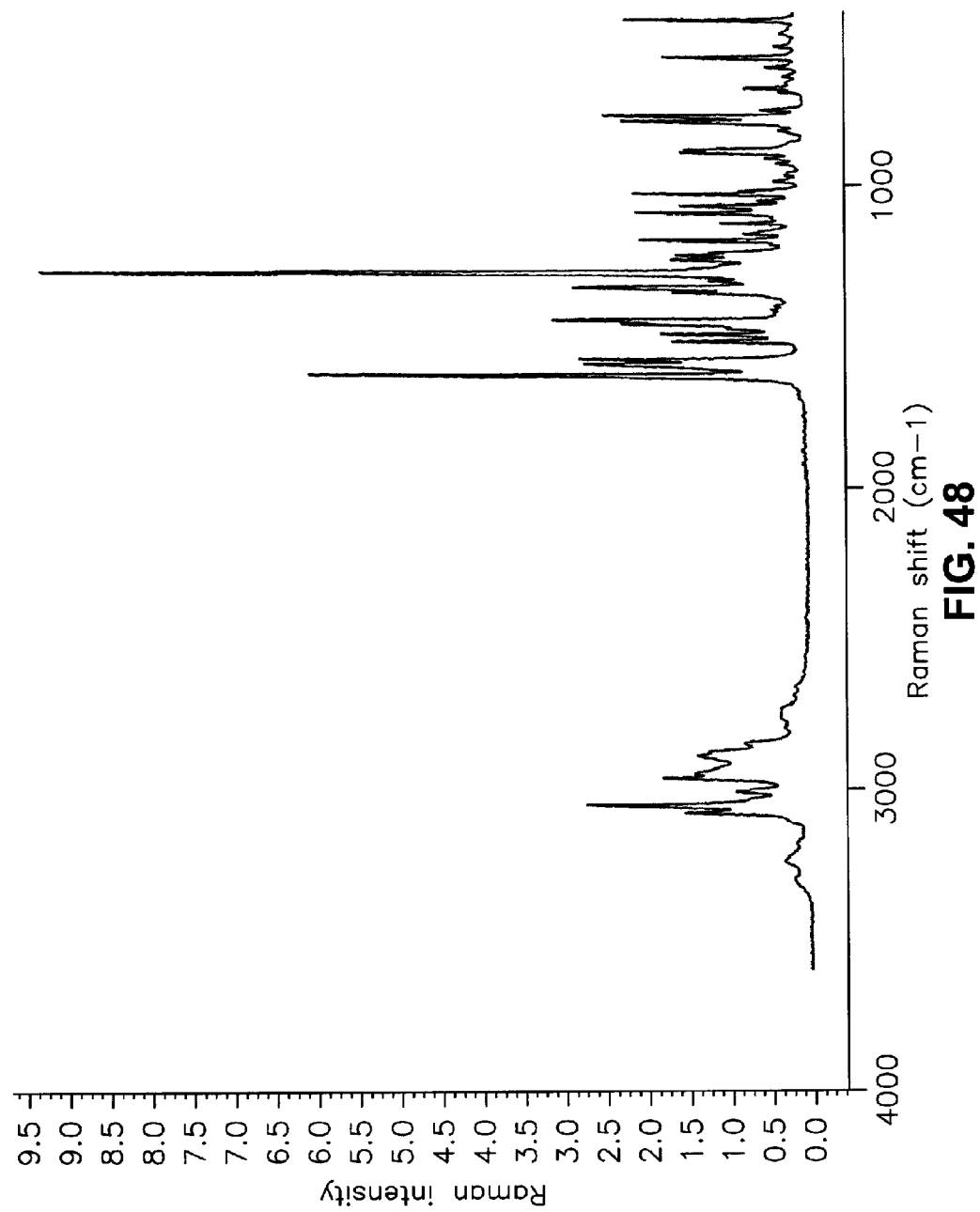
FIG. 48 is an FT-Raman spectrum for carvedilol hydrobromide n-propanol solvate #1.
Figure 49:
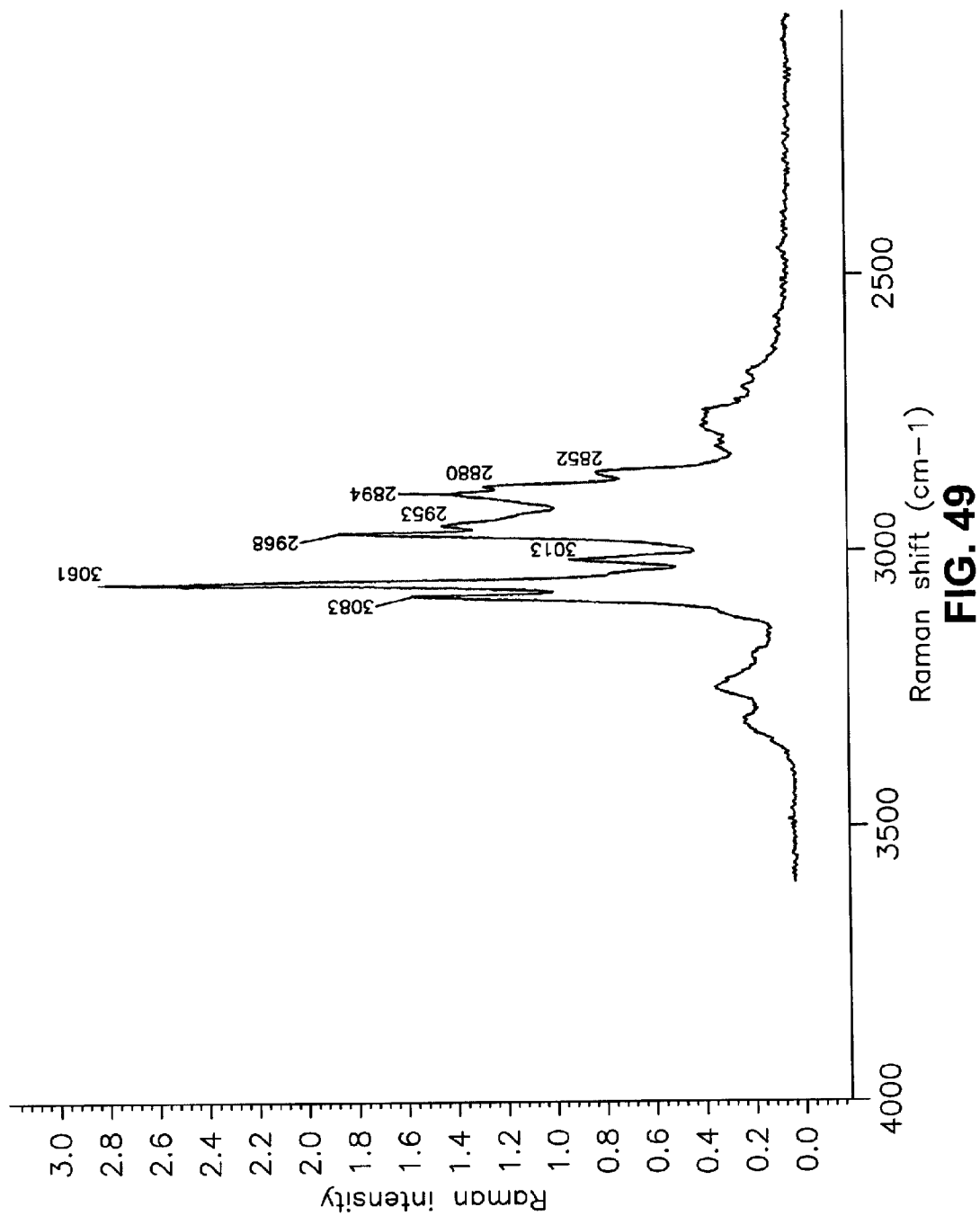
FIG. 49 is an FT-Raman spectrum for carvedilol hydrobromide n-propanol solvate #1 in the 4000-2000 $cm^{-1}$ region of the spectrum.
Figure 50:
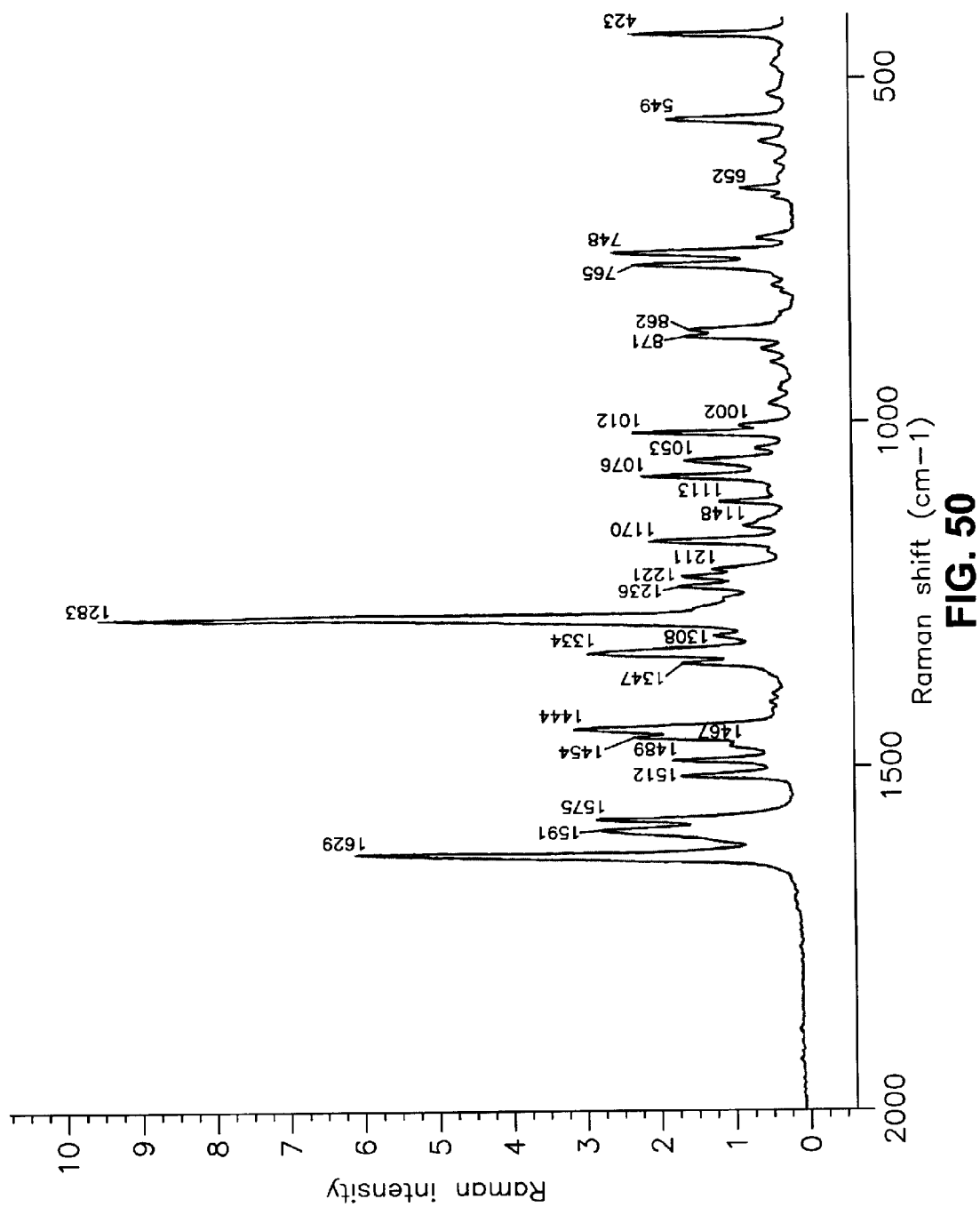
FIG. 50 is an FT-Raman spectrum for carvedilol hydrobromide n-propanol solvate #1 in the 2000-400 cm$^{-1}$ region of the spectrum.
Figure 51:
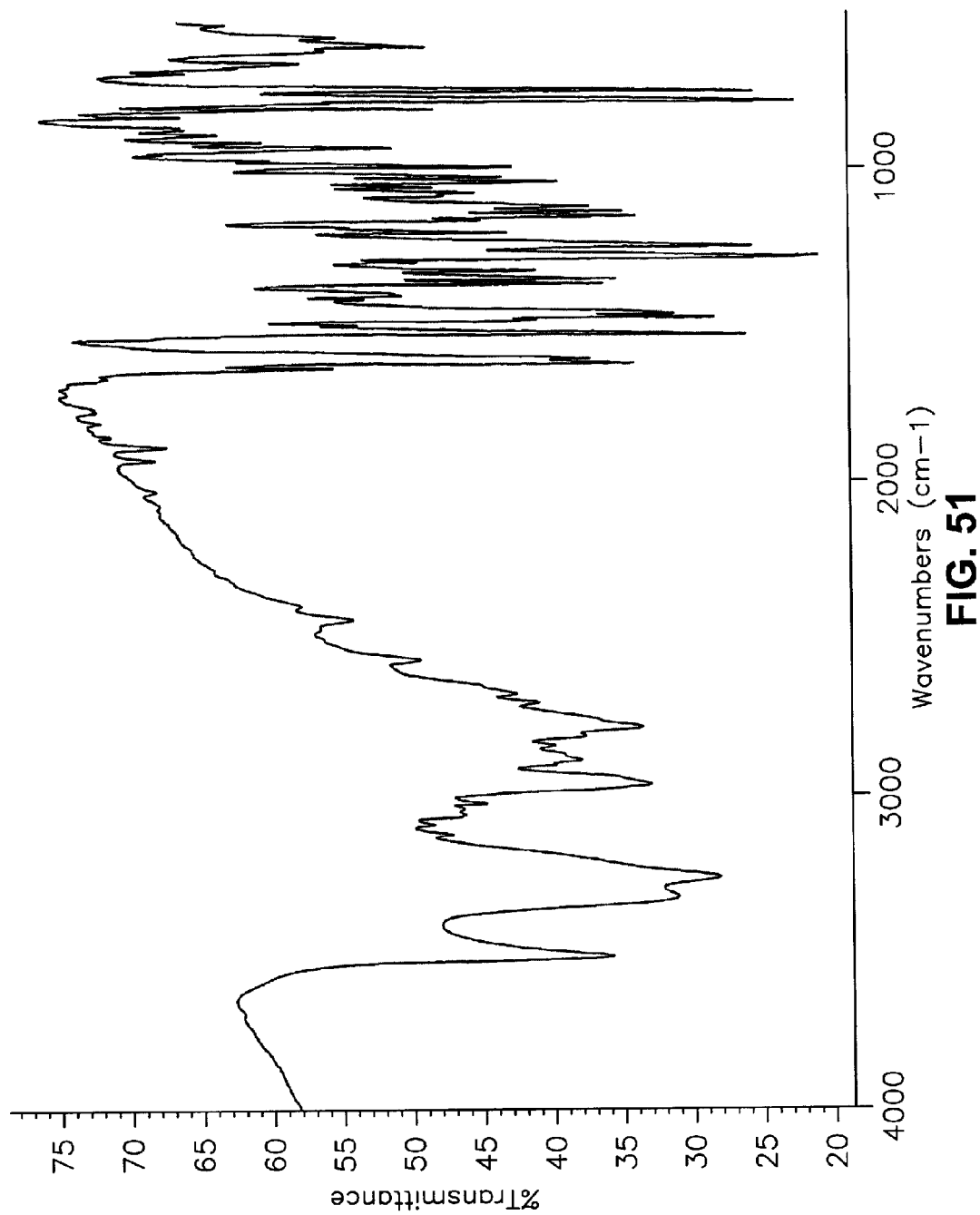
FIG. 51 is an FT-IR spectrum for carvedilol hydrobromide n-propanol solvate #1.
Figure 52:
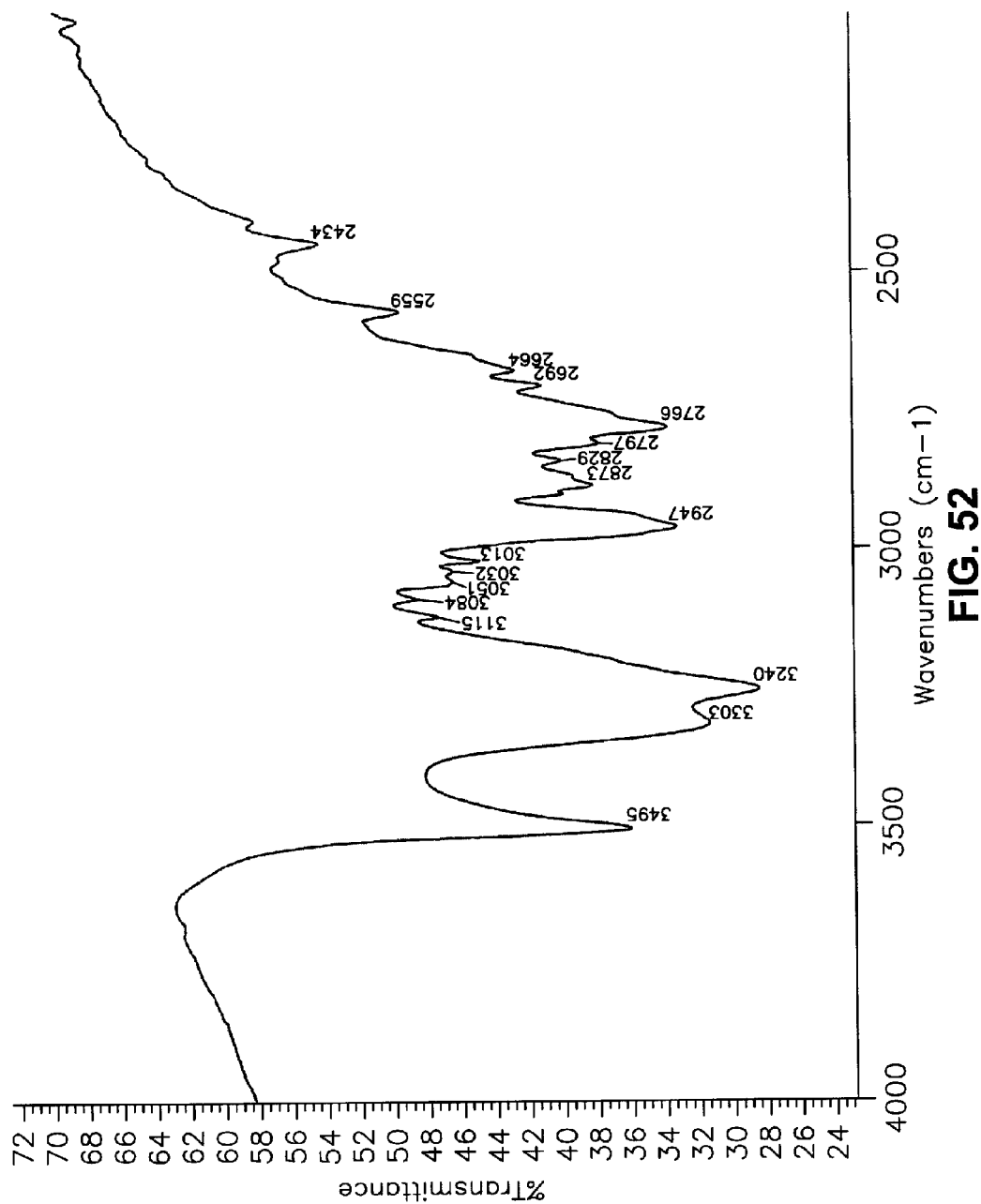
FIG. 52 is an FT-IR spectrum for carvedilol hydrobromide n-propanol solvate #1 in the 4000-2000 cm$^{-1}$ region of the spectrum.
Figure 53:
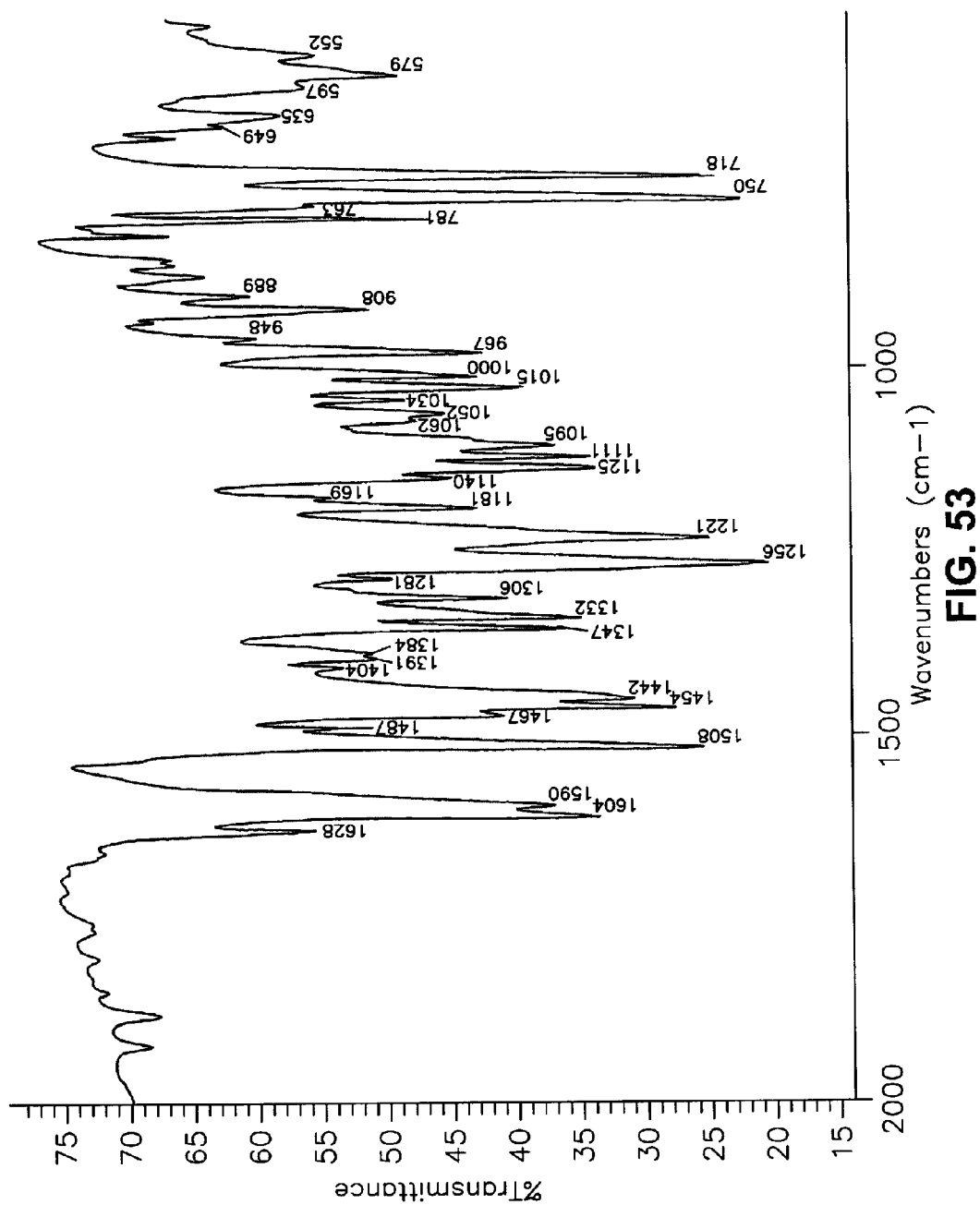
FIG. 53 is an FT-IR spectrum for carvedilol hydrobromide n-propanol solvate #1 in the 2000-500 cm$^{-1}$ region of the spectrum.

Crystalline carvedilol hydrobromide n-propanol solvate #1 (see, Example 7: Form 7) also is identified by an x-ray diffraction pattern as shown substantially in FIG. 46, which depicts characteristic peaks in degrees two-theta (2θ): i.e., 7.9±0.2 (2θ), 8.5±0.2 (2θ), 17.0±0.2 (2θ), 18.8±0.2 (2θ), 21.6±0.2 (2θ), 23.1±0.2 (2θ), 23.6±0.2 (2θ), and 21.2±0.2 (2θ).

Figure 54:
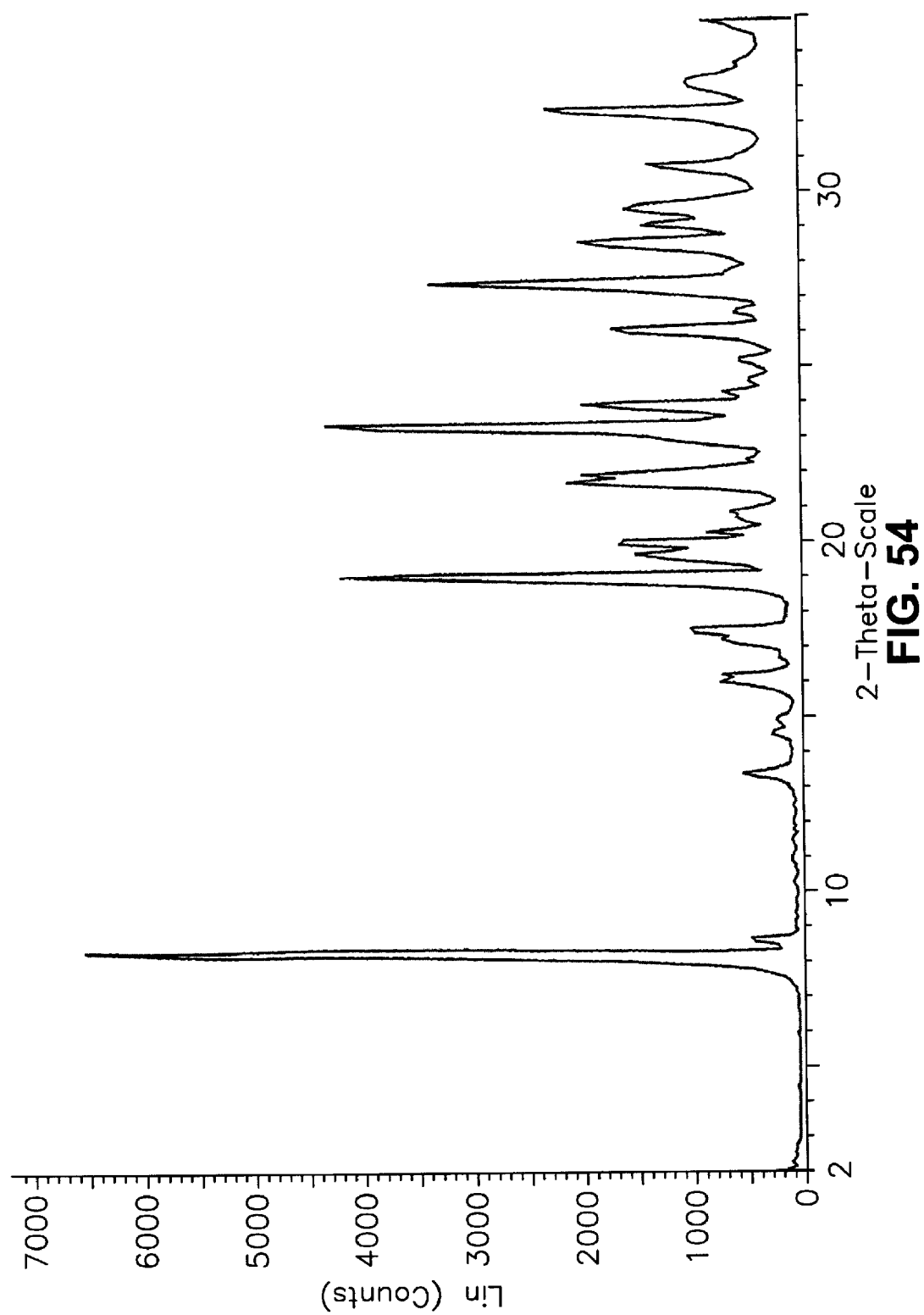
FIG. 54 is an x-ray powder diffractogram for carvedilol hydrobromide n-propanol solvate #2.
Figure 55:
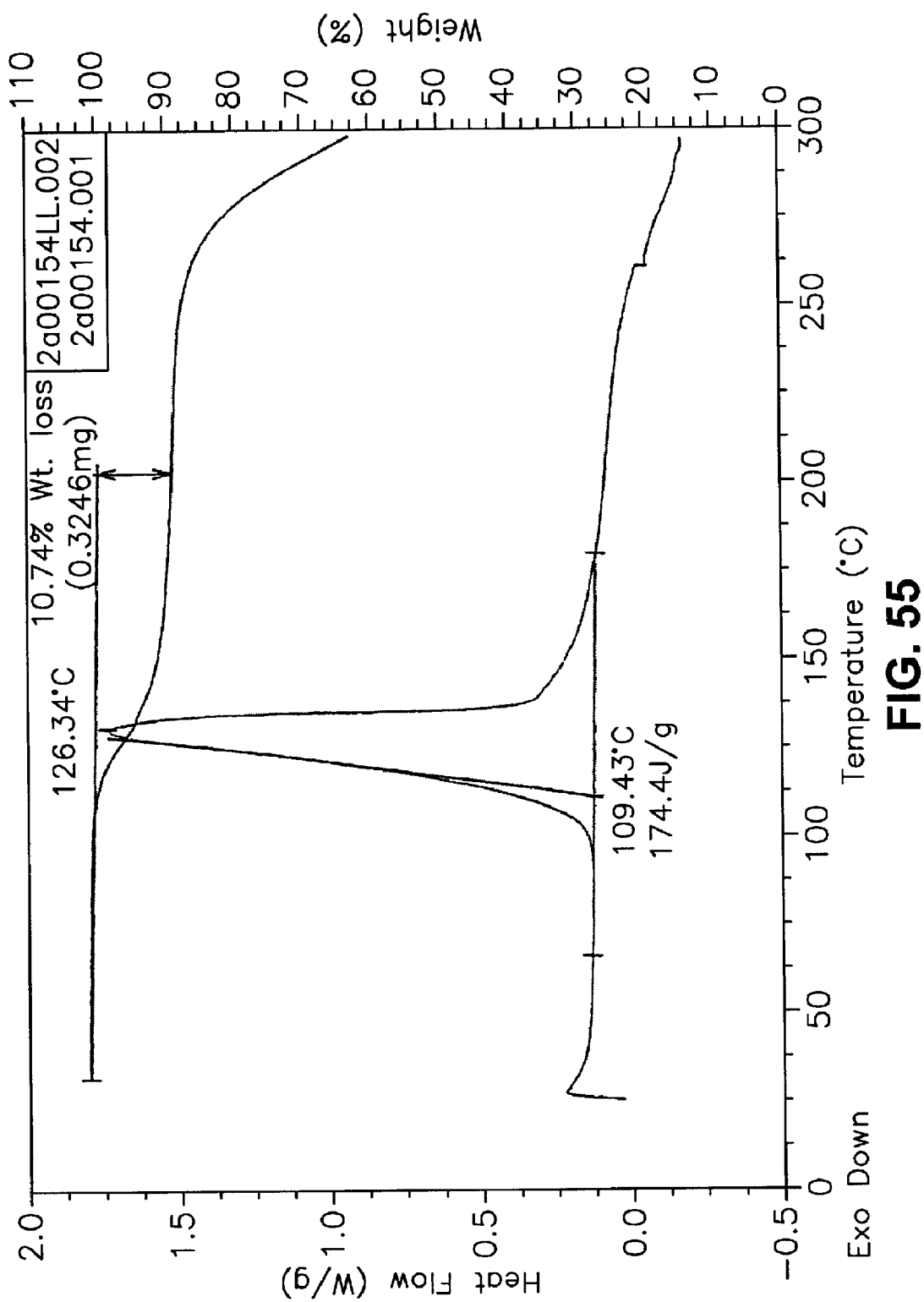
FIG. 55 shows the thermal analysis results for carvedilol hydrobromide n-propanol solvate #2.
Figure 56:
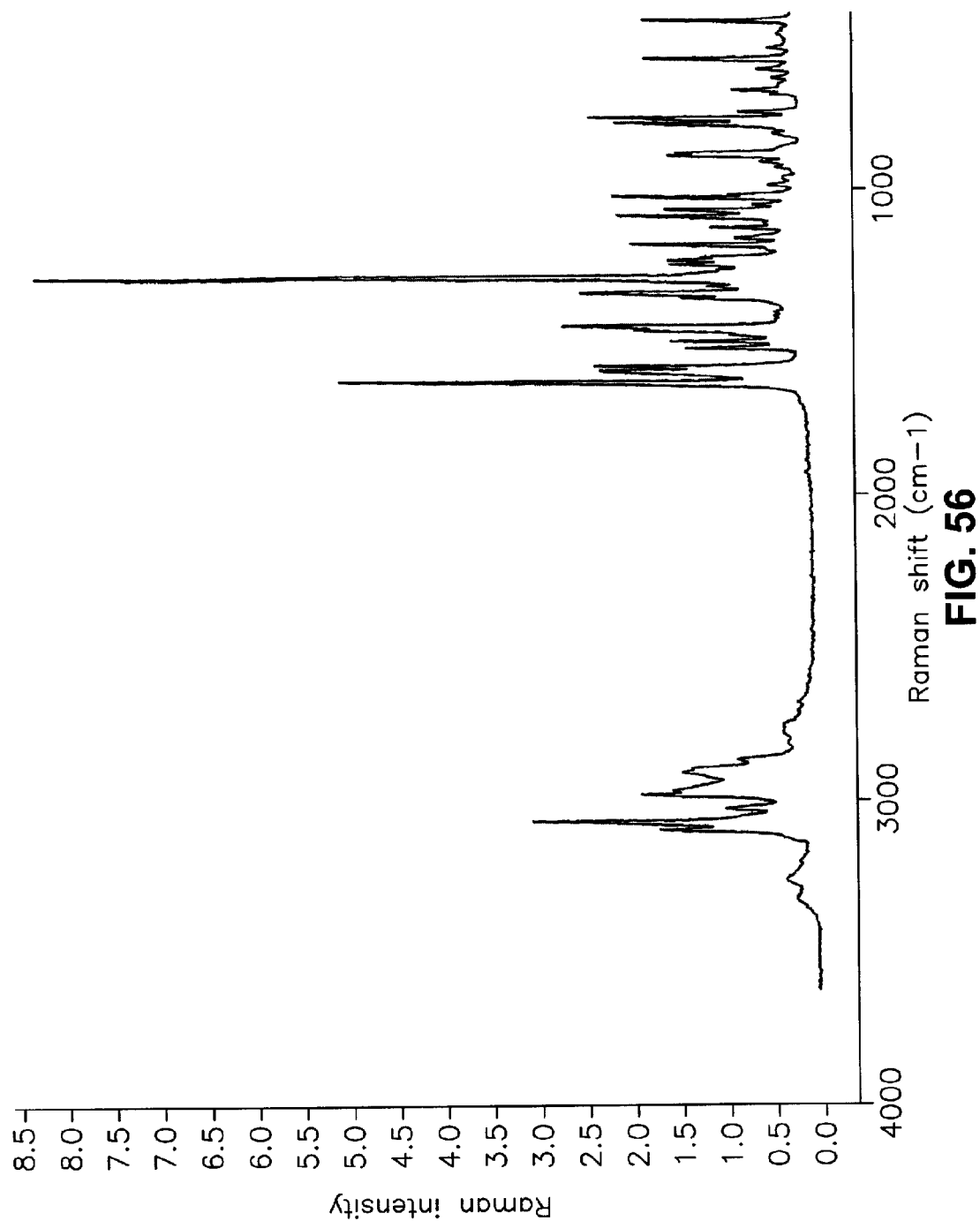
FIG. 56 is an FT-Raman spectrum for carvedilol hydrobromide n-propanol solvate #2.
Figure 57:
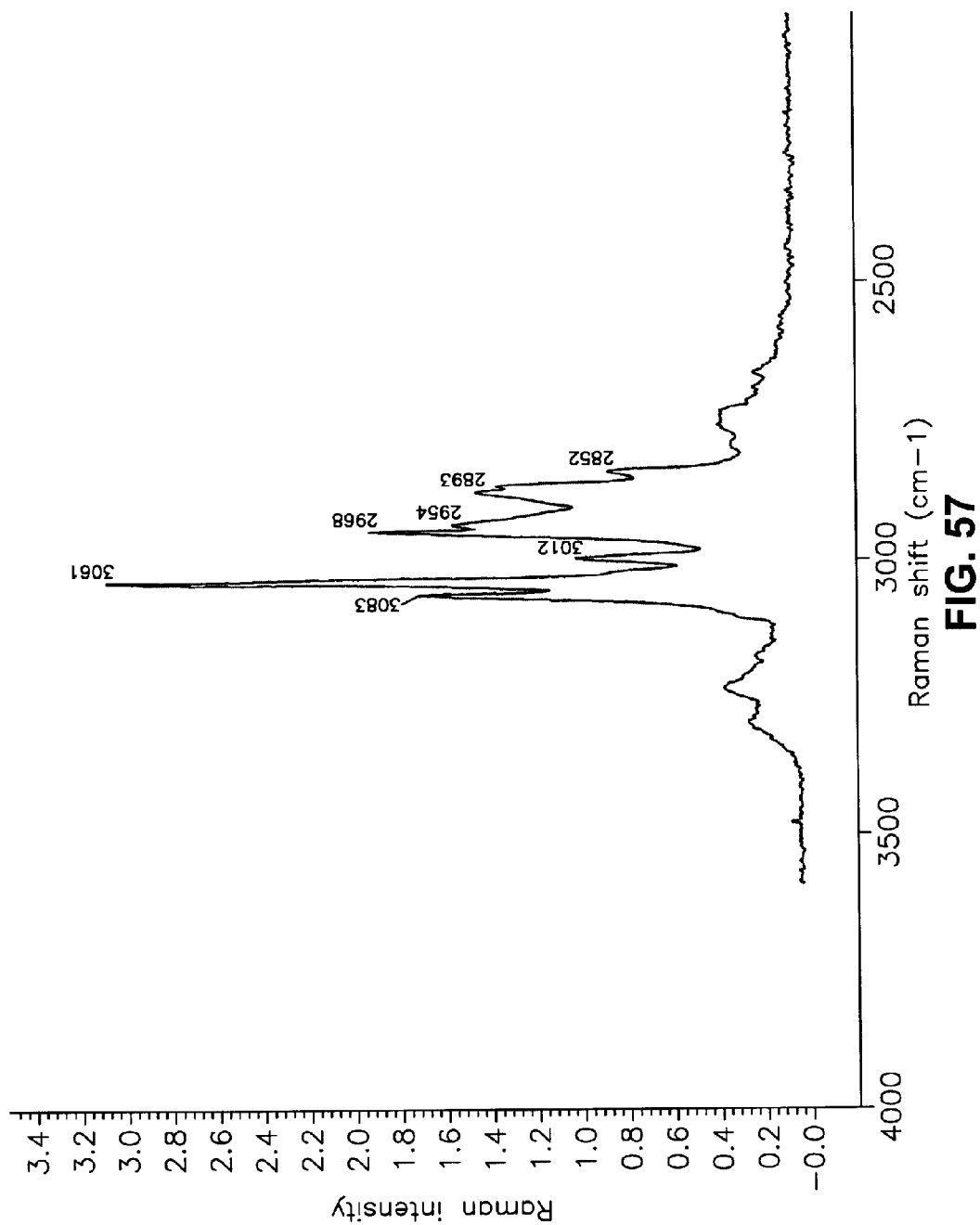
FIG. 57 is an FT-Raman spectrum for carvedilol hydrobromide n-propanol solvate #2 in the 4000-2000 cm$^{-1}$ region of the spectrum.
Figure 58:
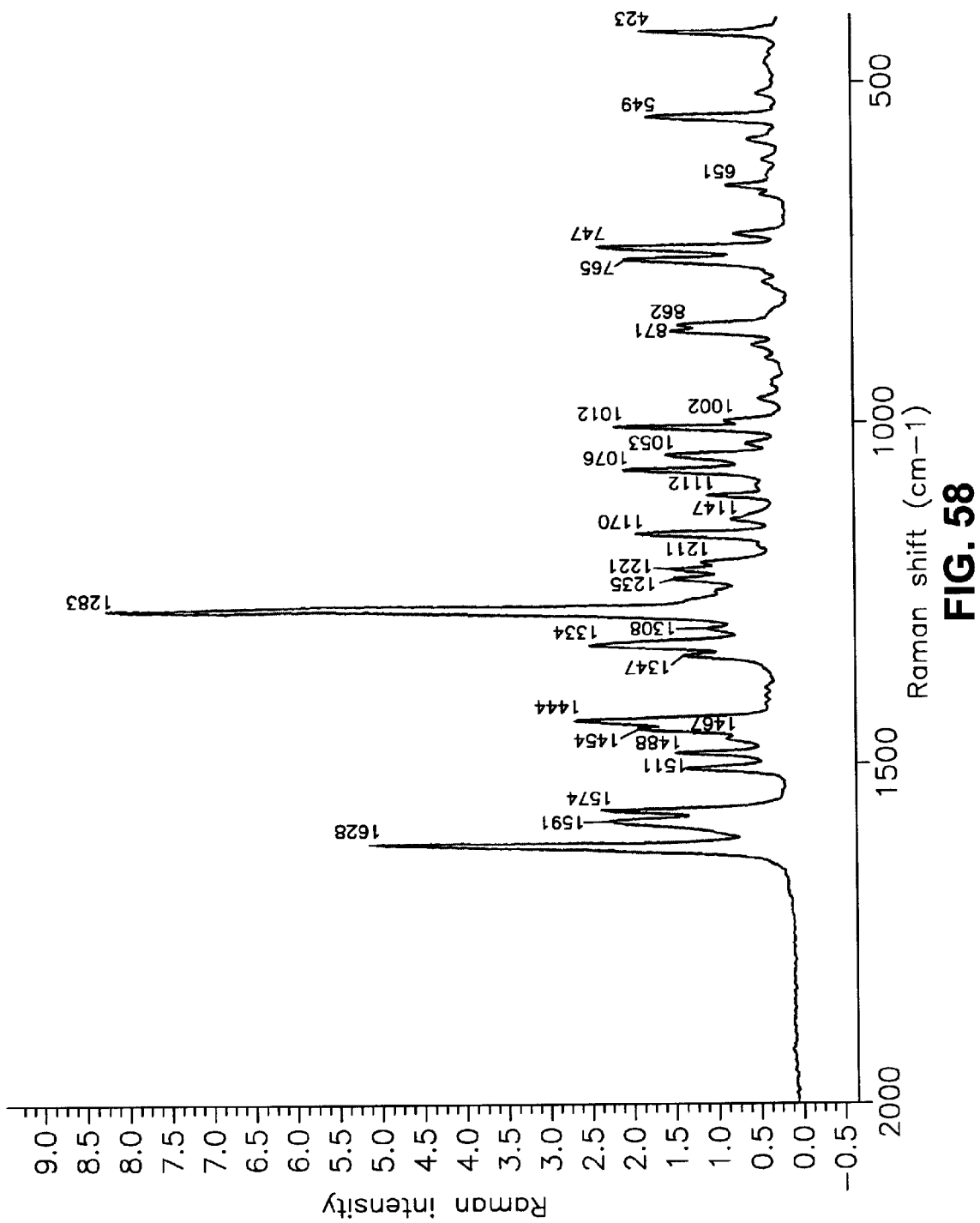
FIG. 58 is an FT-Raman spectrum for carvedilol hydrobromide n-propanol solvate #2 in the 2000-400 cm$^{-1}$ region of the spectrum.
Figure 59:
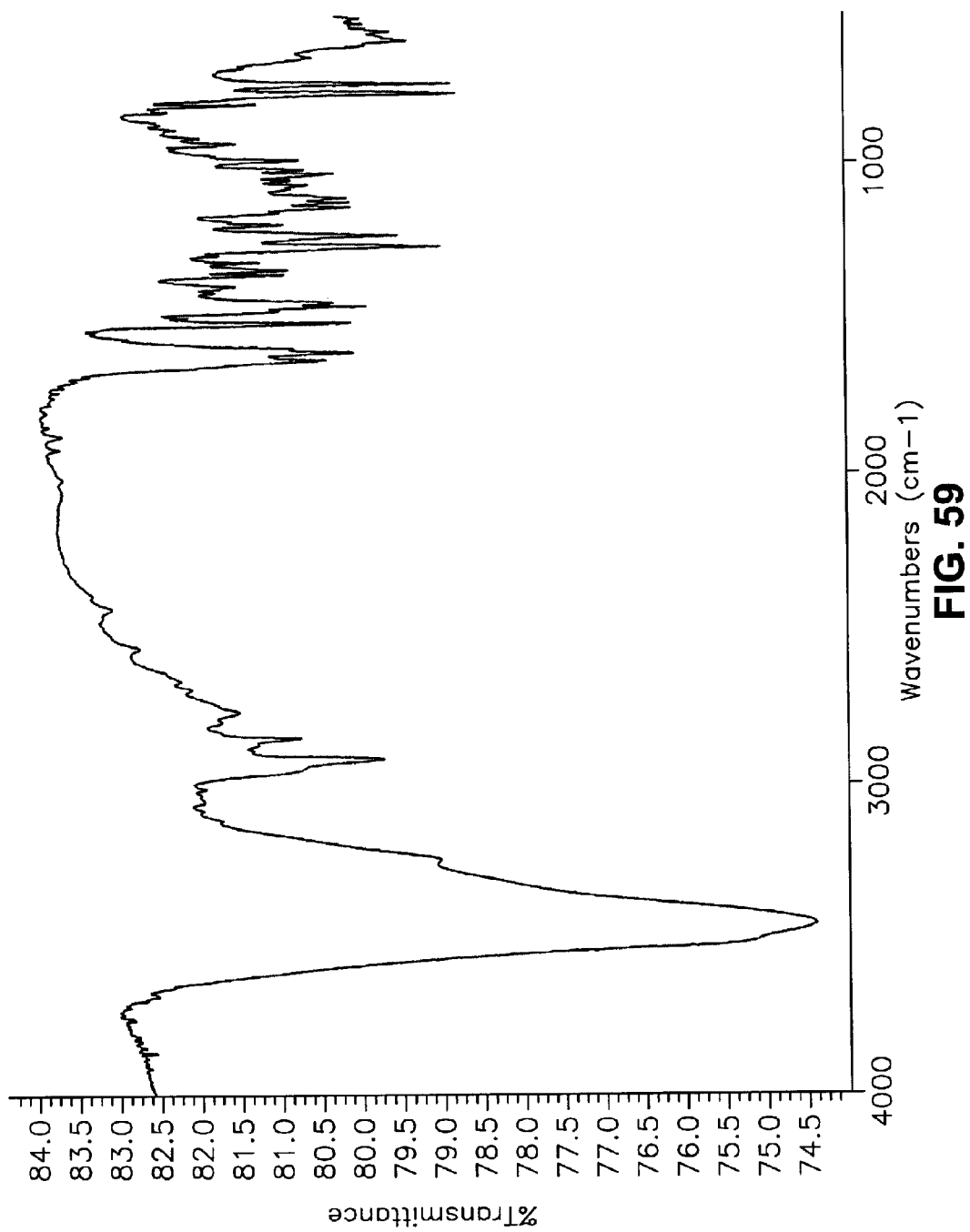
FIG. 59 is an FT-IR spectrum for carvedilol hydrobromide n-propanol solvate #2.
Figure 60:
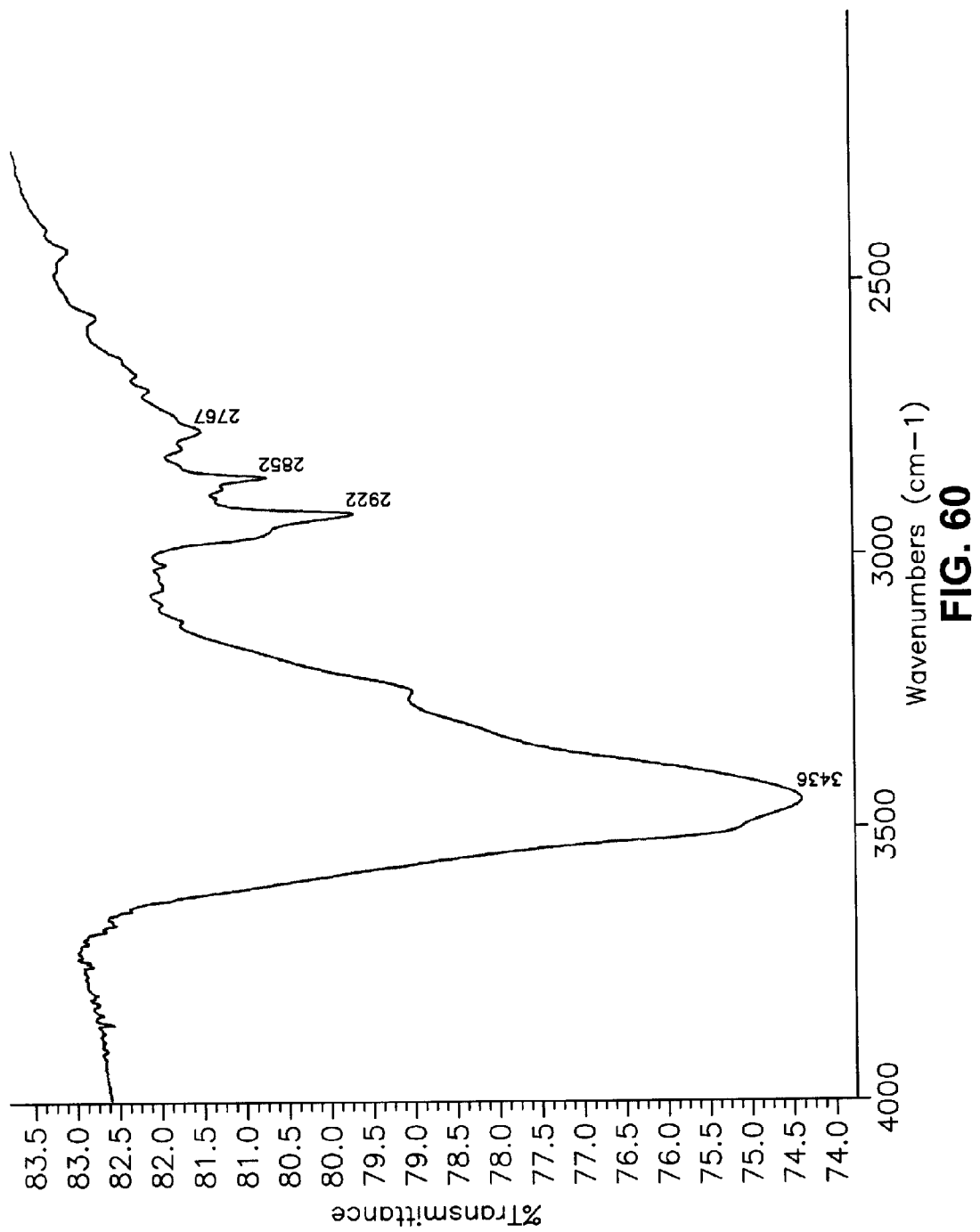
FIG. 60 is an FT-IR spectrum for carvedilol hydrobromide n-propanol solvate #2 in the 4000-2000 cm$^{-1}$ region of the spectrum.
Figure 61:
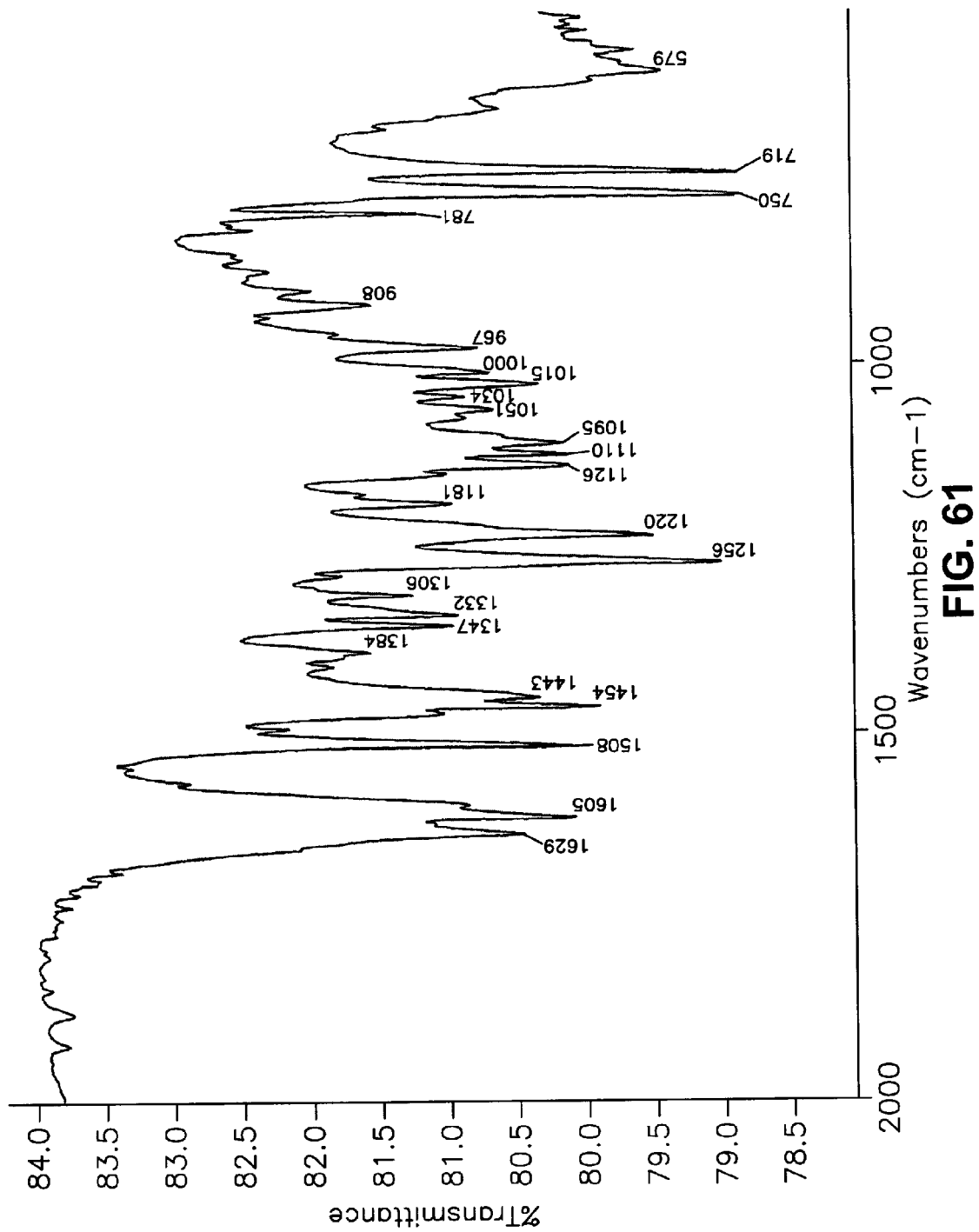
FIG. 61 is an FT-IR spectrum for carvedilol hydrobromide n-propanol solvate #2 in the 2000-500 cm$^{-1}$ region of the spectrum.

Crystalline carvedilol hydrobromide n-propanol solvate #2 (see, Example 8: Form 8) also is identified by an x-ray diffraction pattern as shown substantially in FIG. 54, which depicts characteristic peaks in degrees two-theta (2θ): i.e., 8.0±0.2 (2θ), 18.8±0.2 (2θ), 21.6±0.2 (2θ), 23.1±0.2 (2θ), 25.9±0.2 (2θ), 27.2±0.2 (2θ), 30.6±0.2 (2θ), and 32.2±0.2 (2θ).

Figure 62:
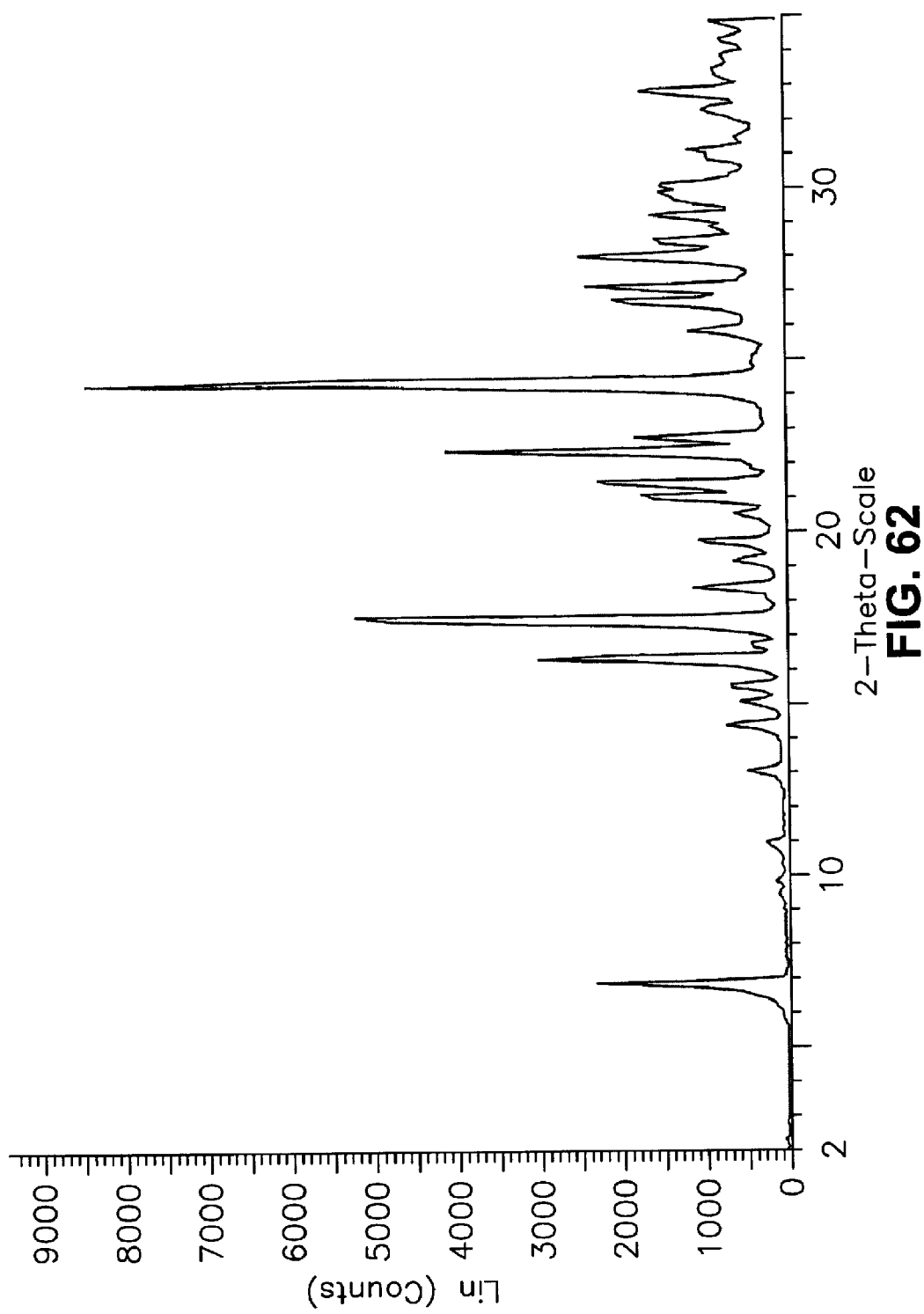
FIG. 62 is an x-ray powder diffractogram for carvedilol hydrobromide anhydrous.
Figure 63:
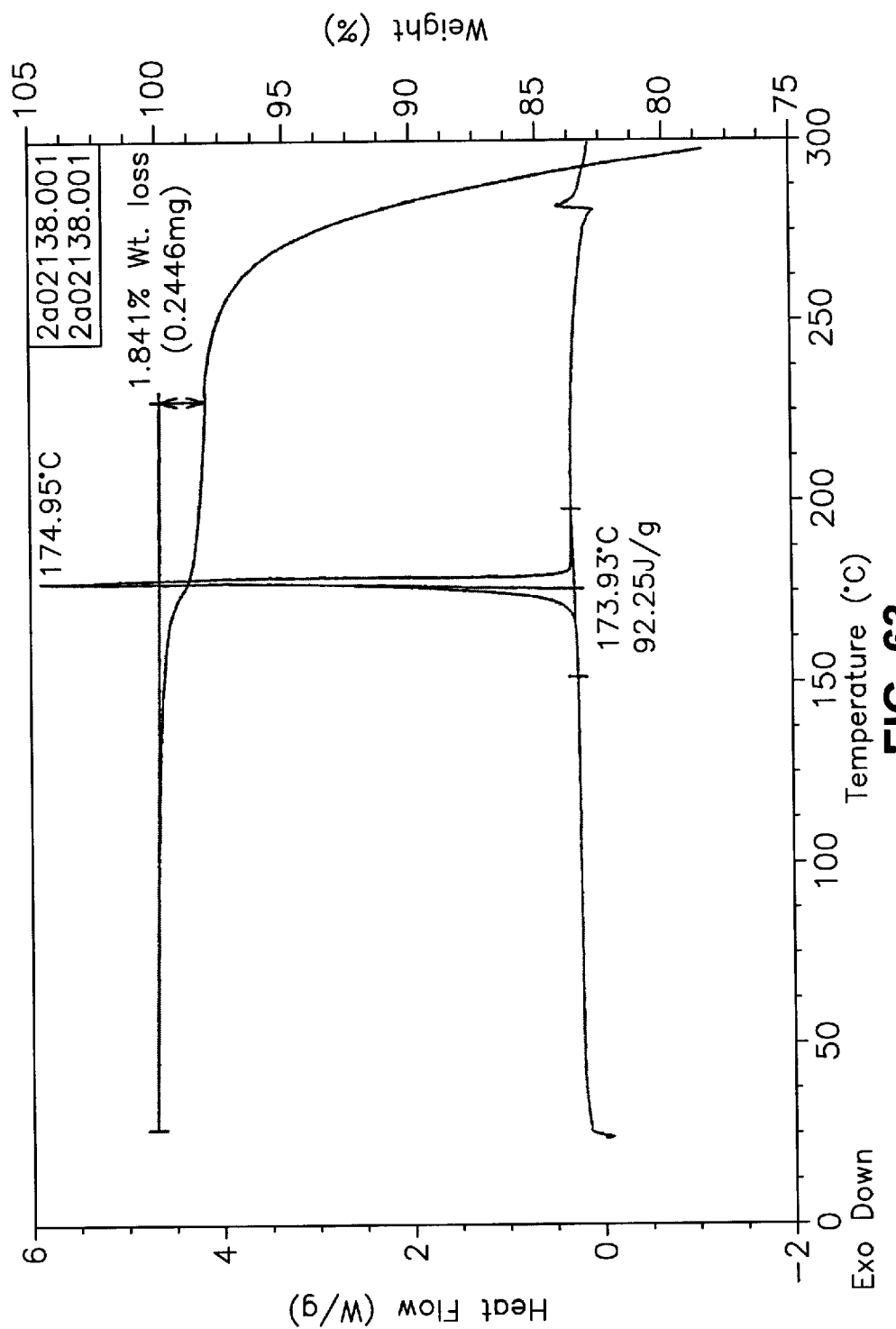
FIG. 63 shows the thermal analysis results for carvedilol hydrobromide anhydrous.

Crystalline carvedilol hydrobromide anhydrous (see, Example 9: Form 9) also is identified by an x-ray diffraction pattern as shown substantially in FIG. 62, which depicts characteristic peaks in degrees two-theta (2θ): i.e., 6.6±0.2 (2θ), 16.1±0.2 (2θ), 17.3±0.2 (2θ), 21.2±0.2 (2θ), 22.1±0.2 (2θ), 24.1±0.2 (2θ), and 27.9±0.2 (2θ).

Figure 70:
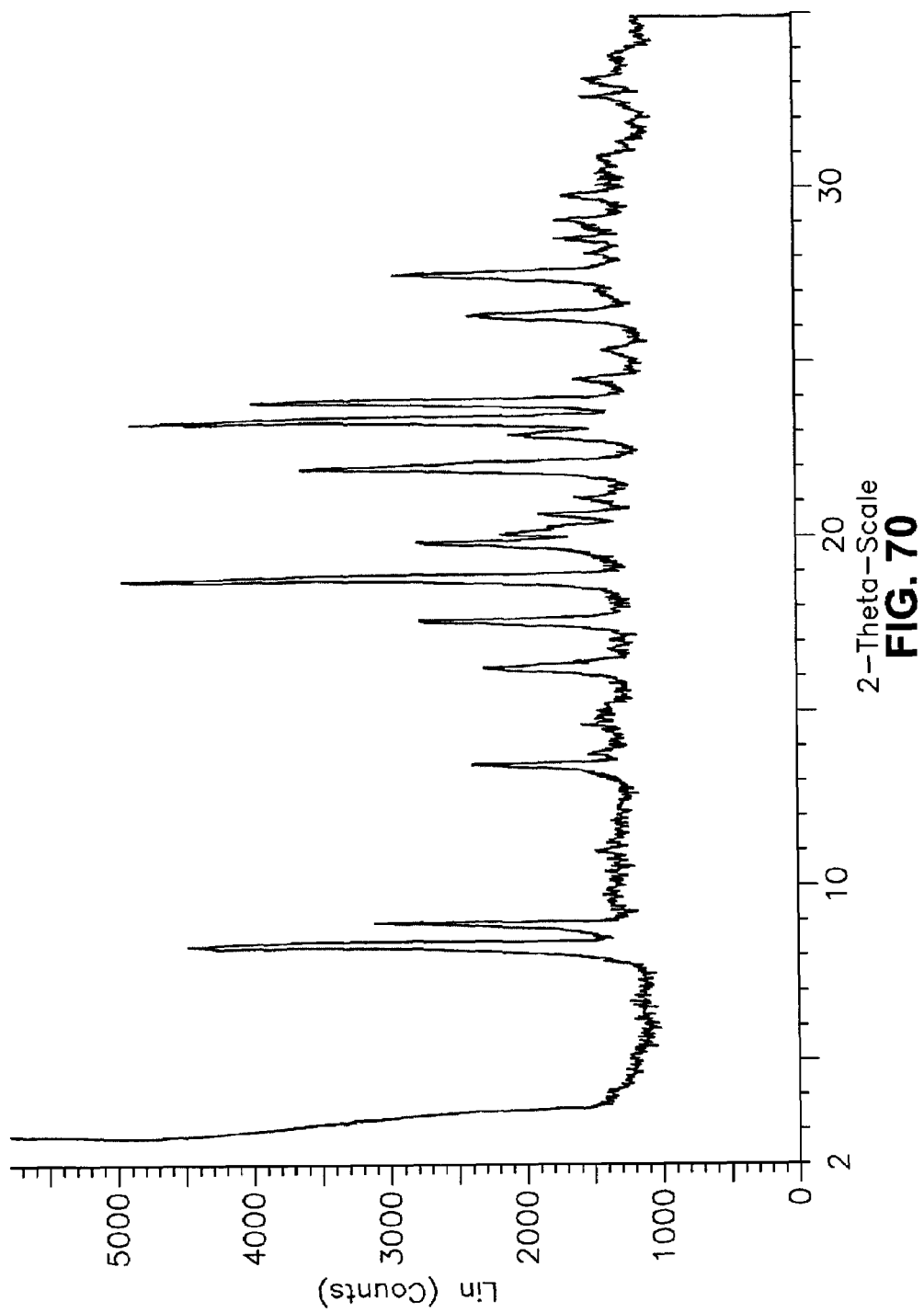
FIG. 70 is an x-ray powder diffractogram for carvedilol hydrobromide ethanol solvate.
Figure 71:
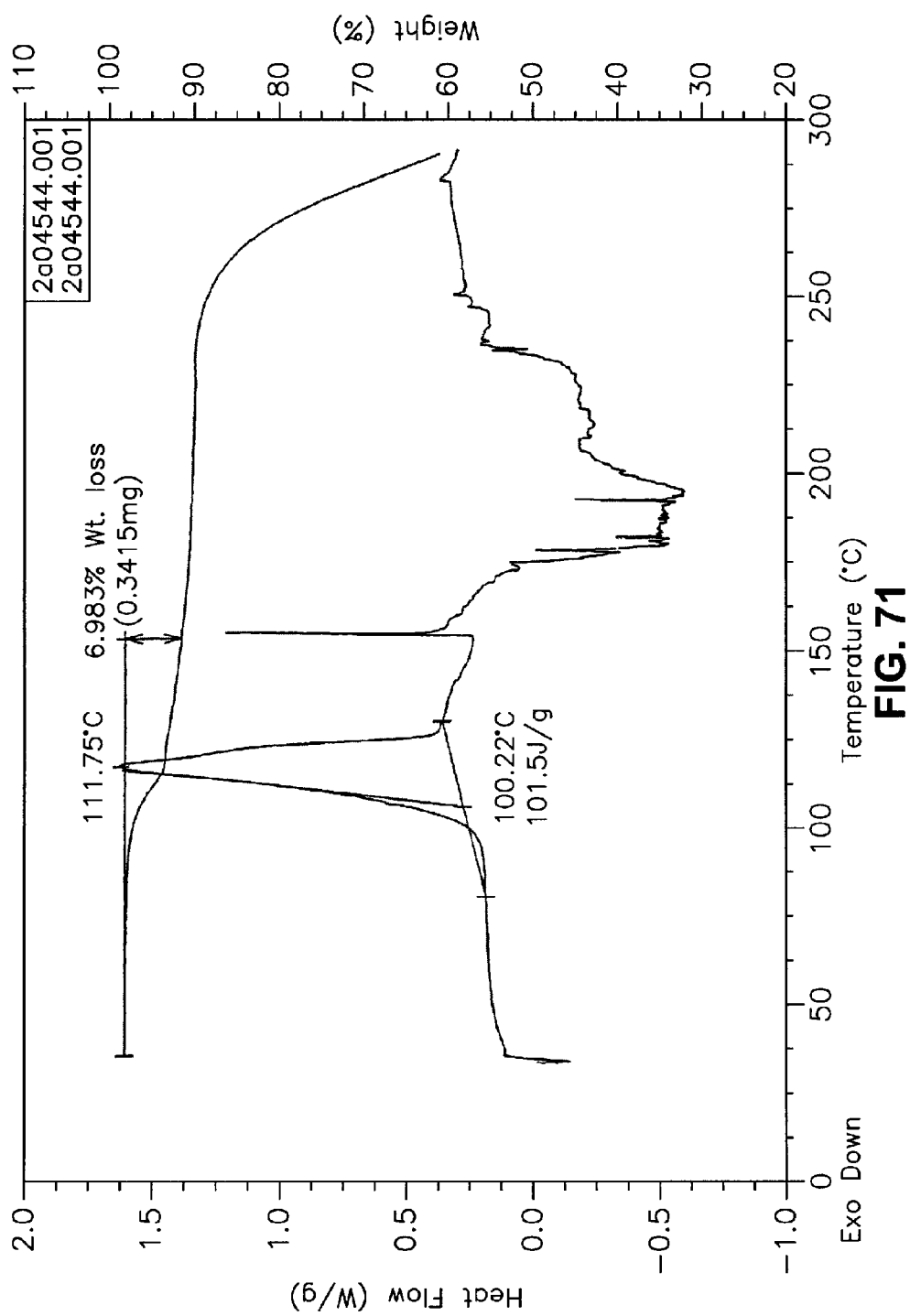
FIG. 71 shows the thermal analysis results for carvedilol hydrobromide ethanol solvate.
Figure 72:
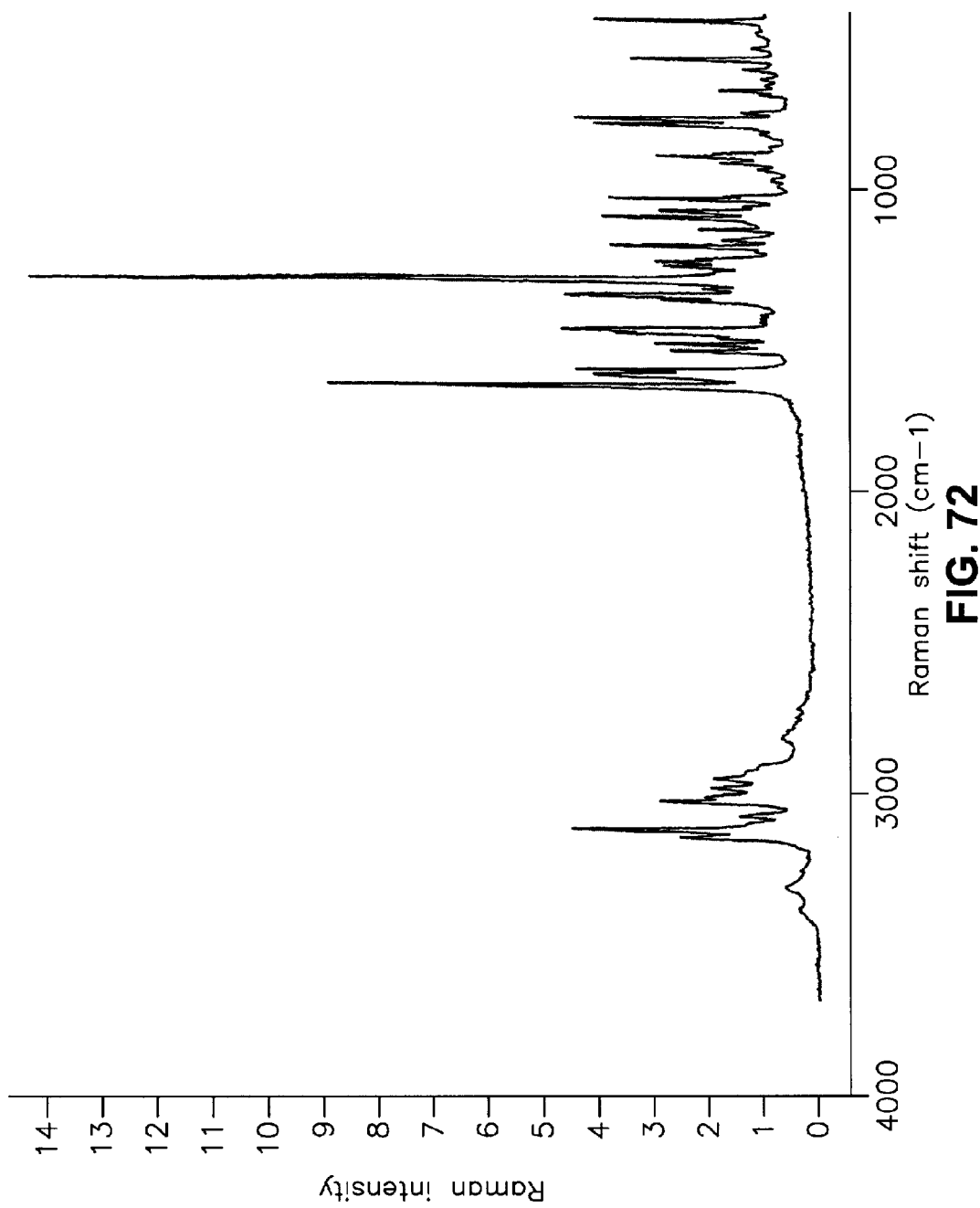
FIG. 72 is an FT-Raman spectrum for carvedilol hydrobromide ethanol solvate.
Figure 73:
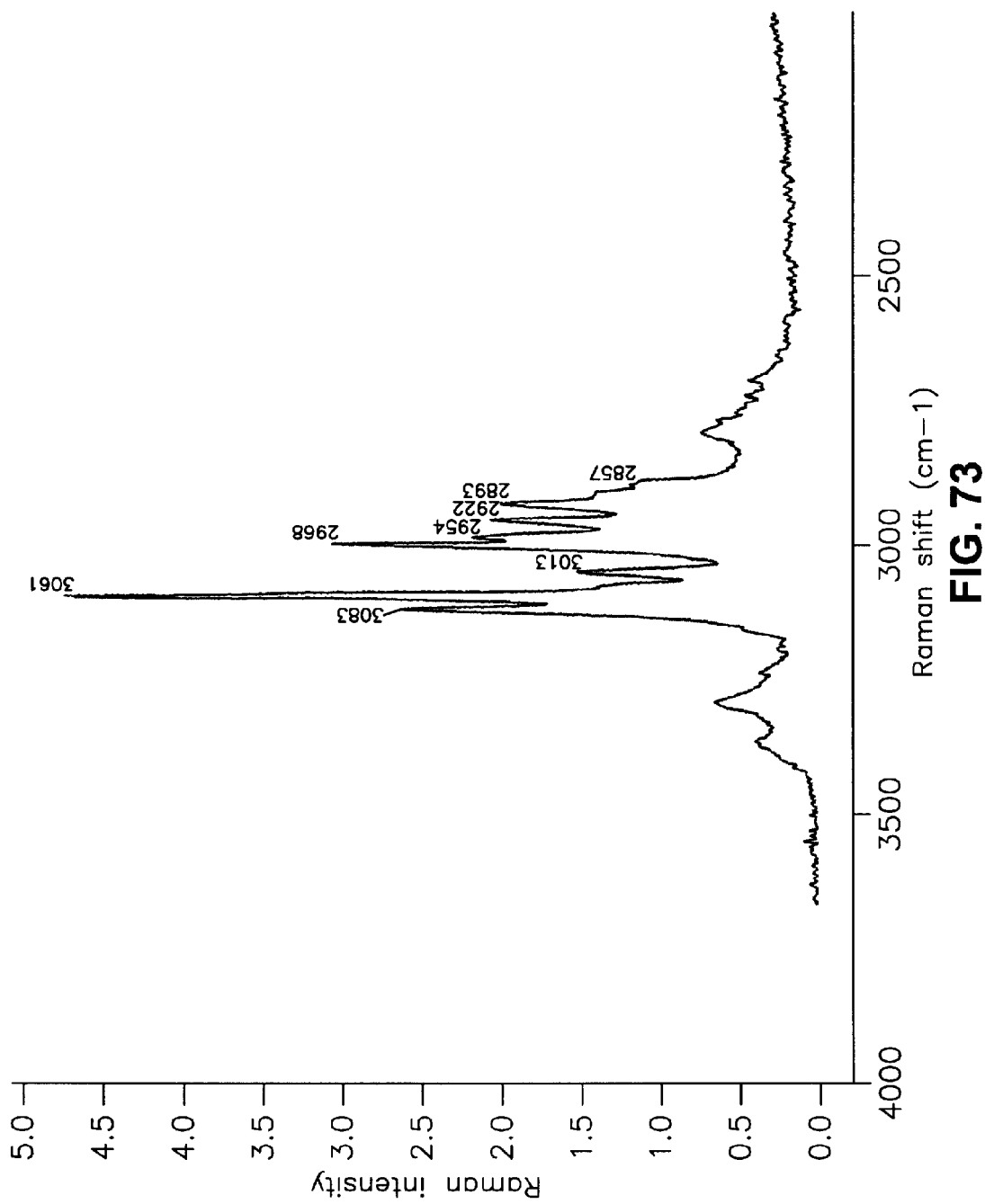
FIG. 73 is an FT-Raman spectrum for carvedilol hydrobromide ethanol solvate in the 4000-2000 cm$^{-1}$ region of the spectrum.
Figure 74:
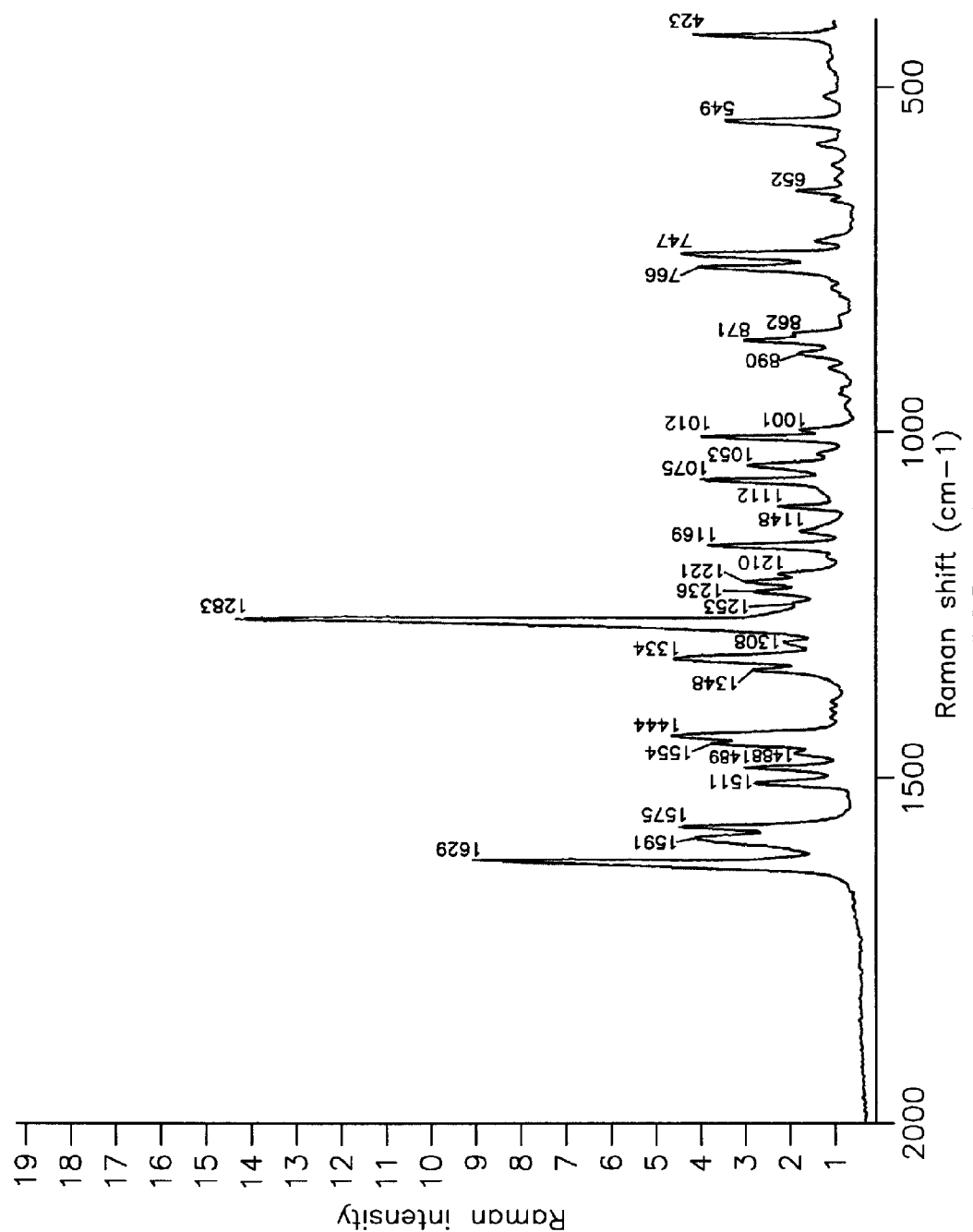
FIG. 74 is an FT-Raman spectrum for carvedilol hydrobromide ethanol solvate in the 2000-400 cm$^{-1}$ region of the spectrum.
Figure 75:
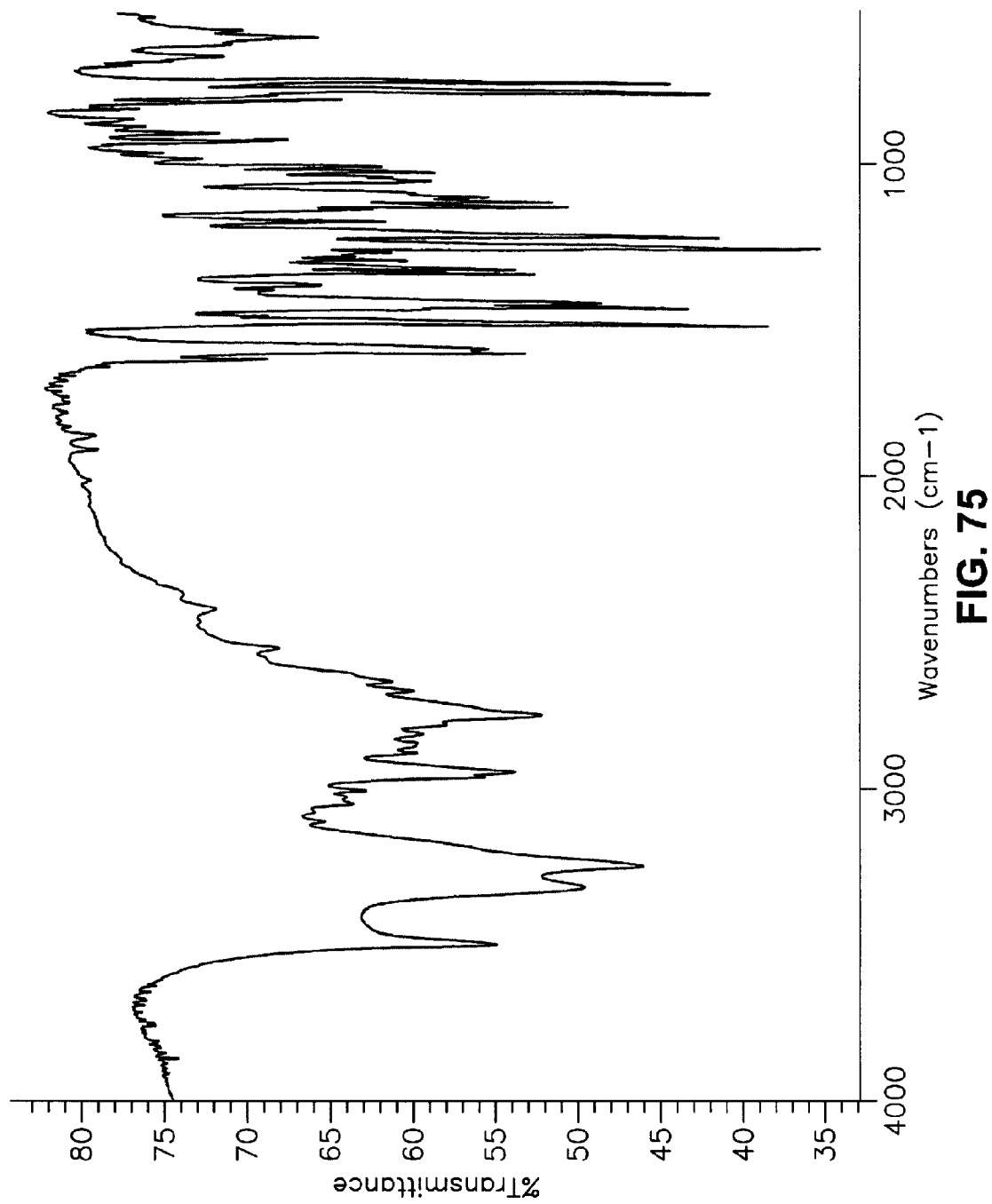
FIG. 75 is an FT-IR spectrum for carvedilol hydrobromide ethanol solvate.
Figure 76:
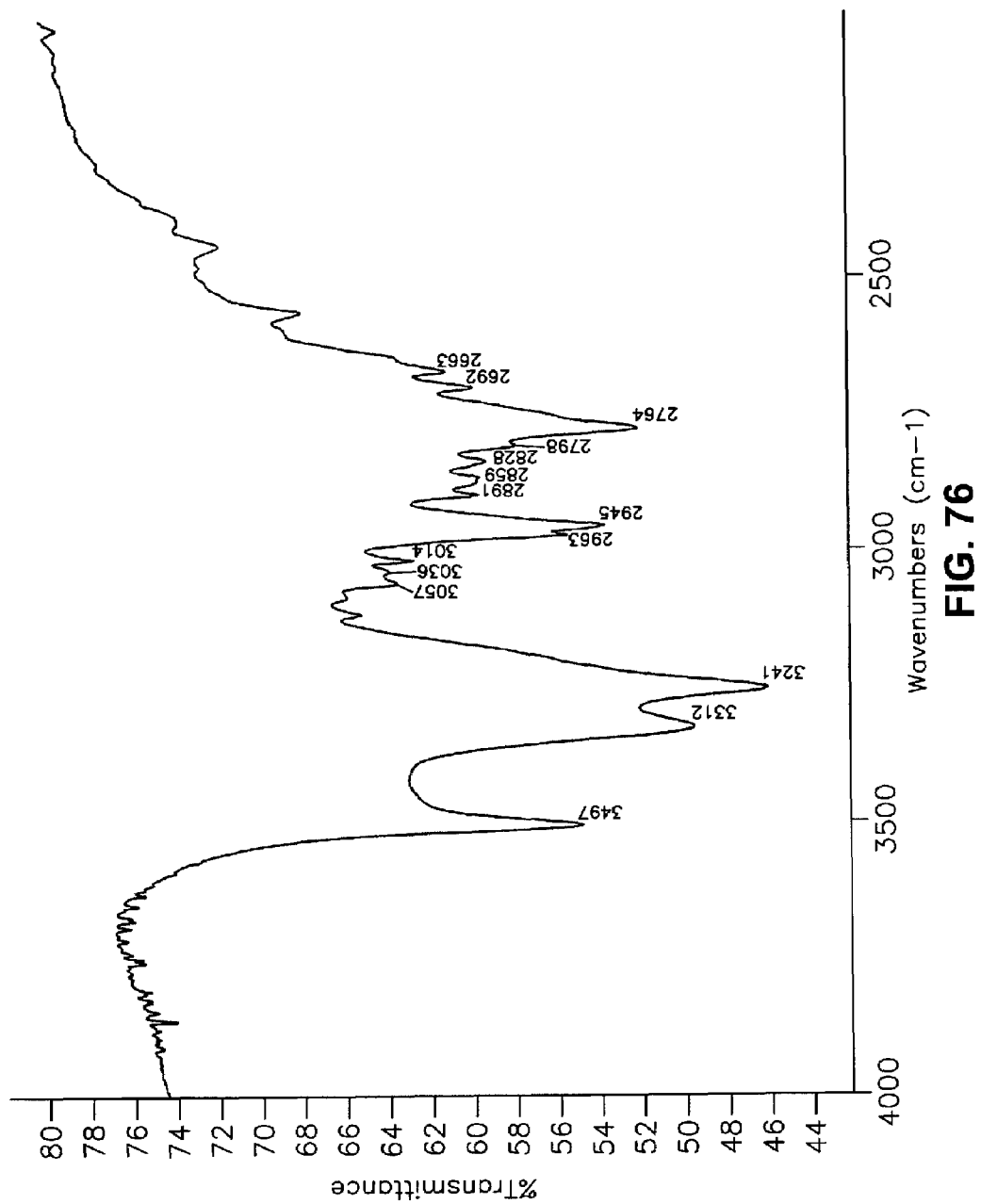
FIG. 76 is an FT-IR spectrum for carvedilol hydrobromide ethanol solvate in the 4000-2000 cm$^{-1}$ region of the spectrum.
Figure 77:
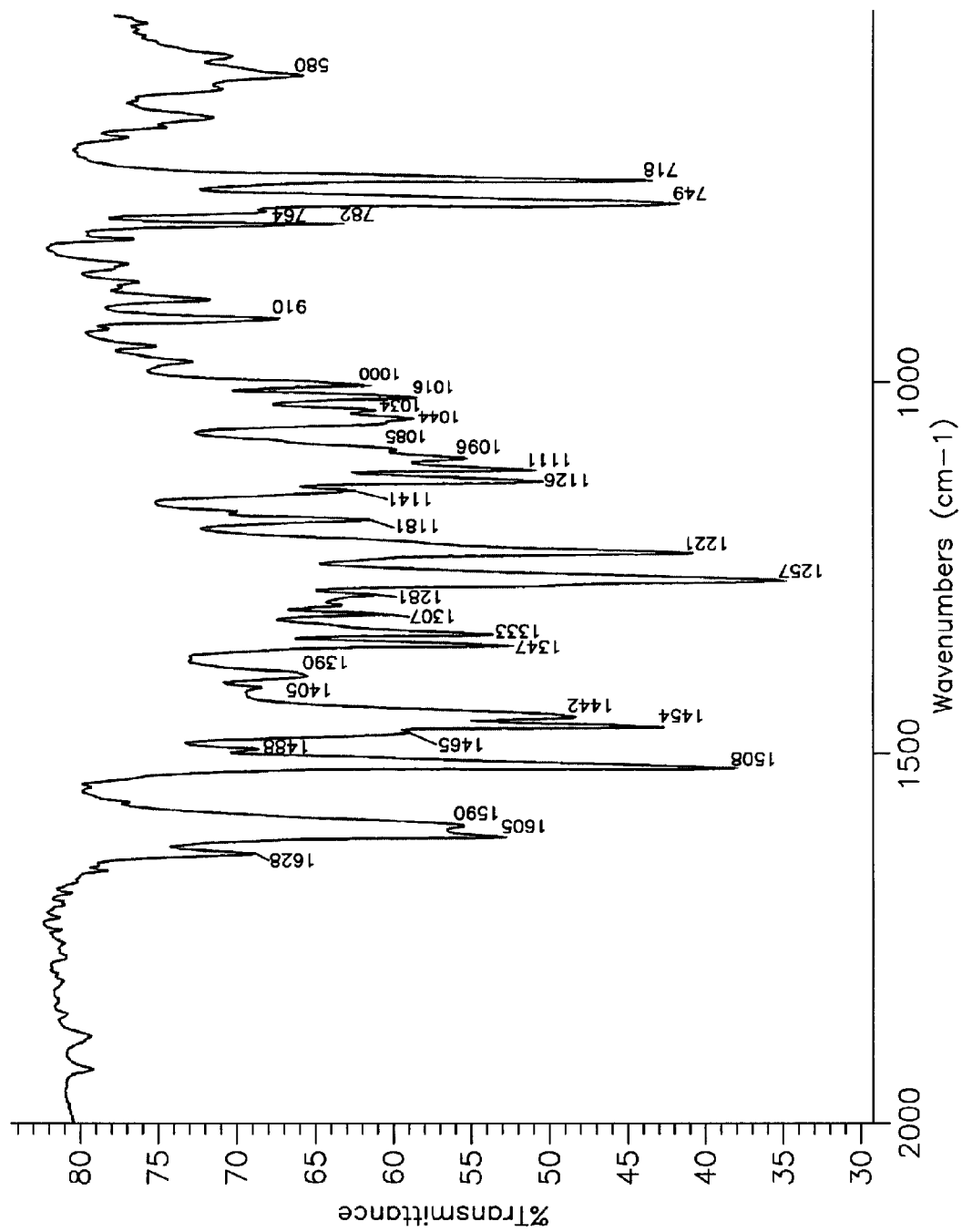
FIG. 77 is an FT-IR spectrum for carvedilol hydrobromide ethanol solvate in the 2000-500 cm$^{-1}$ region of the spectrum.

Crystalline carvedilol hydrobromide ethanol solvate (see, Example 10: Form 10) also is identified by an x-ray diffraction pattern as shown substantially in FIG. 70, which depicts characteristic peaks in degrees two-theta (2θ): i.e., 8.1±0.2 (2θ), 8.6±0.2 (2θ), 13.2±0.2 (2θ), 17.4±0.2 (2θ), 18.6±0.2 (2θ), 21.8±0.2 (2θ), 23.2±0.2 (2θ), 23.7±0.2 (2θ), and 27.4±0.2 (2θ).

Figure 6:
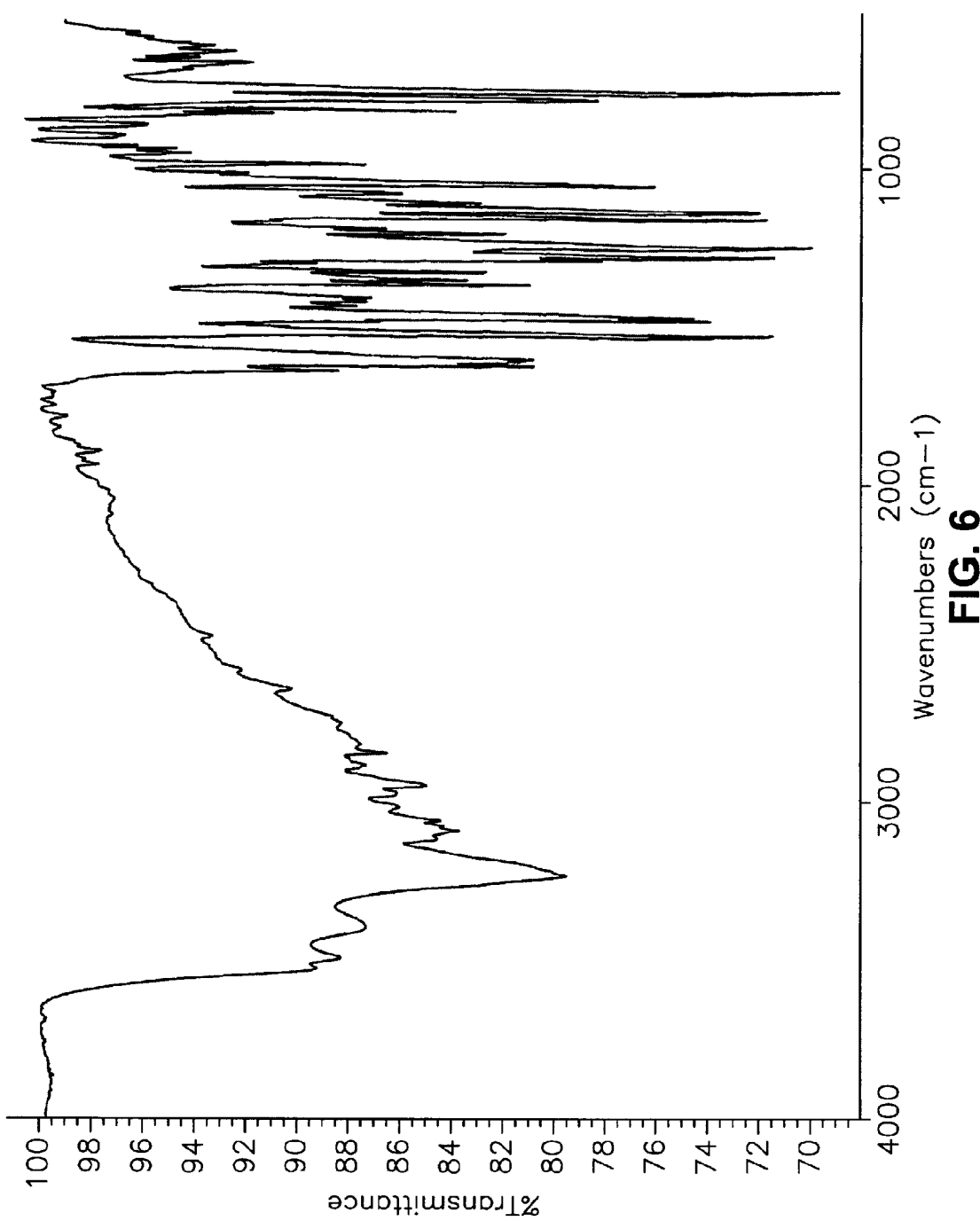
FIG. 6 is an FT-IR spectrum for carvedilol hydrobromide monohydrate.
Figure 7:
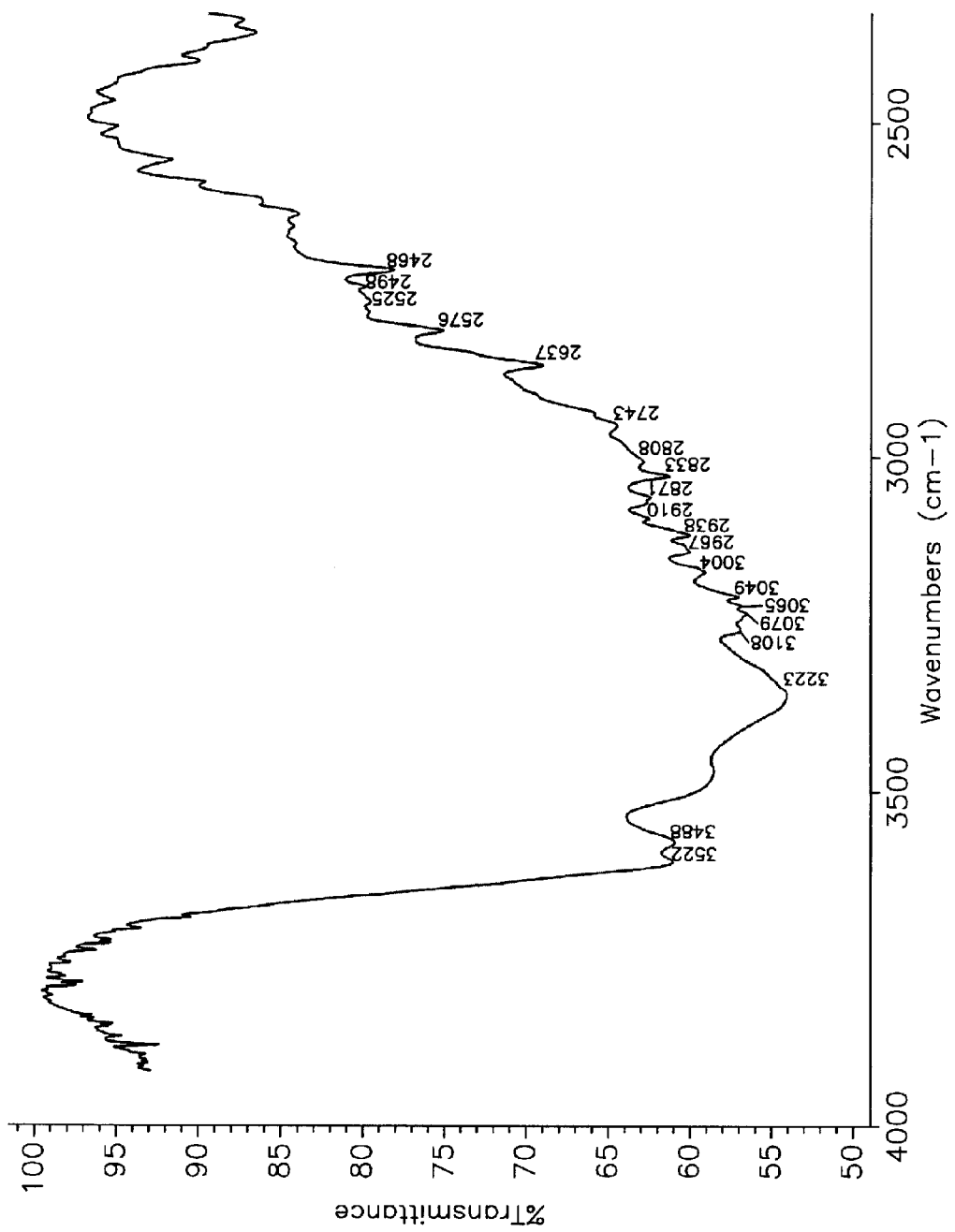
FIG. 7 is an FT-IR spectrum for carvedilol hydrobromide monohydrate in the 4000-2000 $cm^{-1}$ region of the spectrum.
Figure 8:
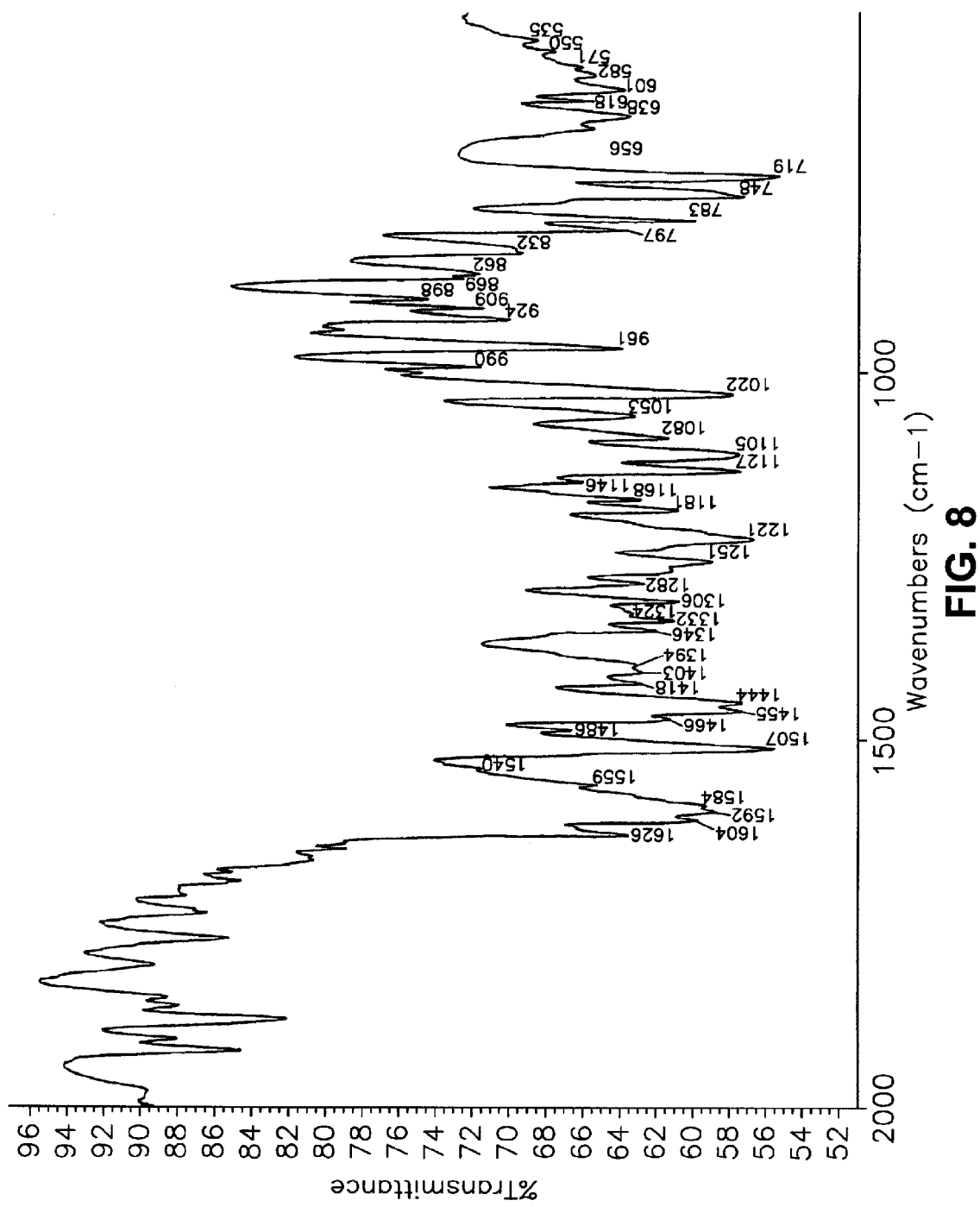
FIG. 8 is an FT-IR spectrum for carvedilol hydrobromide monohydrate in the 2000-500 $cm^{-1}$ region of the spectrum.
Figure 9:
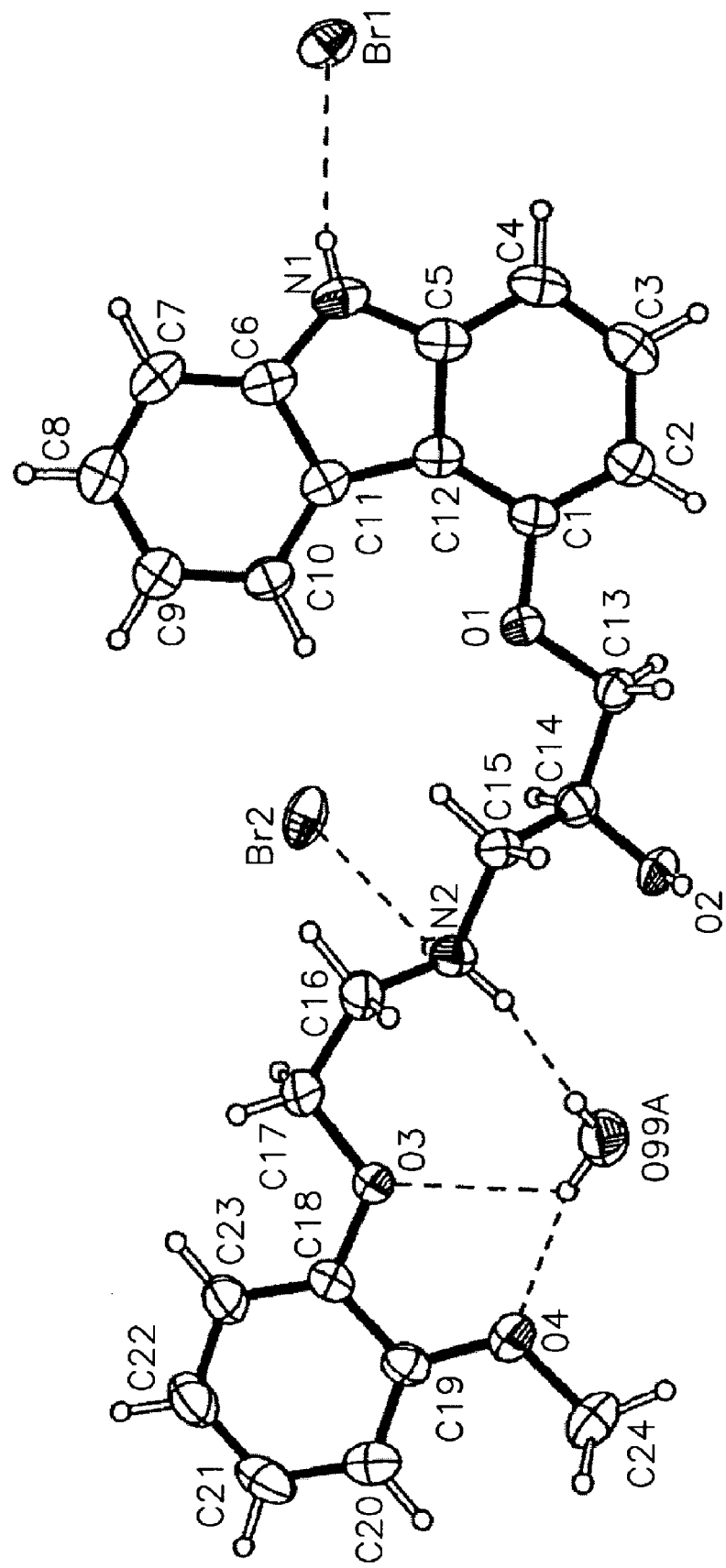
FIG. 9 is a view of a single molecule of carvedilol hydrobromide monohydrate. The hydroxyl group and the water molecule are disordered.
Figure 10:
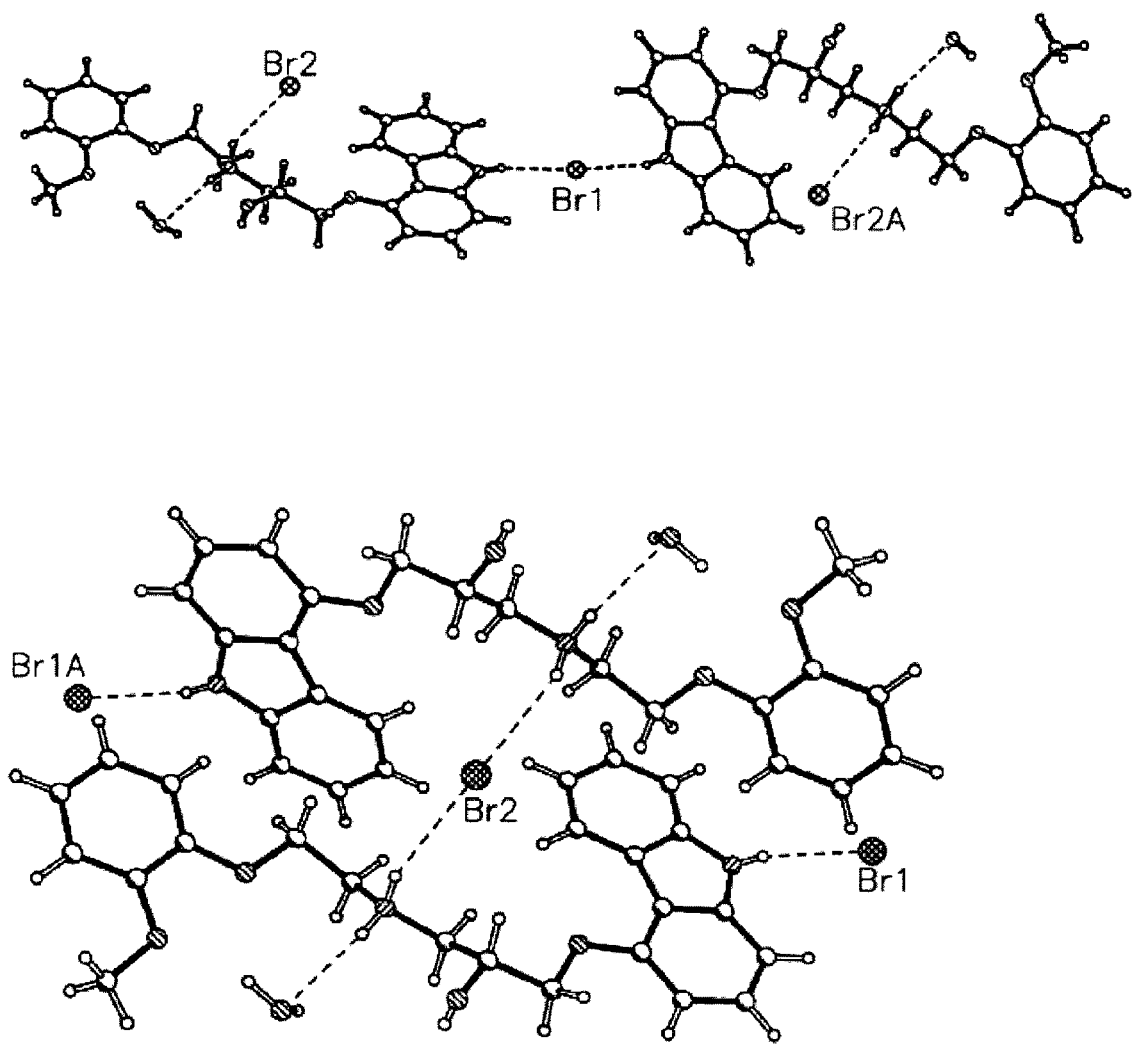
FIG. 10 are views of molecules of carvedilol hydrobromide monohydrate showing the N—H...Br...H—N interactions. The top view focuses on Br1 and the bottom view focuses on Br2. The interaction between the carvedilol cation and the bromine anion is unusual. Each carvedilol molecule makes two chemically different contacts to the bromine anions. Each bromine anion sits on a crystallographic special position (that is, on a crystallographic two-fold axis) which means that there are two half bromine anions interacting with each carvedilol cation.
Figure 11:
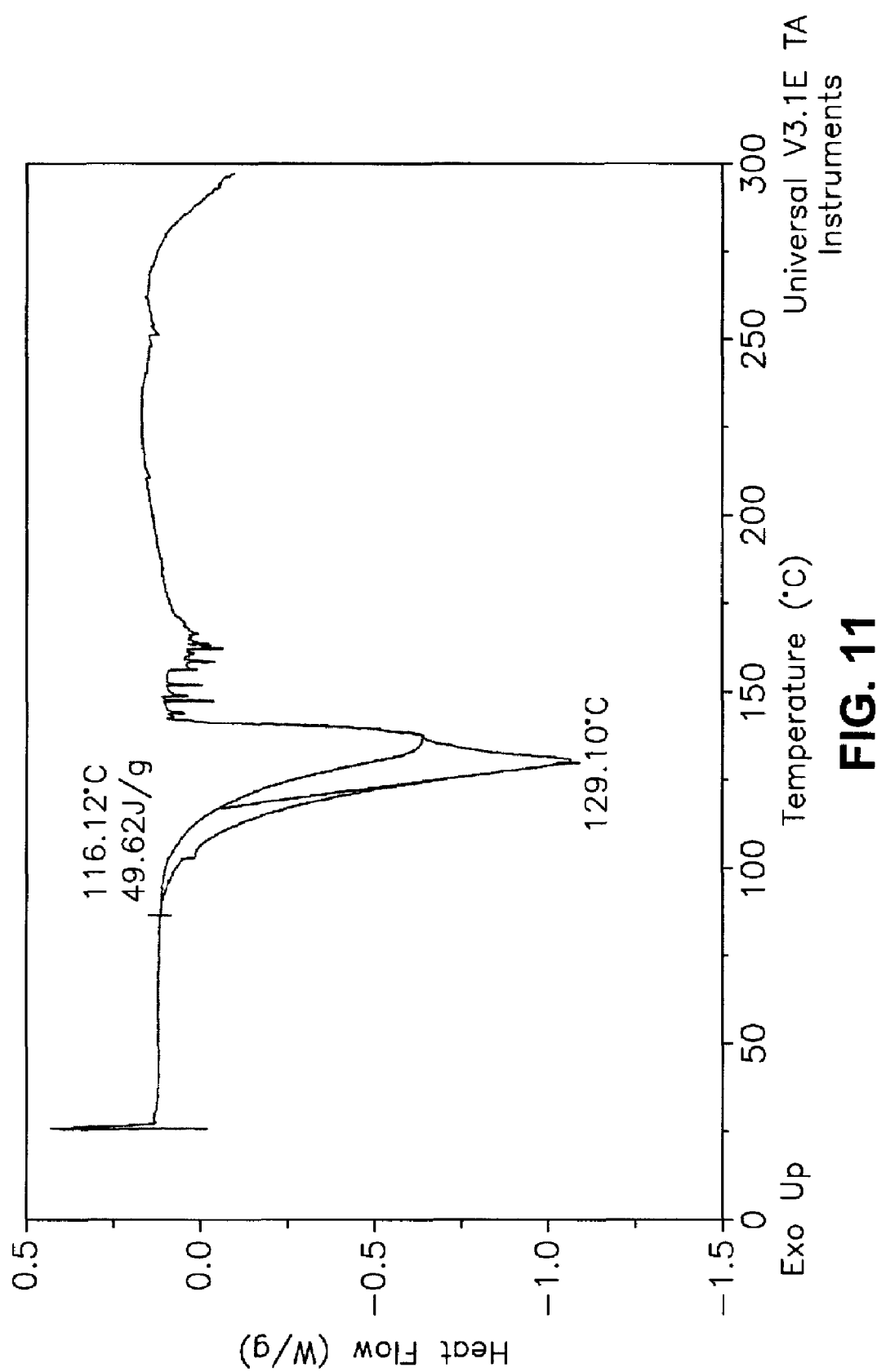
FIG. 11 is a differential scanning calorimetry thermogram for carvedilol hydrobromide dioxane solvate.
Figure 12:
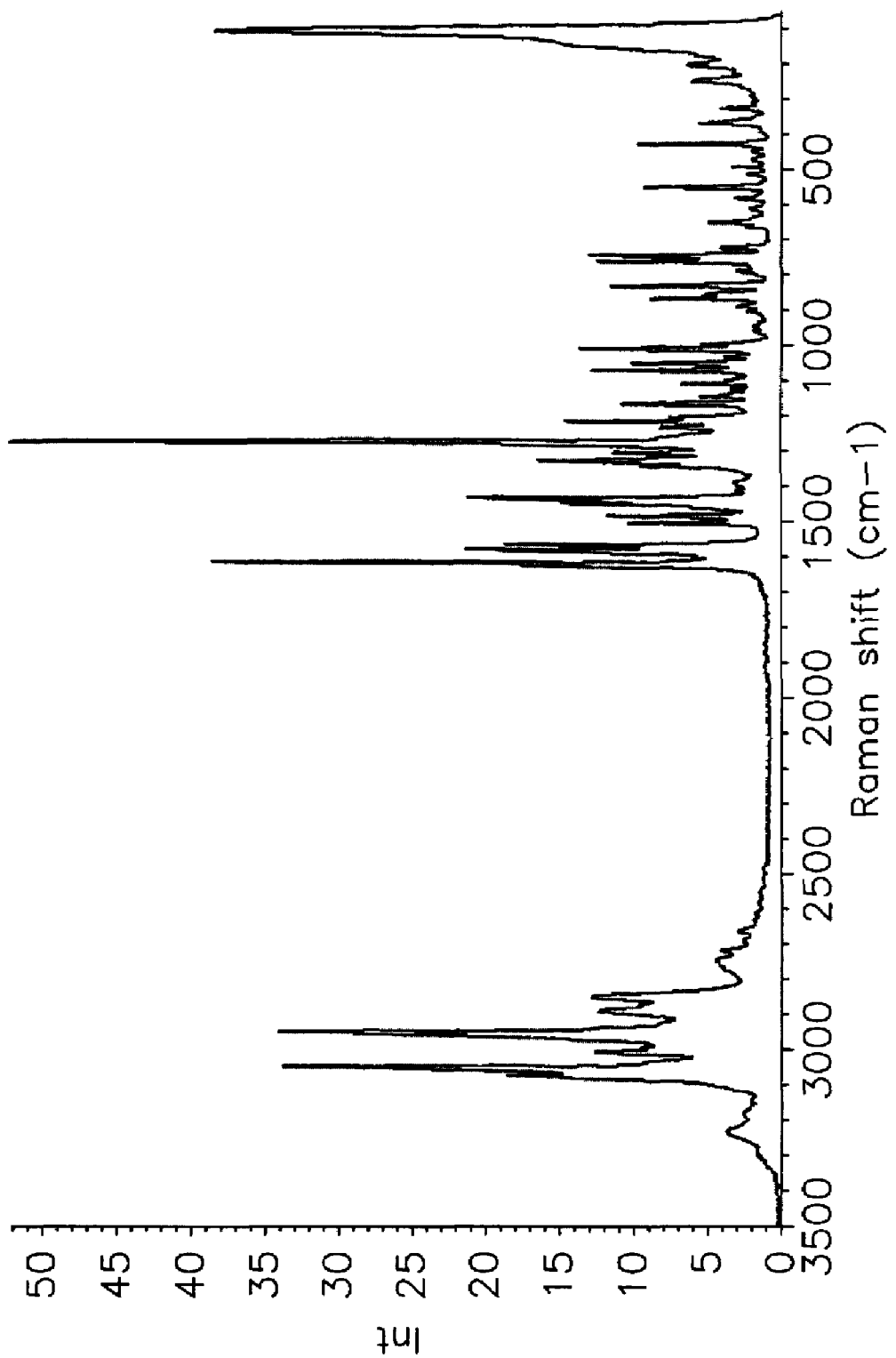
FIG. 12 is an FT-Raman spectrum for carvedilol hydrobromide dioxane solvate.
Figure 13:
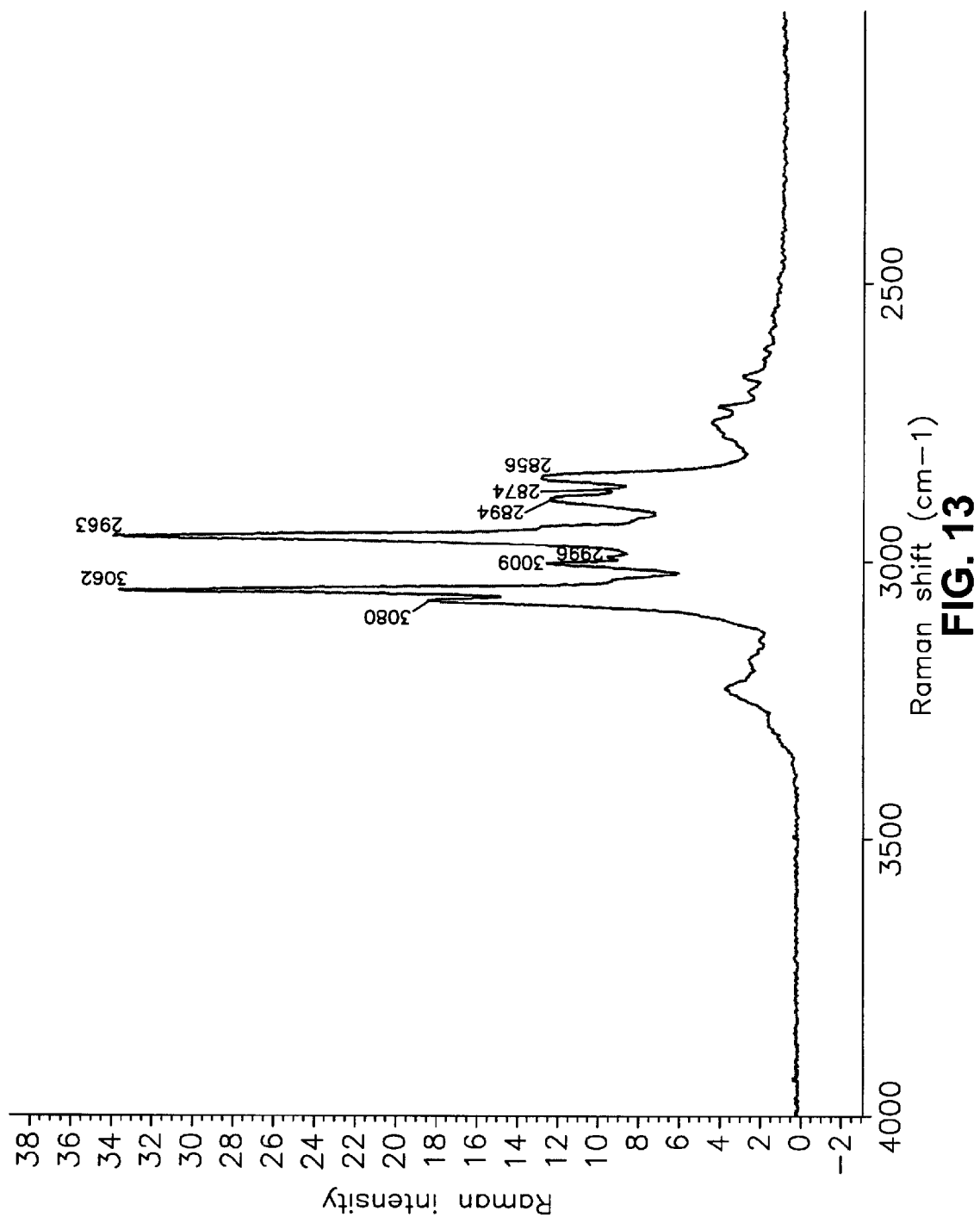
FIG. 13 is an FT-Raman spectrum for carvedilol hydrobromide dioxane solvate in the 4000-2000 $cm^{-1}$ region of the spectrum.
Figure 14:
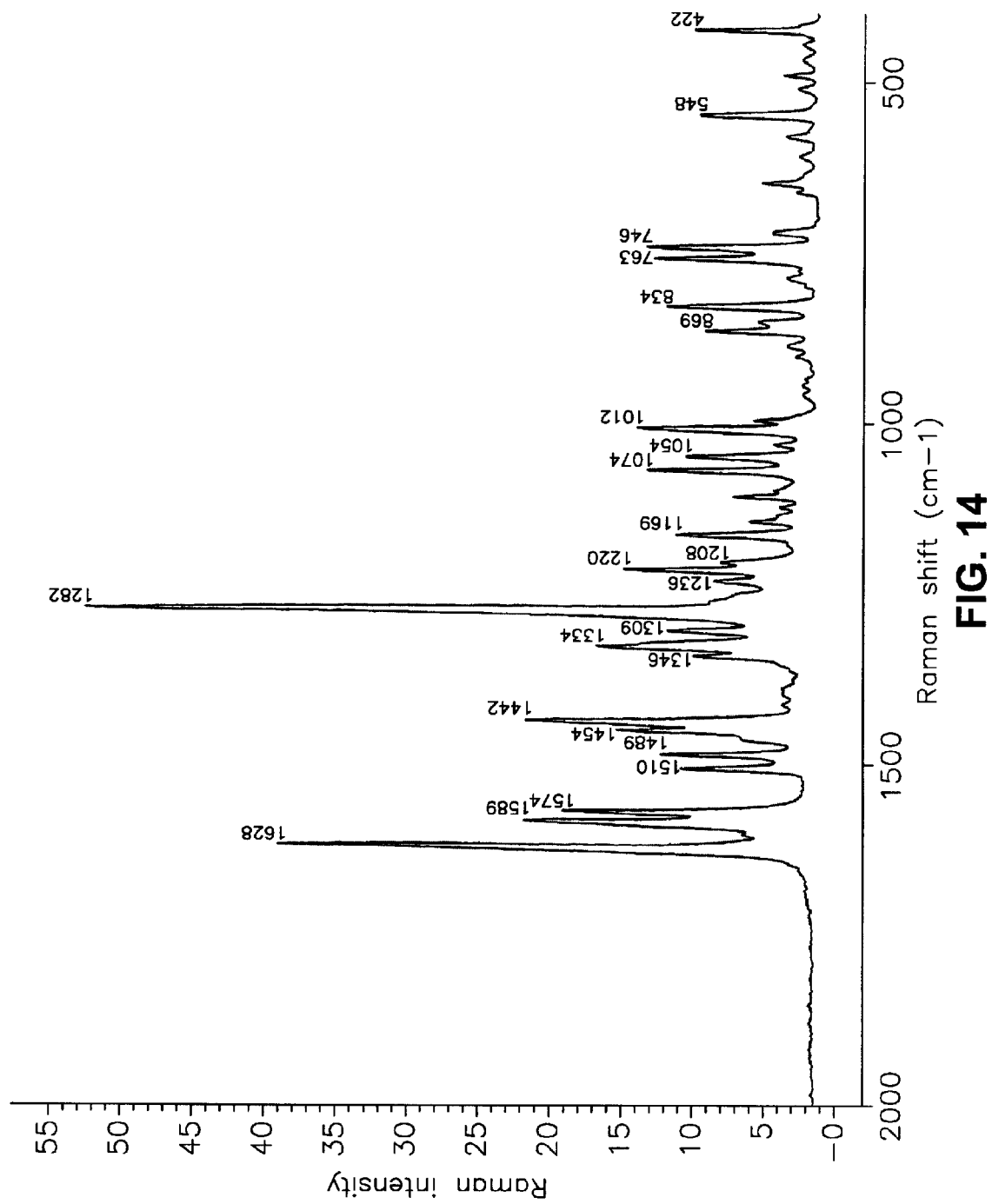
FIG. 14 is an FT-Raman spectrum for carvedilol hydrobromide dioxane solvate in the 2000-400 $cm^{-1}$ region of the spectrum.
Figure 15:
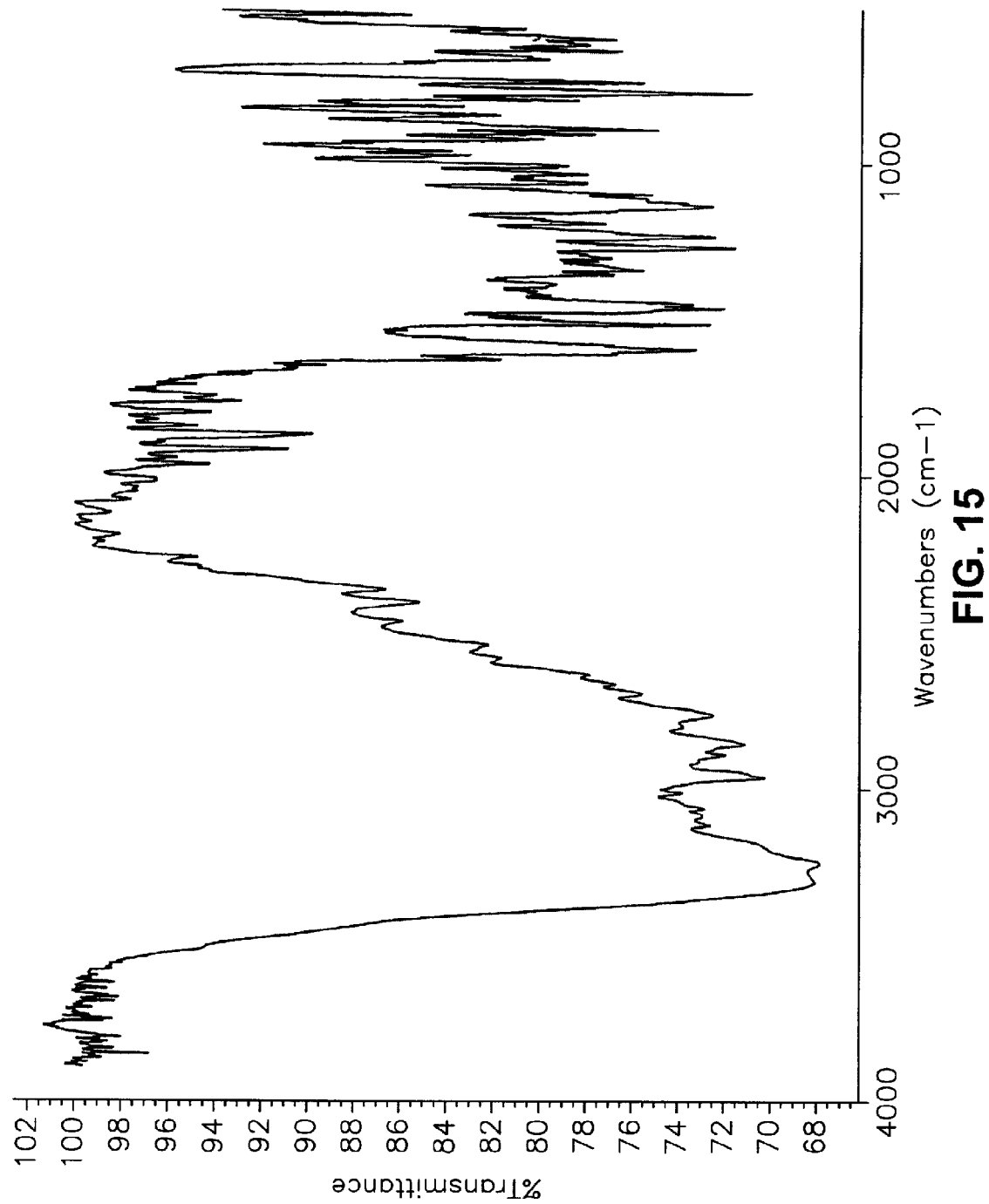
FIG. 15 is an FT-IR spectrum for carvedilol hydrobromide dioxane solvate.
Figure 16:
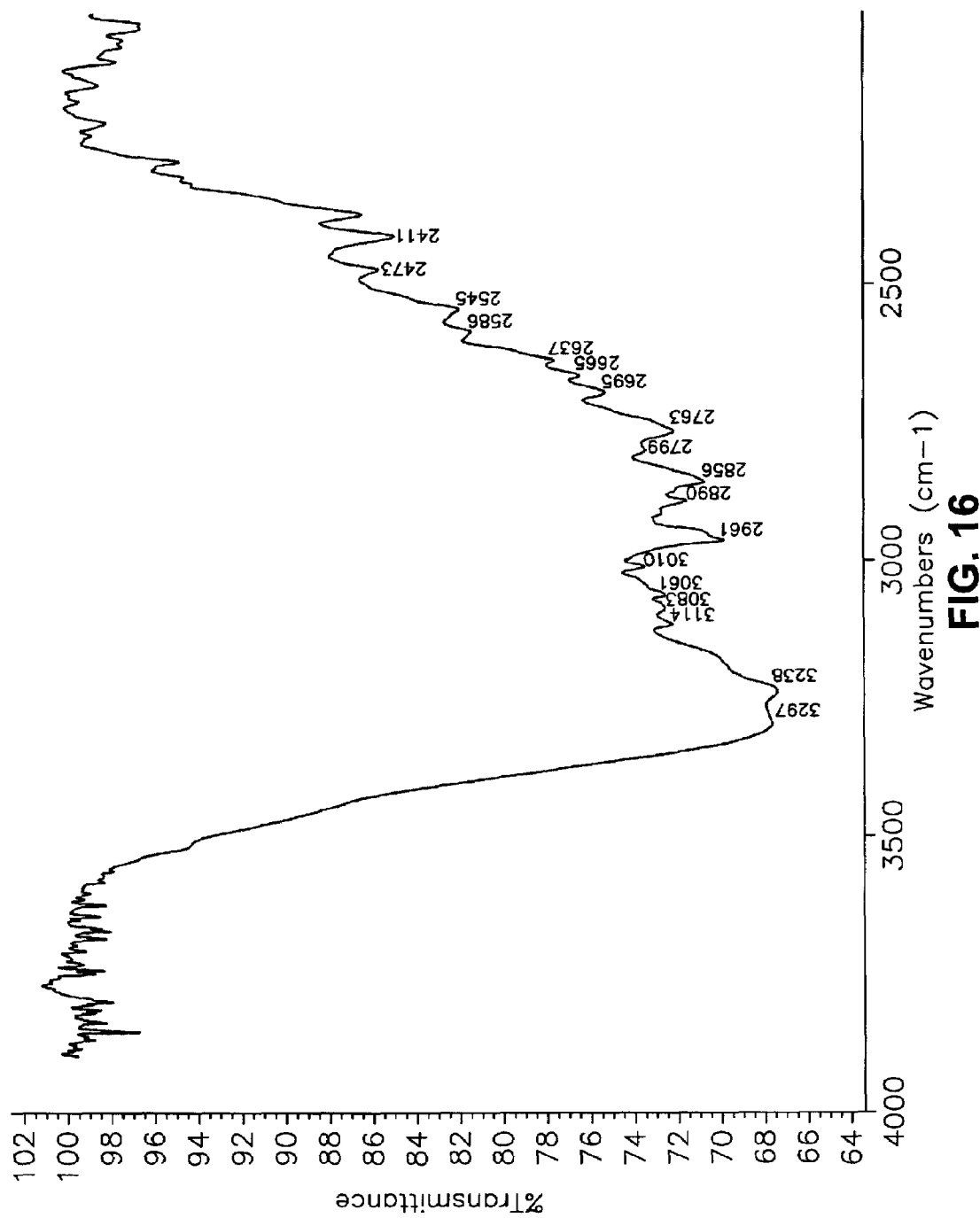
FIG. 16 is an FT-IR spectrum for carvedilol hydrobromide dioxane solvate in the 4000-2000 $cm^{-1}$ region of the spectrum.
Figure 17:
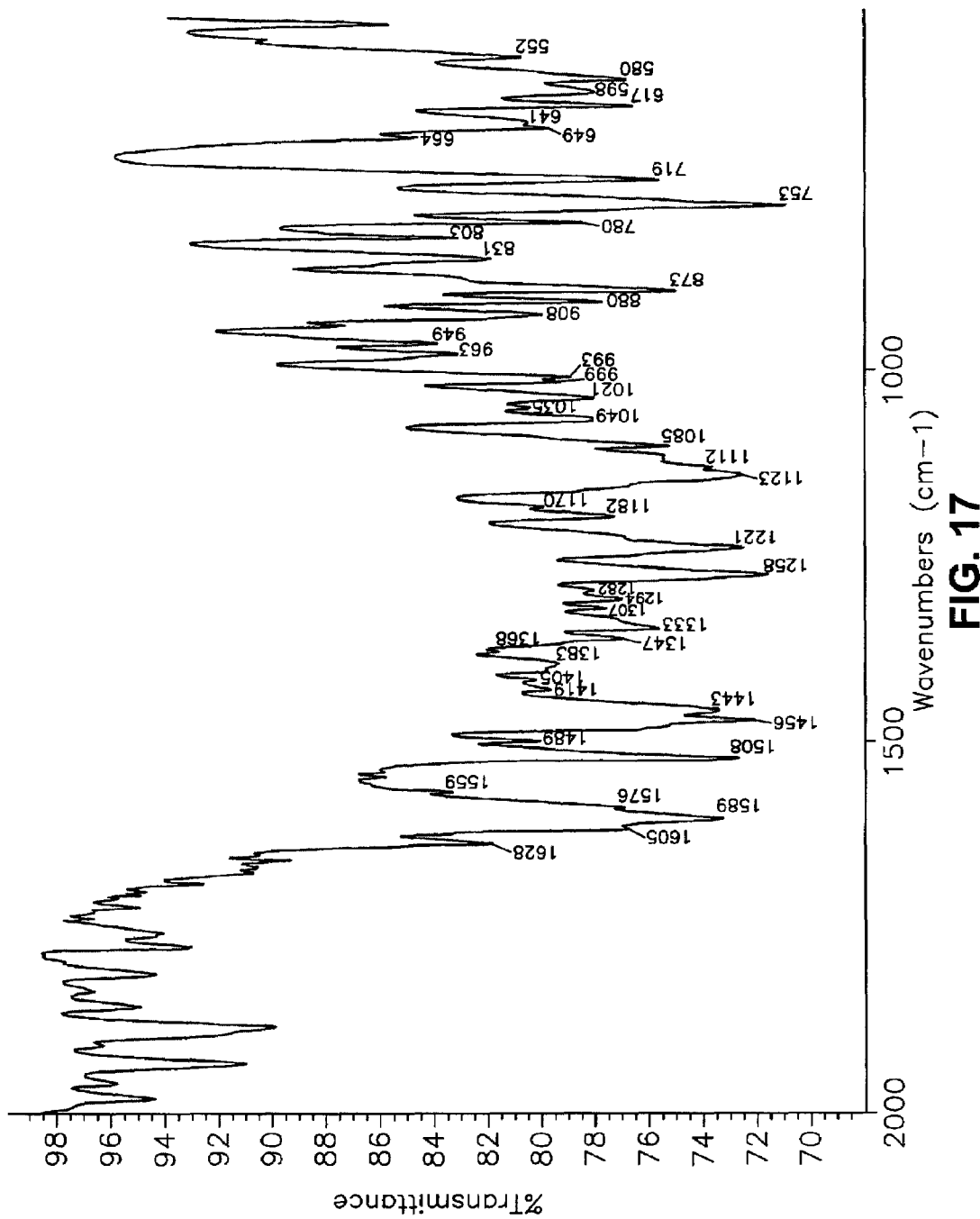
FIG. 17 is an FT-IR spectrum for carvedilol hydrobromide dioxane solvate in the 2000-500 $cm^{-1}$ region of the spectrum.
Figure 18:
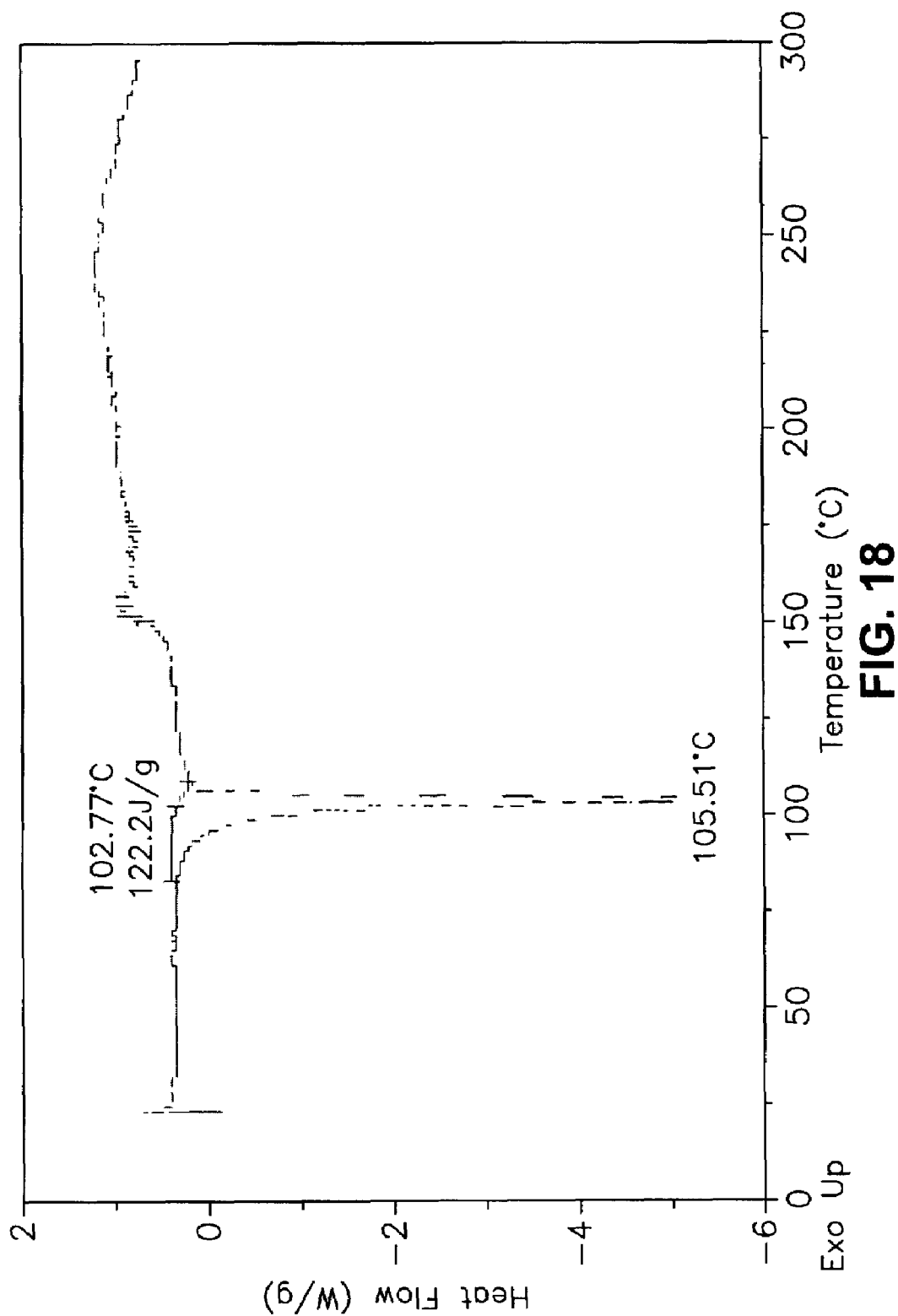
FIG. 18 is a differential scanning calorimetry thermogram for carvedilol hydrobromide 1-pentanol solvate.
Figure 19:
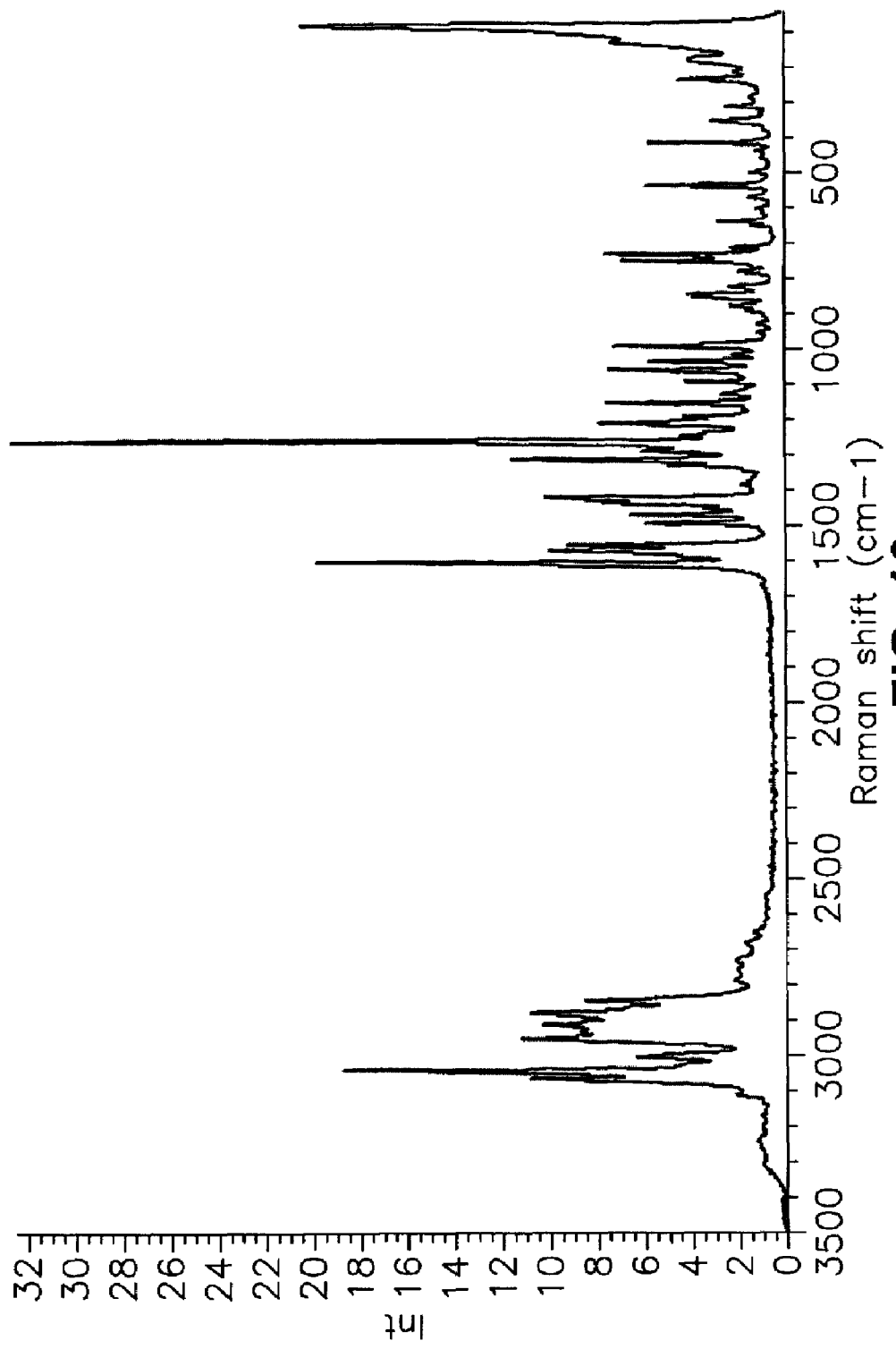
FIG. 19 is an FT-Raman spectrum for carvedilol hydrobromide 1-pentanol solvate.
Figure 20:
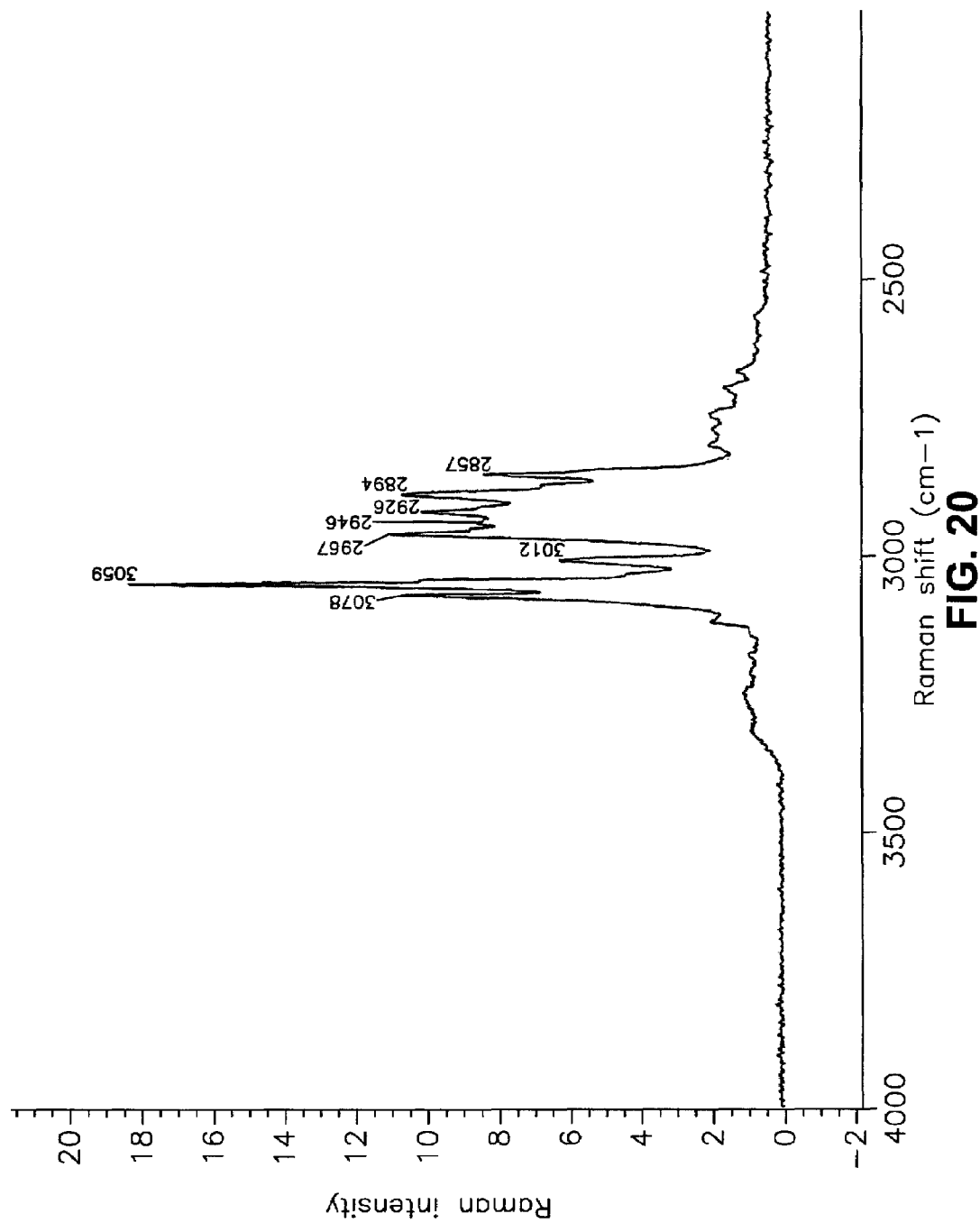
FIG. 20 is an FT-Raman spectrum for carvedilol hydrobromide 1-pentanol solvate in the 4000-2000 $cm^{-1}$ region of the spectrum.
Figure 21:
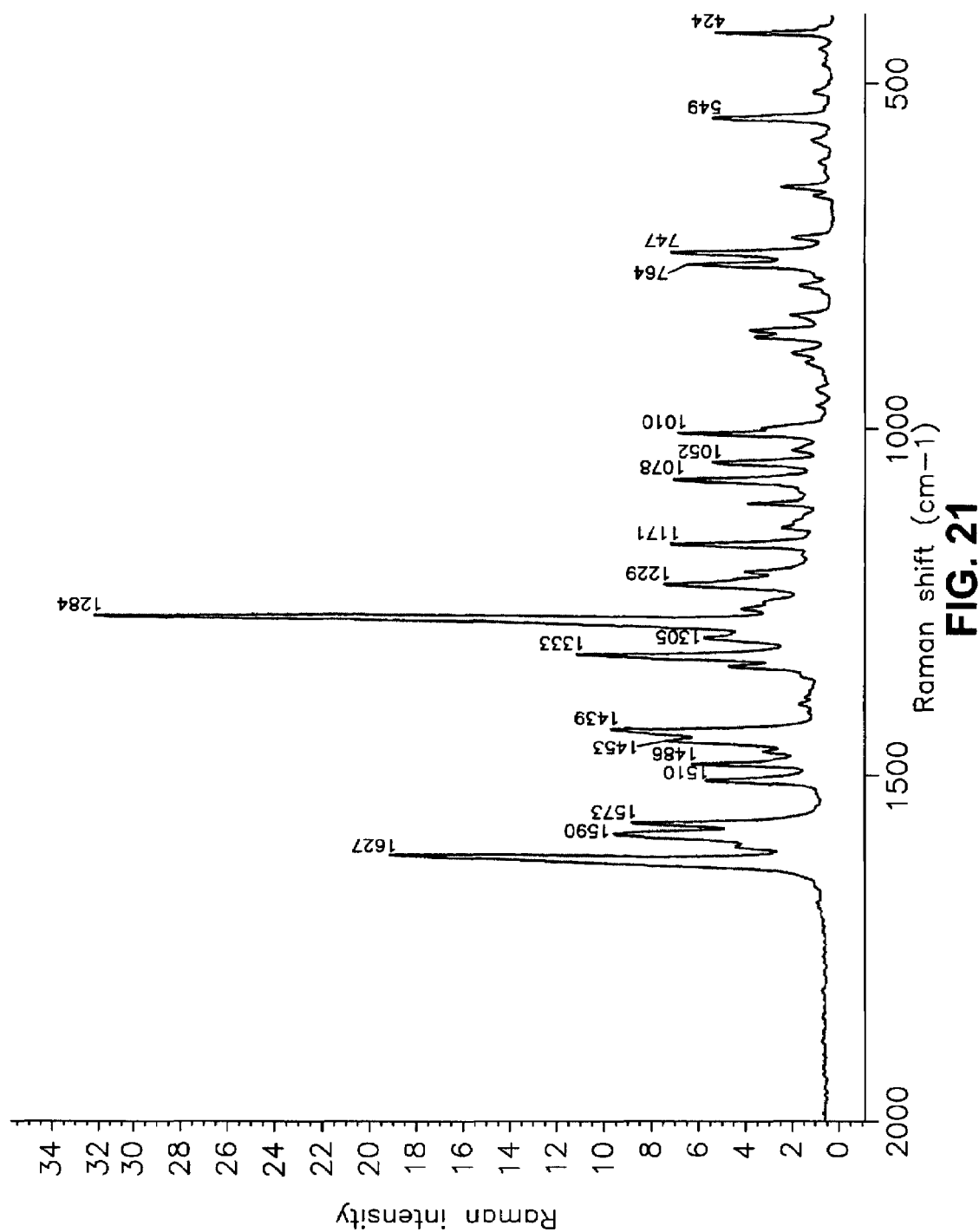
FIG. 21 is an FT-Raman spectrum for carvedilol hydrobromide 1-pentanol solvate in the 2000-400 $cm^{-1}$ region of the spectrum.
Figure 22:
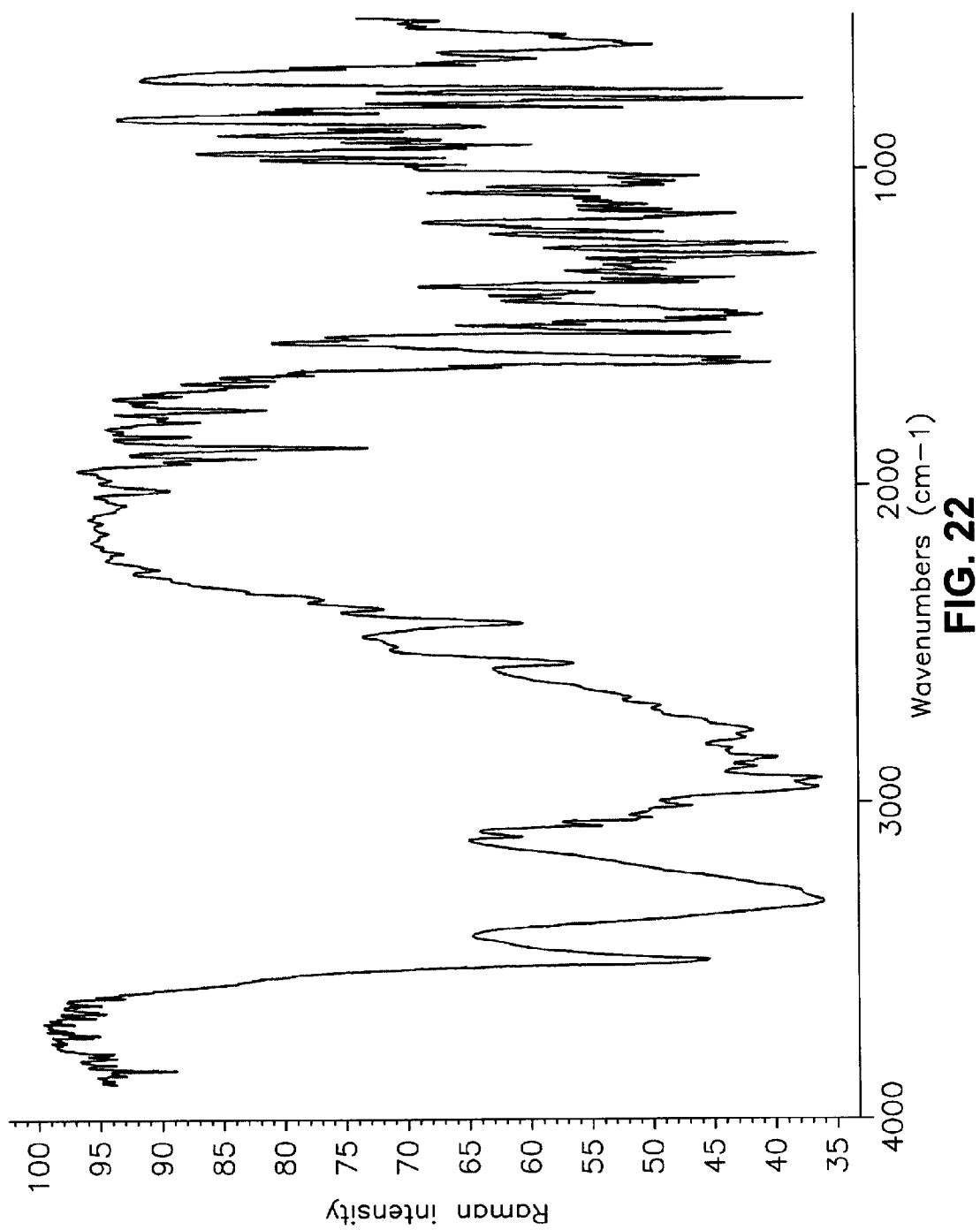
FIG. 22 is an FT-IR spectrum for carvedilol hydrobromide 1-pentanol solvate.
Figure 23:
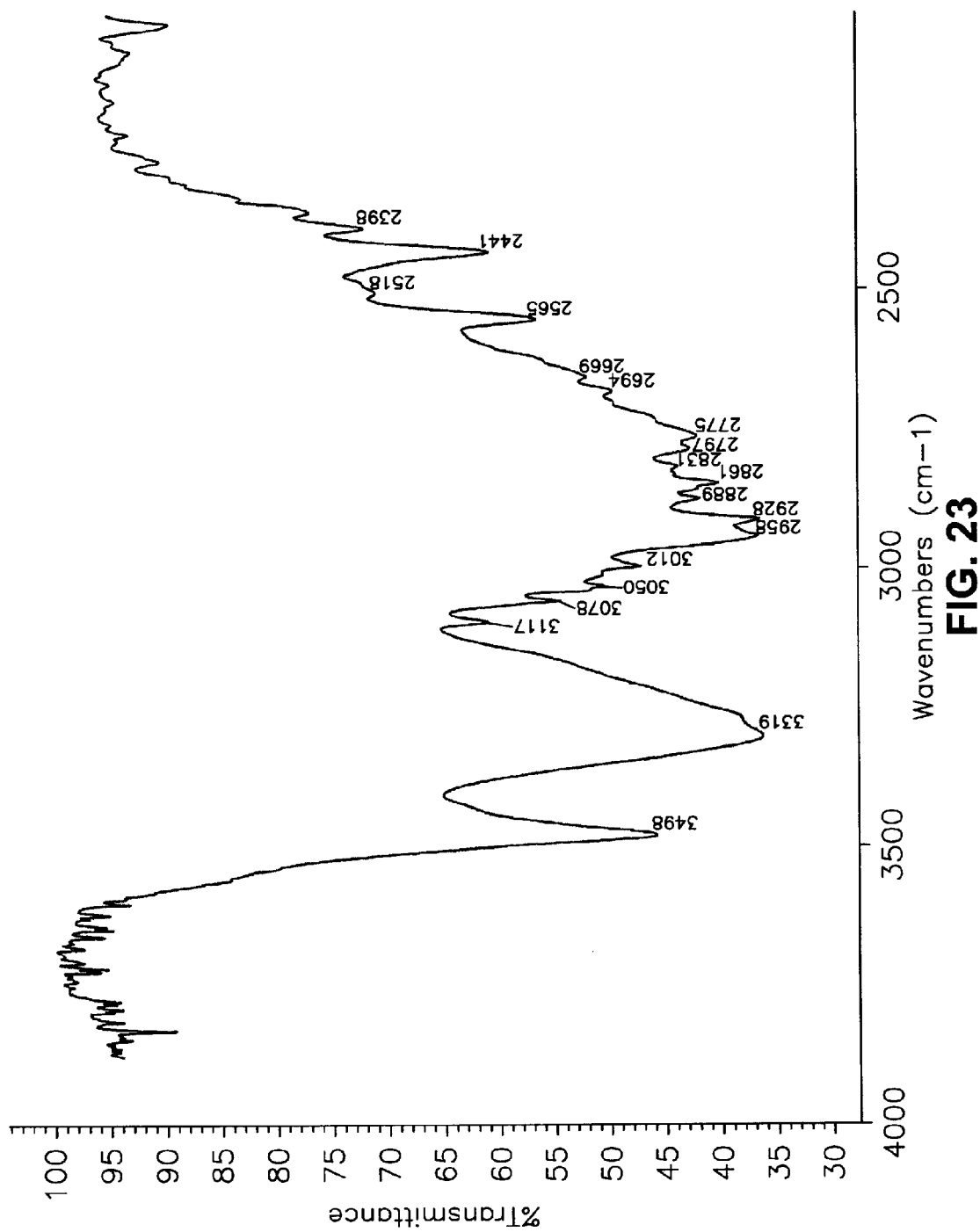
FIG. 23 is an FT-IR spectrum for carvedilol hydrobromide 1-pentanol solvate in the 4000-2000 $cm^{-1}$ region of the spectrum.
Figure 24:
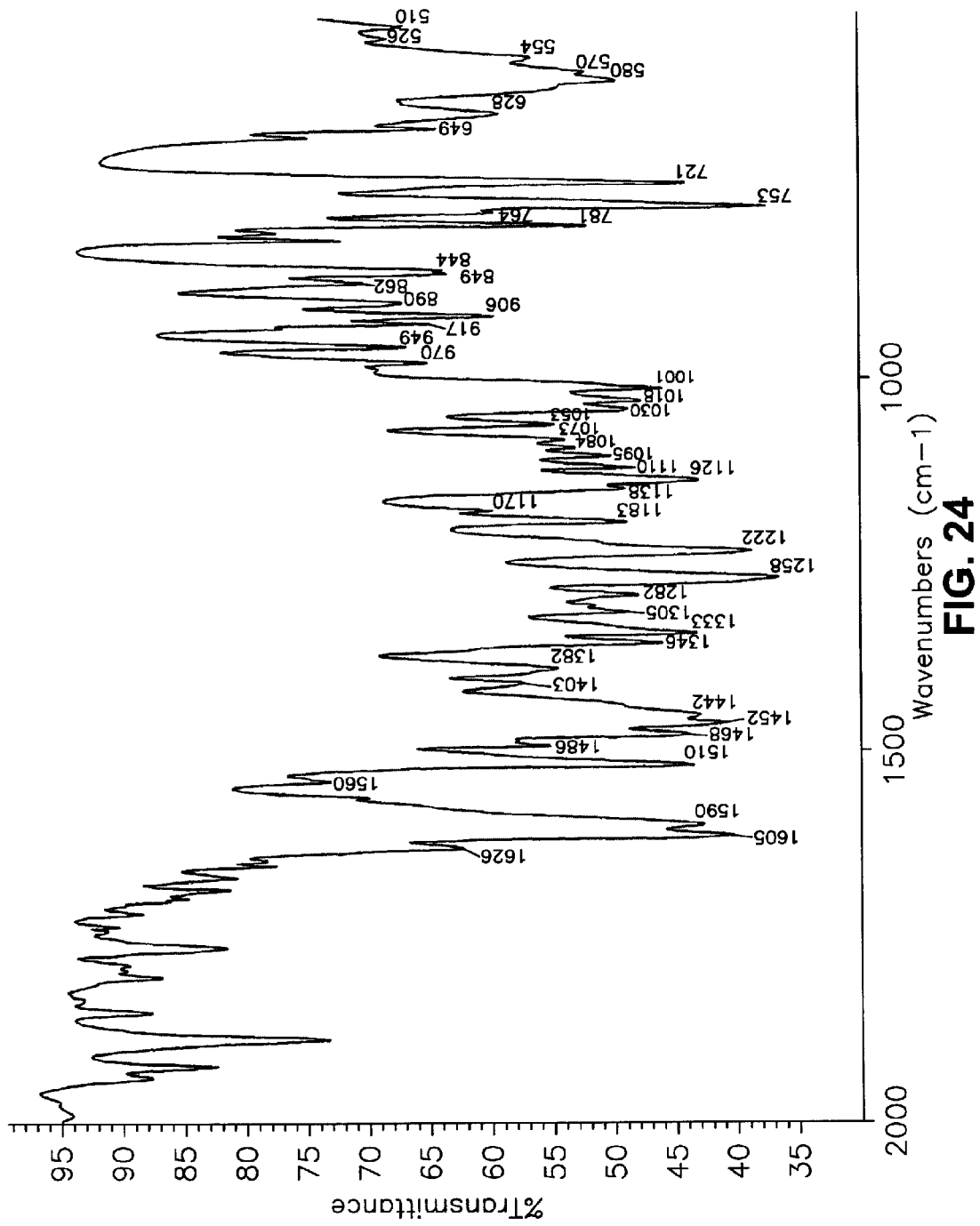
FIG. 24 is an FT-IR spectrum for carvedilol hydrobromide 1-pentanol solvate in the 2000-500 $cm^{-1}$ region of the spectrum.
Figure 25:
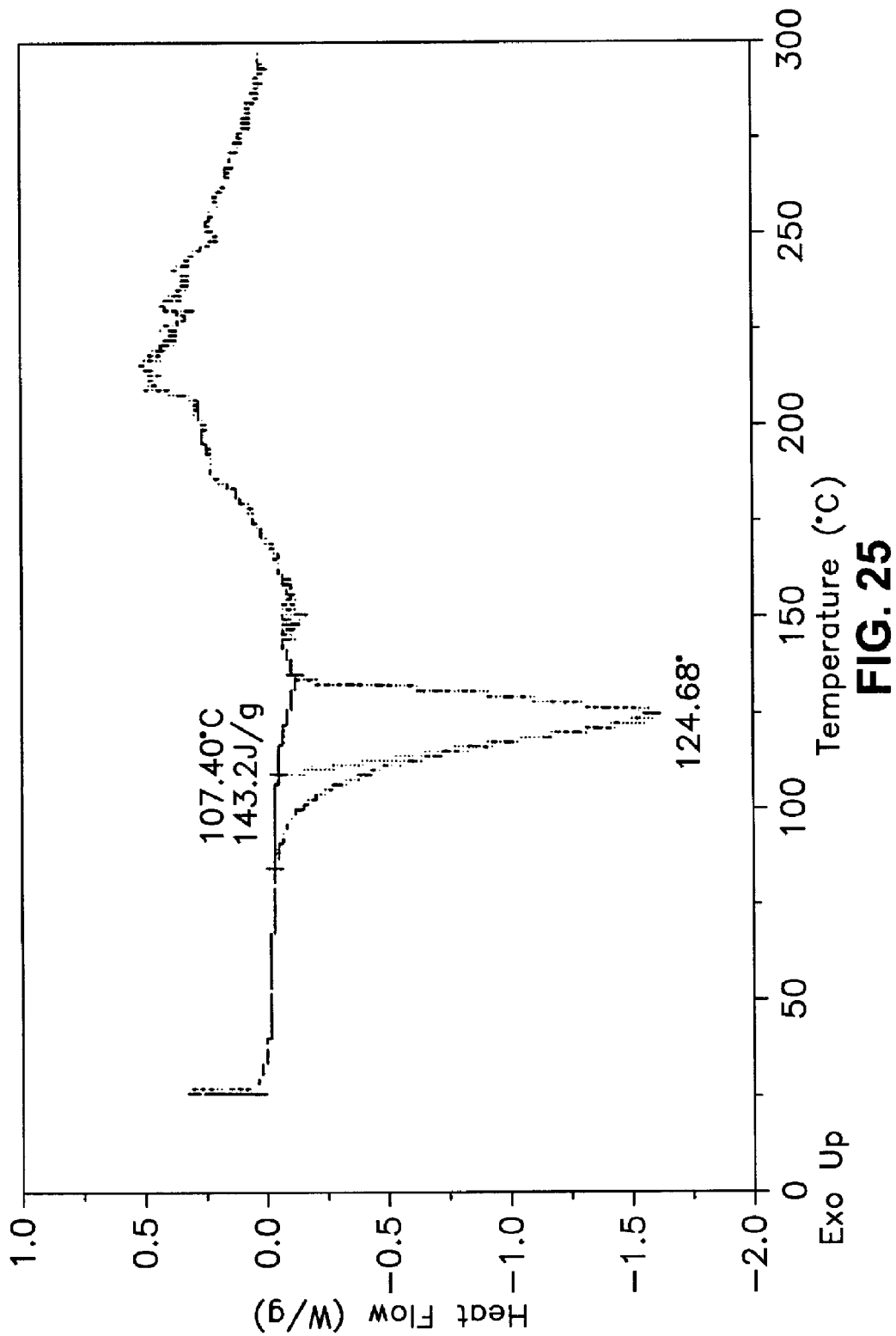
FIG. 25 is a differential scanning calorimetry thermogram for carvedilol hydrobromide 2-methyl-1-propanol solvate.
Figure 26:
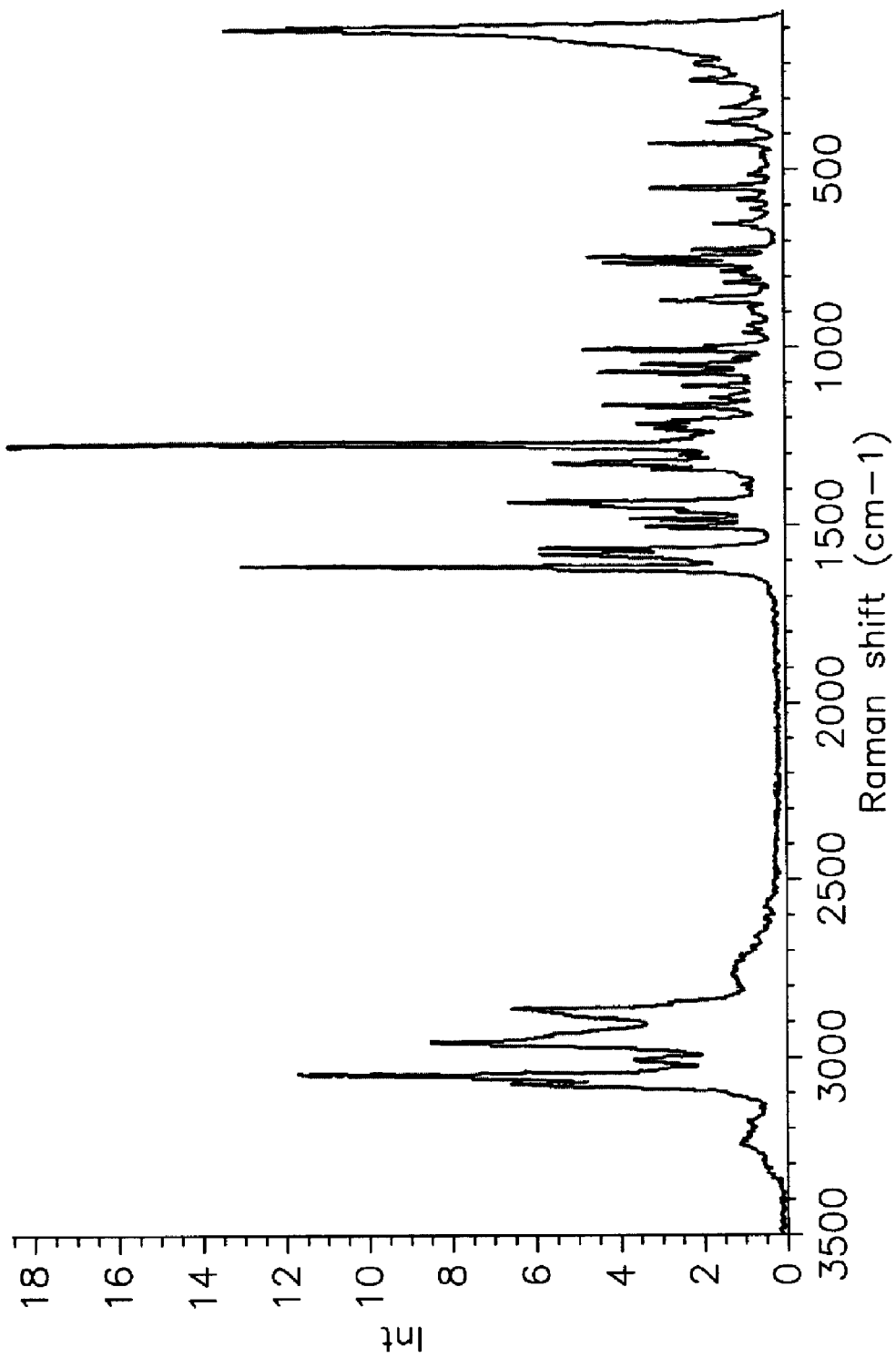
FIG. 26 is an FT-Raman spectrum for carvedilol hydrobromide 2-methyl-1-propanol solvate.
Figure 27:
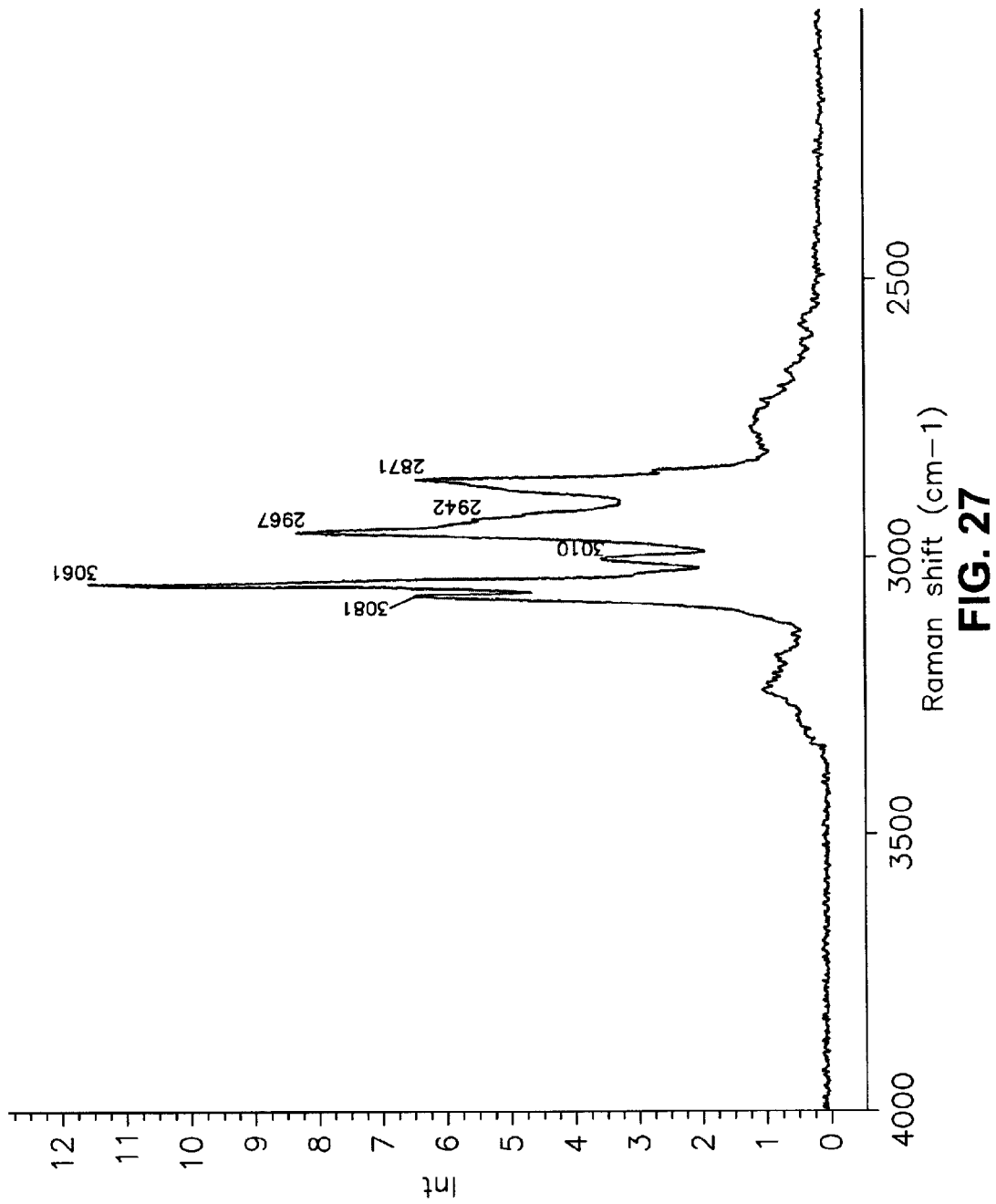
FIG. 27 is an FT-Raman spectrum for carvedilol hydrobromide 2-methyl-1-propanol solvate in the 4000-2000 $cm^{-1}$ region of the spectrum.
Figure 28:
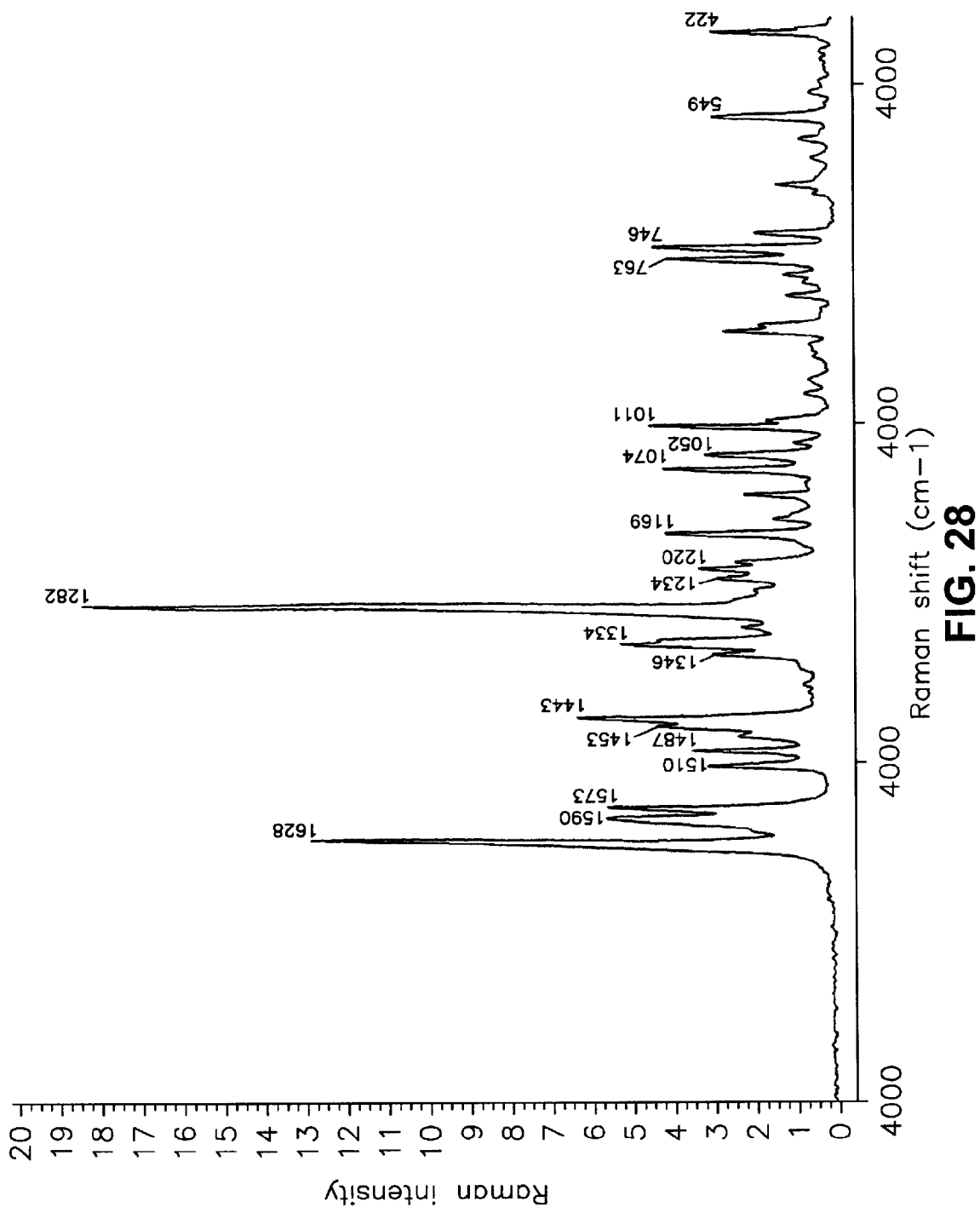
FIG. 28 is an FT-Raman spectrum for carvedilol hydrobromide 2-methyl-1-propanol solvate in the 2000-400 $cm^{-1}$ region of the spectrum.
Figure 29:
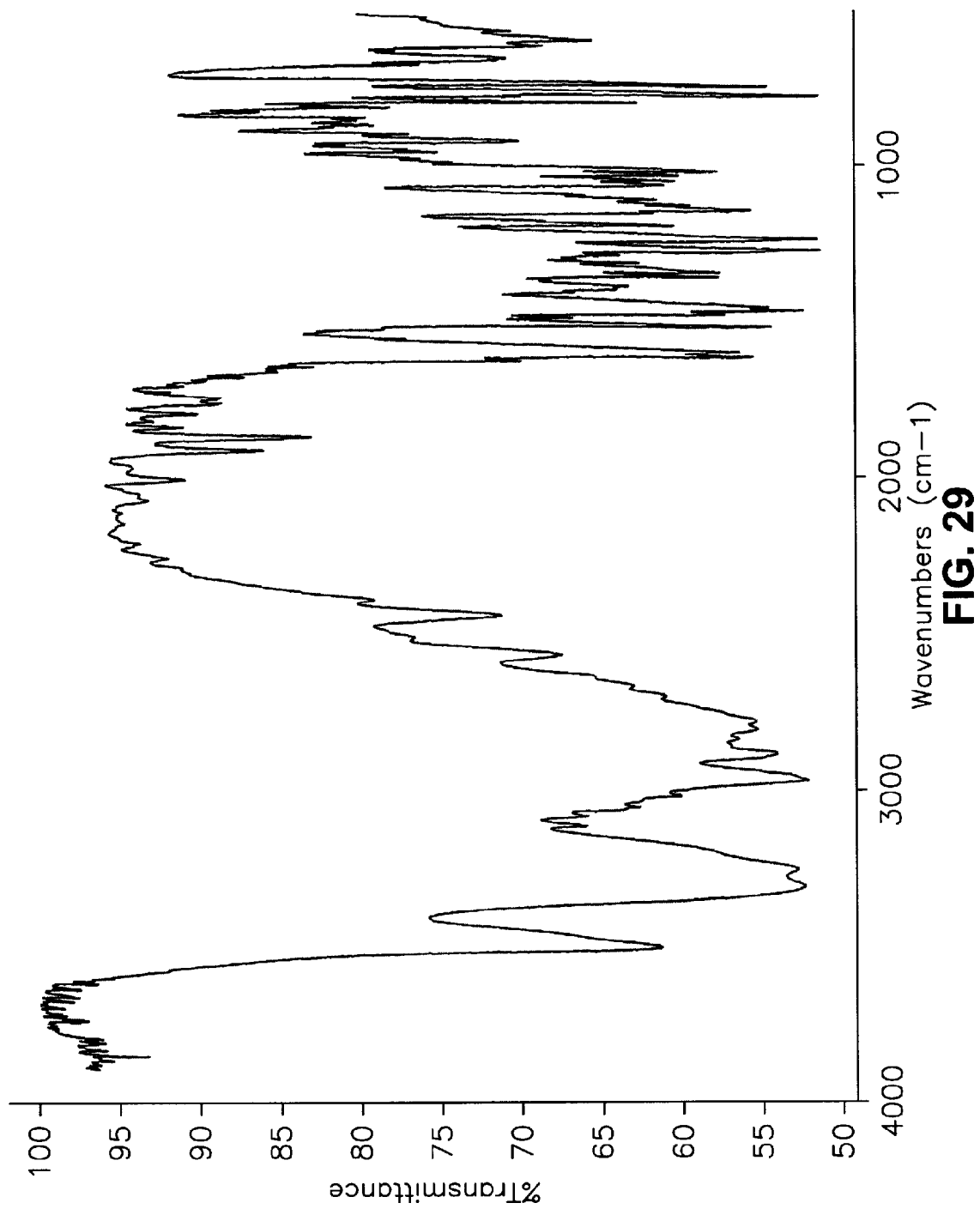
FIG. 29 is an FT-IR spectrum for carvedilol hydrobromide 2-methyl-1-propanol solvate.
Figure 30:
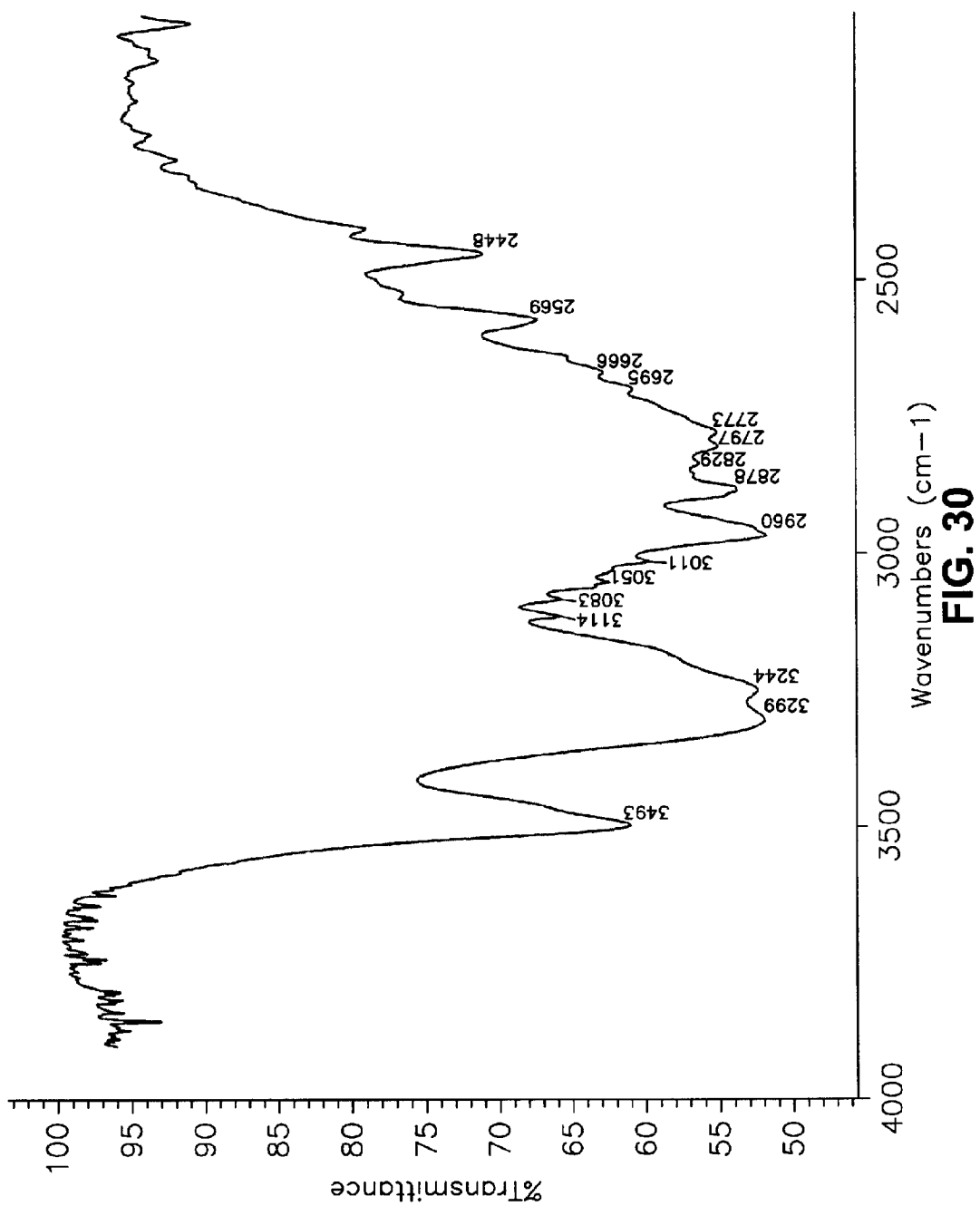
FIG. 30 is an FT-IR spectrum for carvedilol hydrobromide 2-methyl-1-propanol solvate in the 4000-2000 $cm^{-1}$ region of the spectrum.
Figure 31:
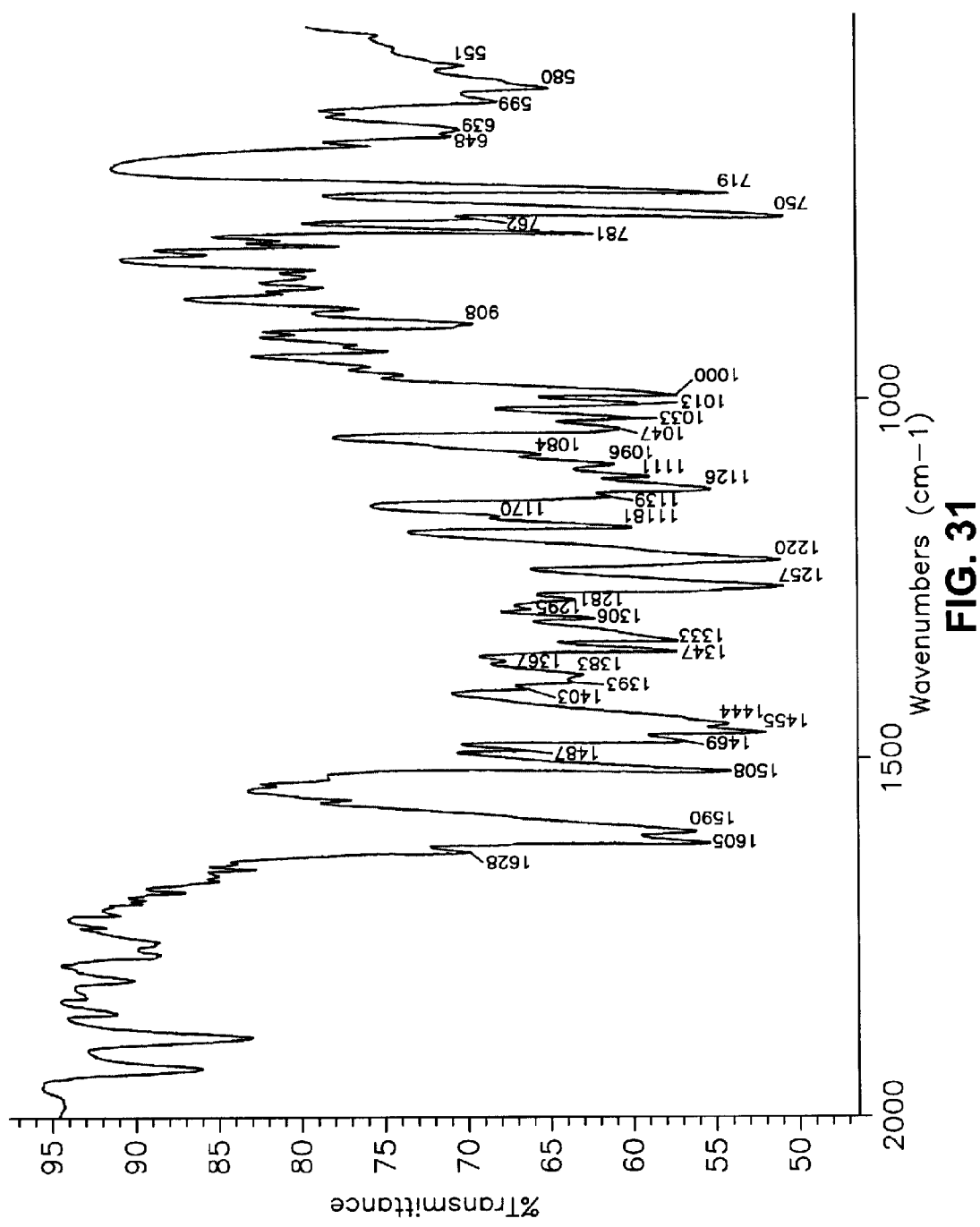
FIG. 31 is an FT-IR spectrum for carvedilol hydrobromide 2-methyl-1-propanol solvate in the 2000-500 $cm^{-1}$ region of the spectrum.
Figure 32:
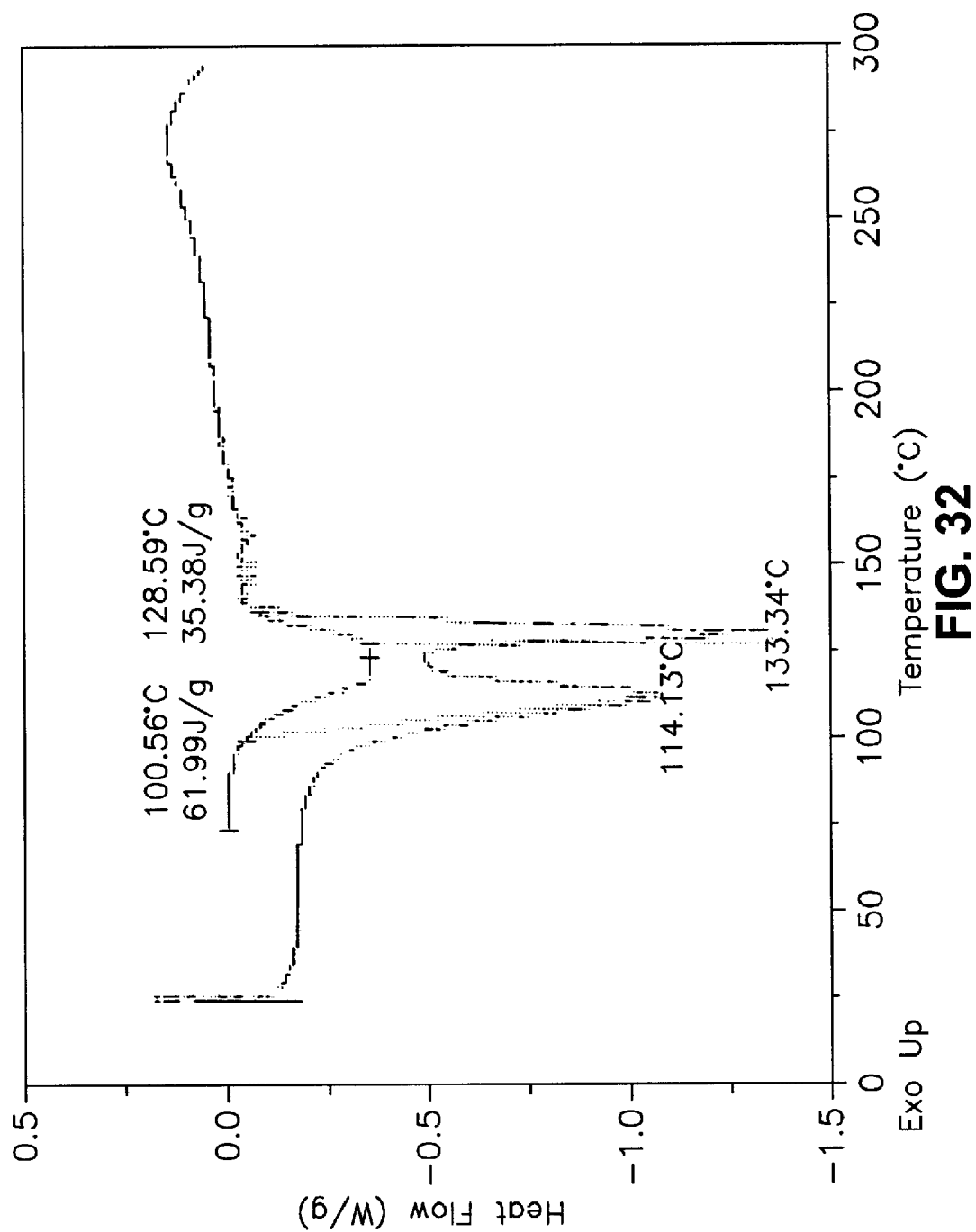
FIG. 32 is a differential scanning calorimetry thermogram for carvedilol hydrobromide trifluoroethanol solvate.
Figure 33:
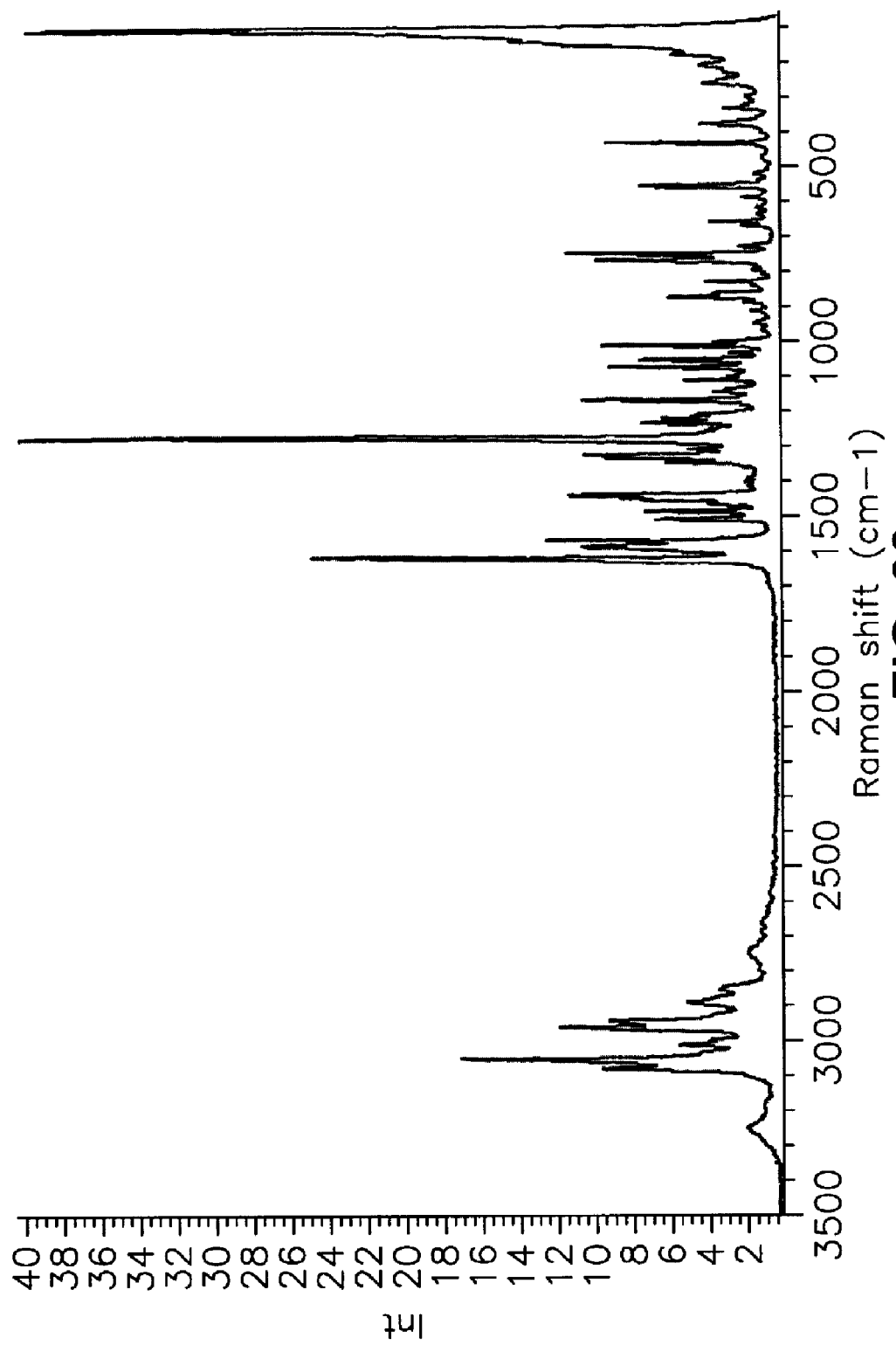
FIG. 33 is an FT-Raman spectrum for carvedilol hydrobromide trifluoroethanol solvate.
Figure 34:
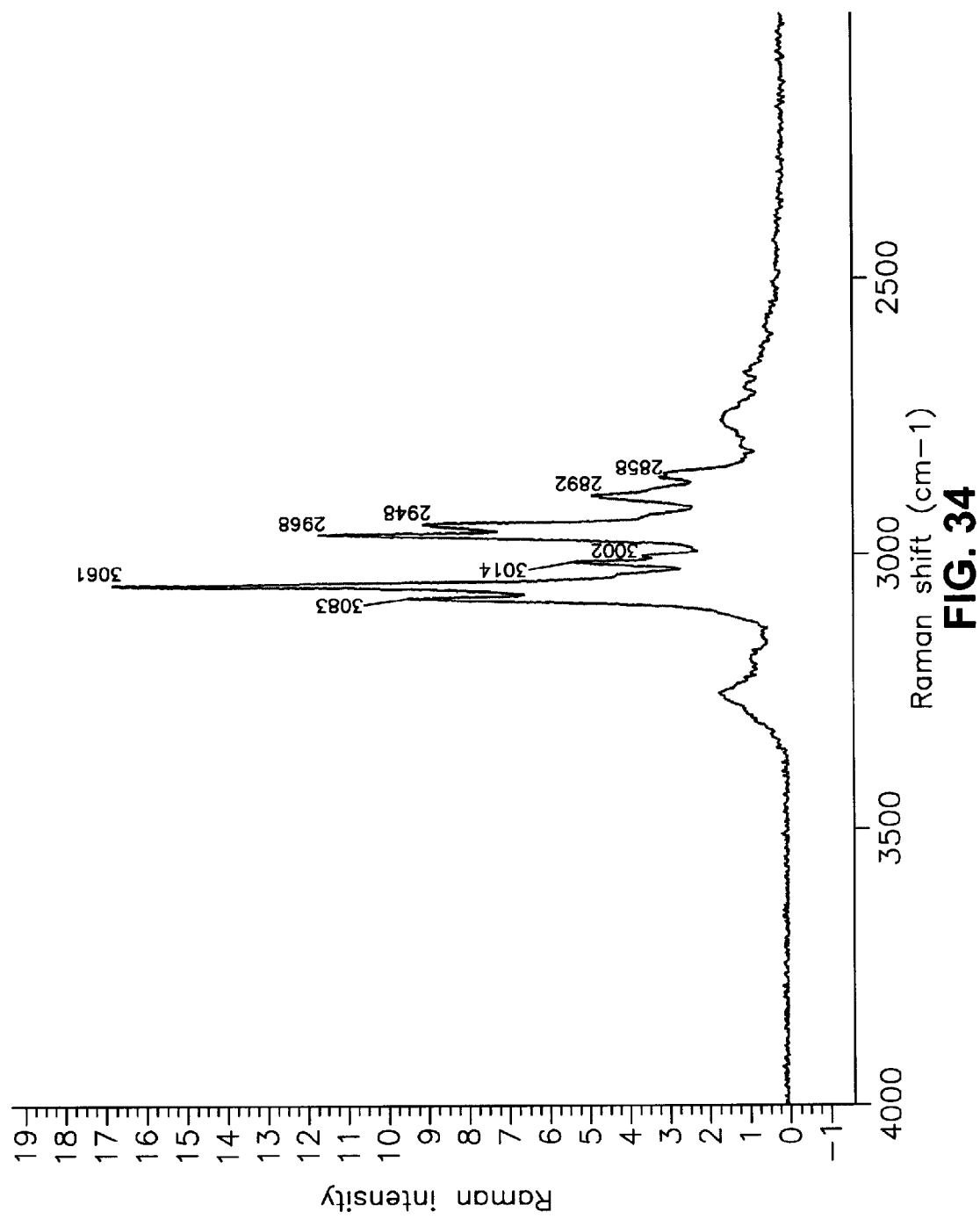
FIG. 34 is an FT-Raman spectrum for carvedilol hydrobromide trifluoroethanol solvate in the 4000-2000 $cm^{-1}$ region of the spectrum.
Figure 35:
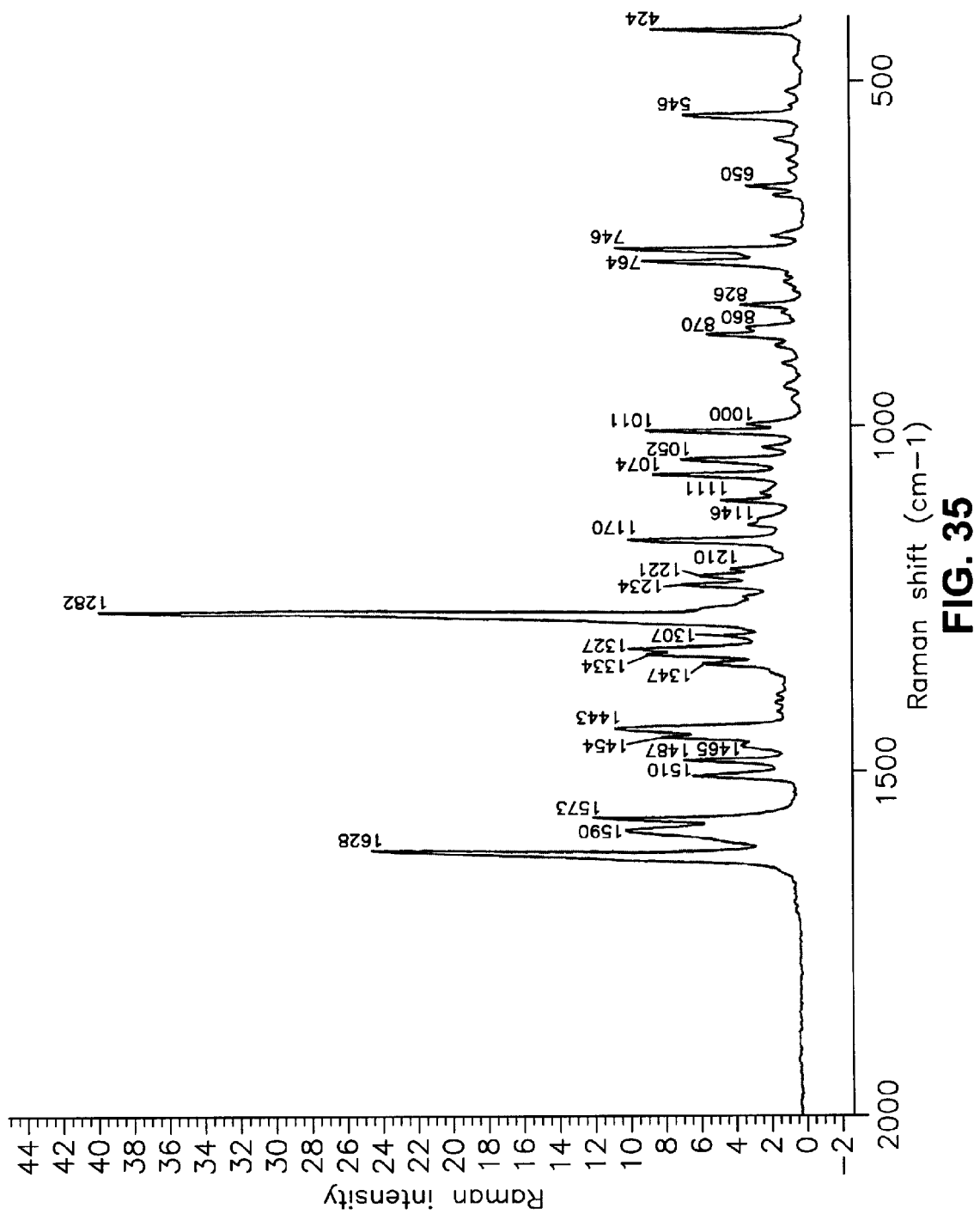
FIG. 35 is an FT-Raman spectrum for carvedilol hydrobromide trifluoroethanol solvate in the 2000-400 $cm^{-1}$ region of the spectrum.
Figure 36:
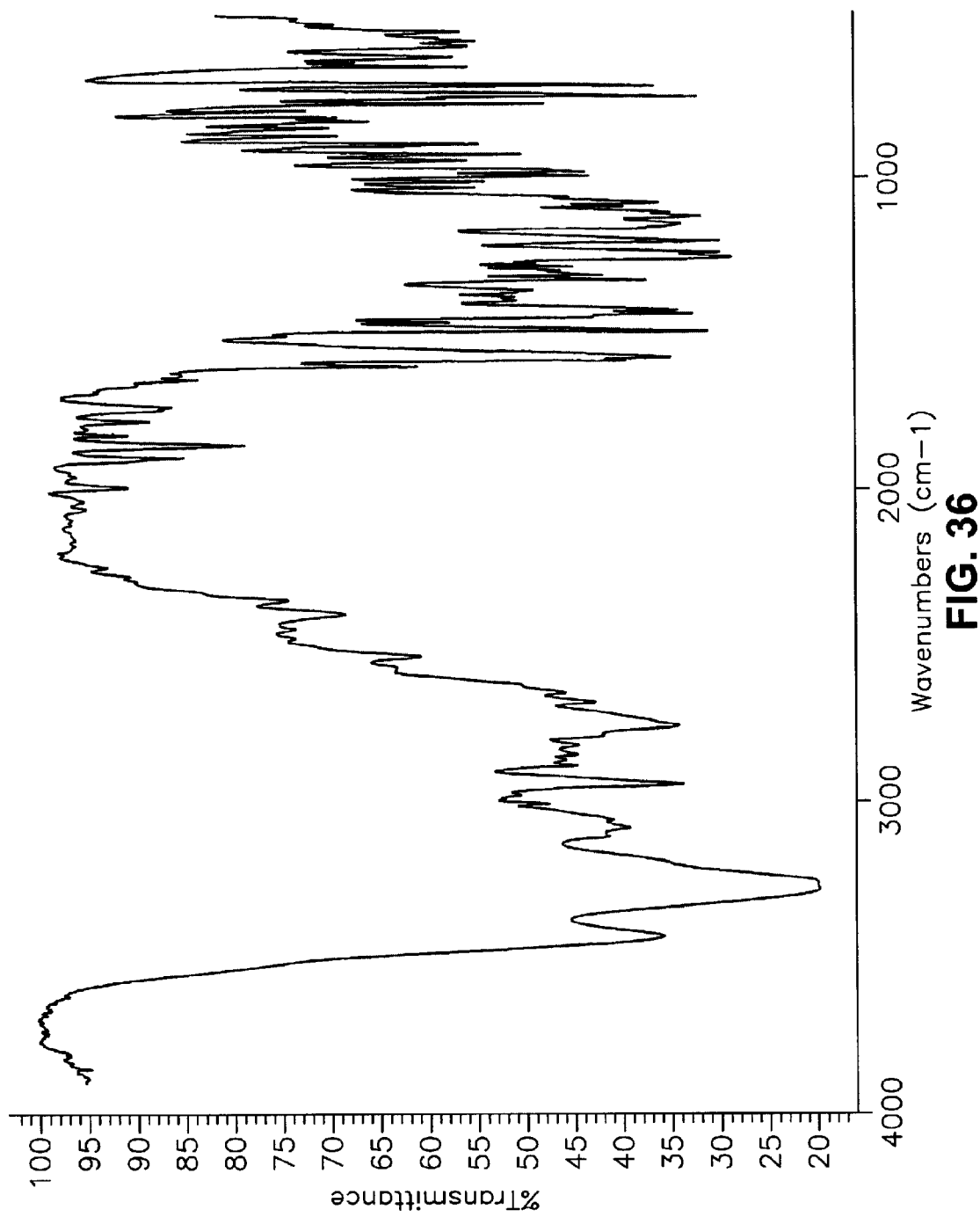
FIG. 36 is an FT-IR spectrum for carvedilol hydrobromide trifluoroethanol solvate.
Figure 37:
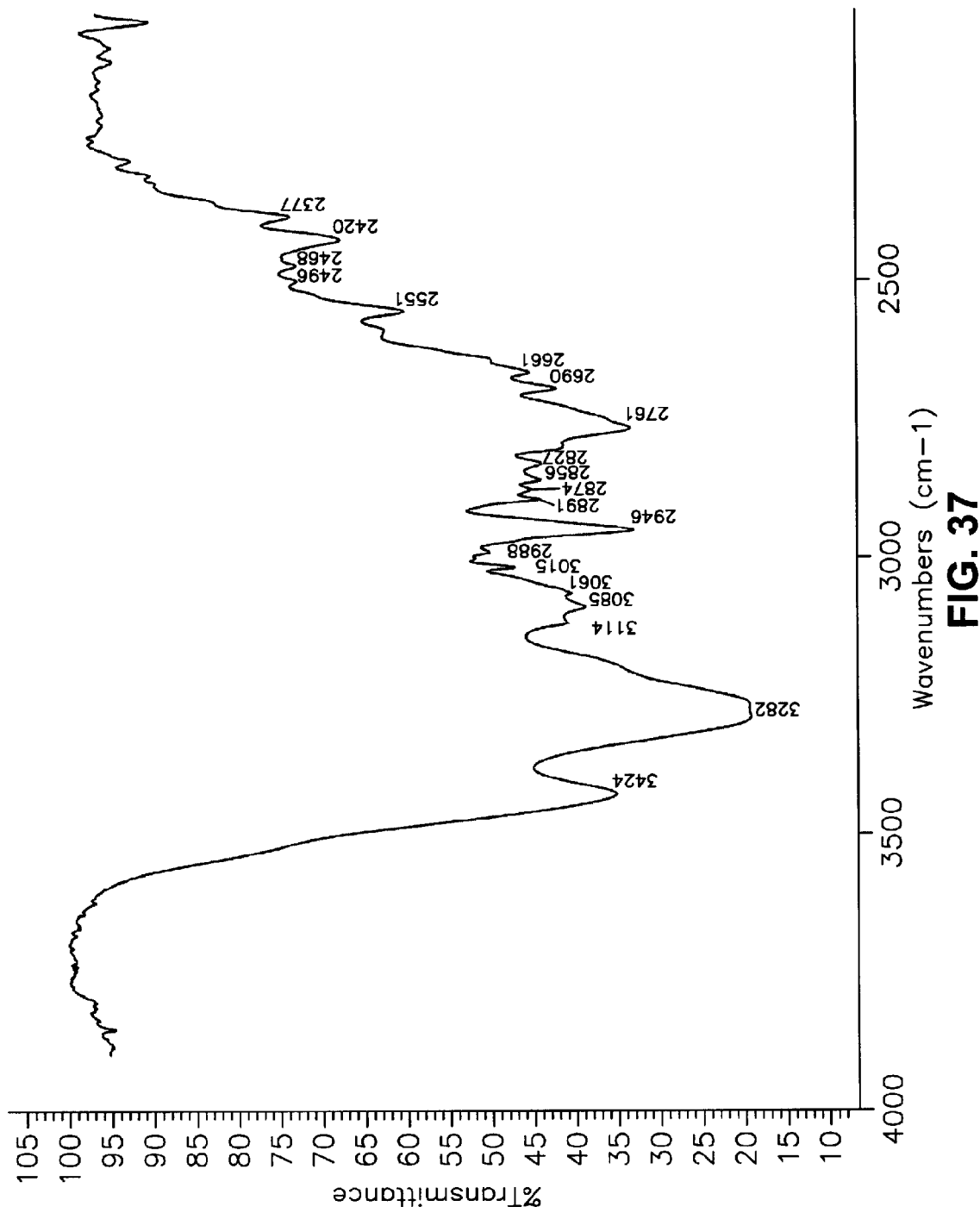
FIG. 37 is an FT-IR spectrum for carvedilol hydrobromide trifluoroethanol solvate in the 4000-2000 $cm^{-1}$ region of the spectrum.
Figure 38:
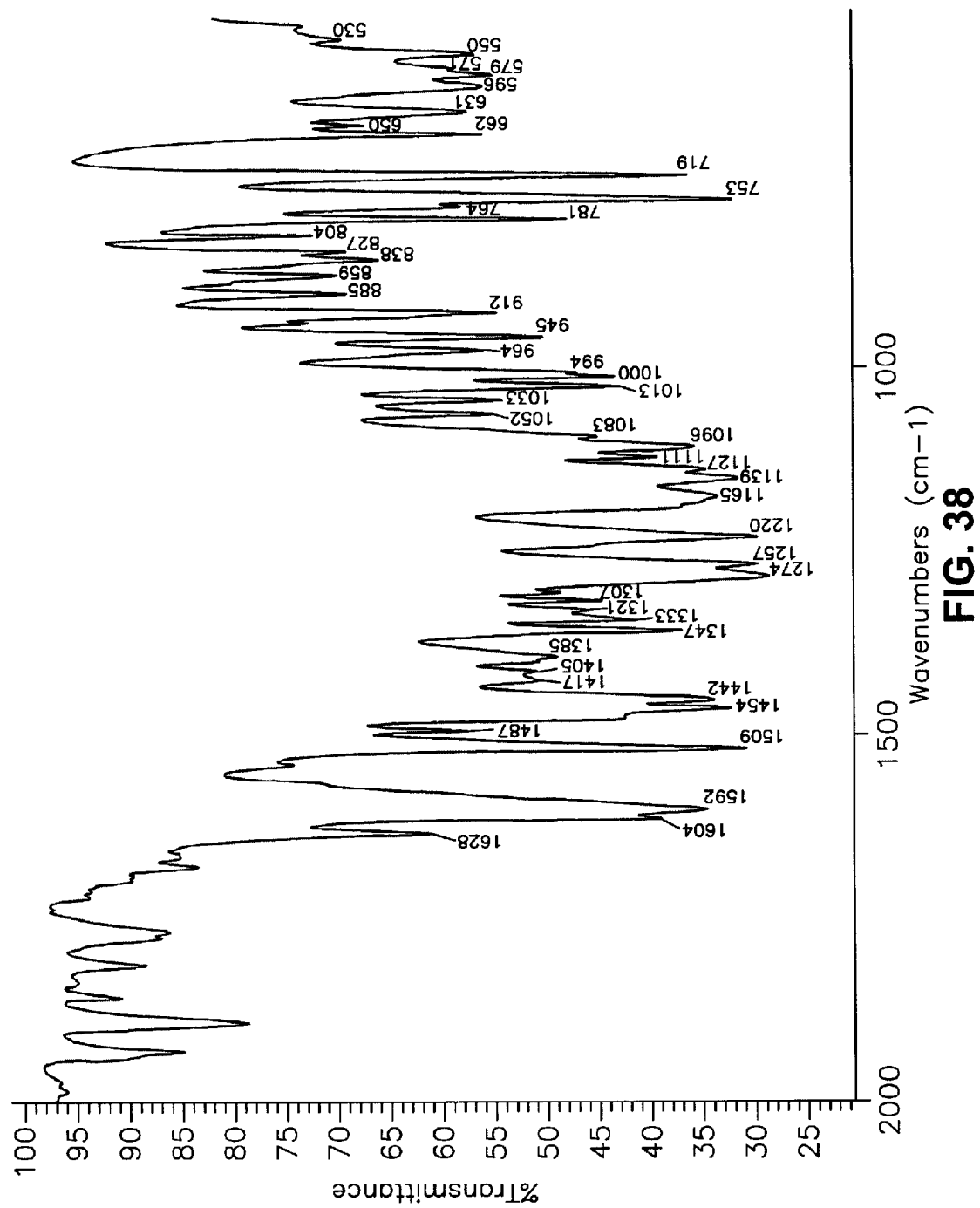
FIG. 38 is an FT-IR spectrum for carvedilol hydrobromide trifluoroethanol solvate in the 2000-500 $cm^{-1}$ region of the spectrum.
Figure 39:
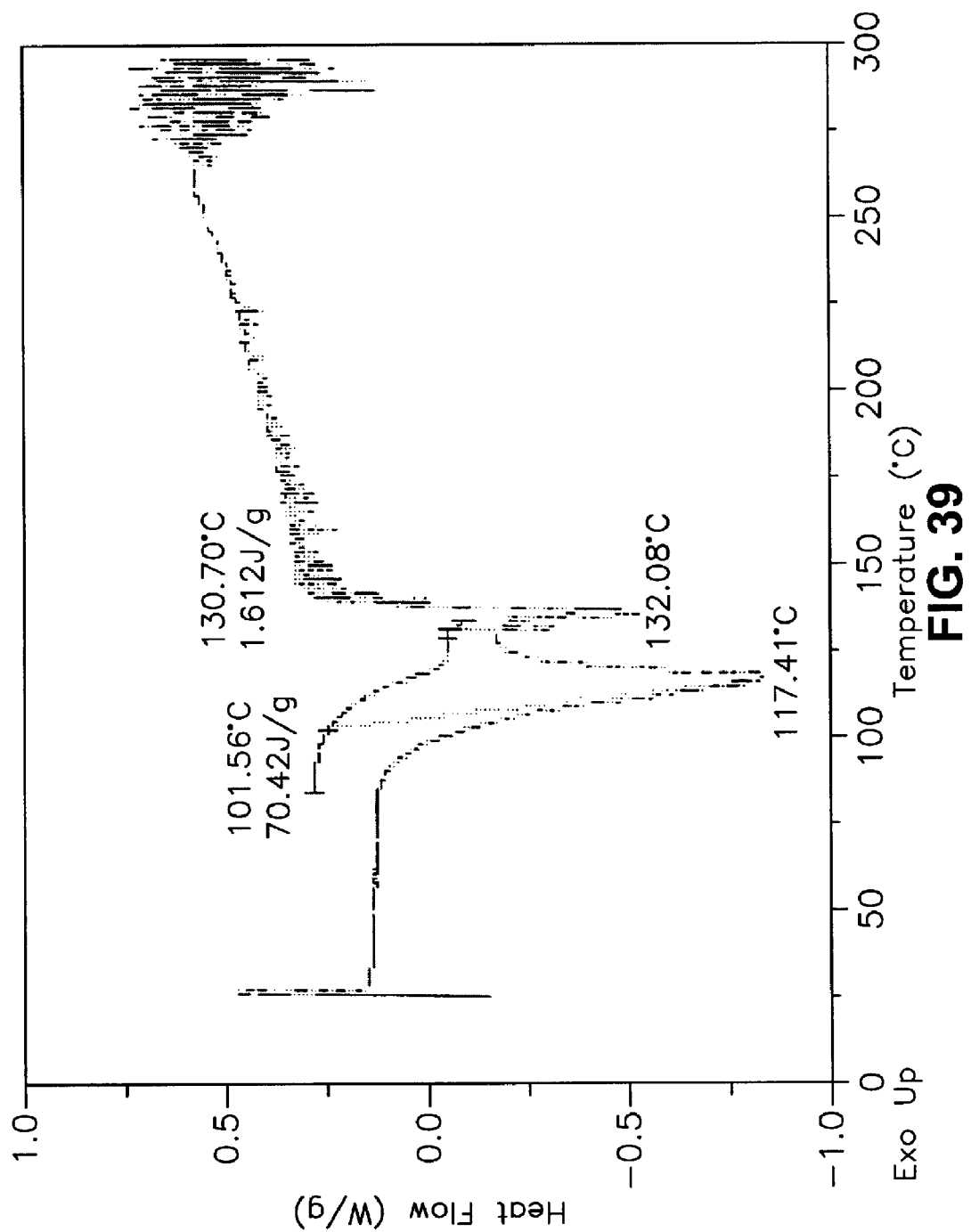
FIG. 39 is a differential scanning calorimetry thermogram for carvedilol hydrobromide 2-propanol solvate.
Figure 40:
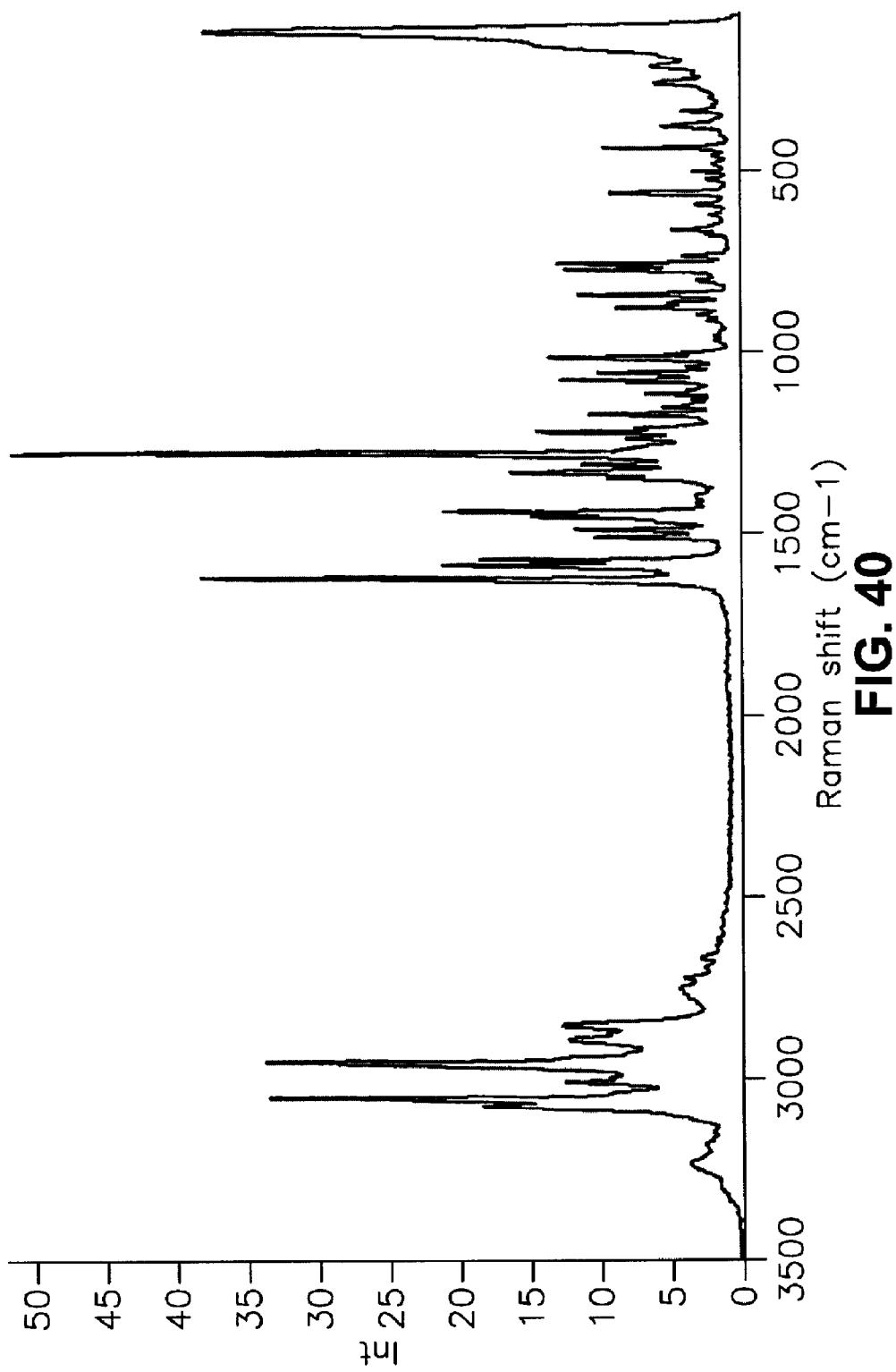
FIG. 40 is an FT-Raman spectrum for carvedilol hydrobromide 2-propanol solvate.
Figure 41:
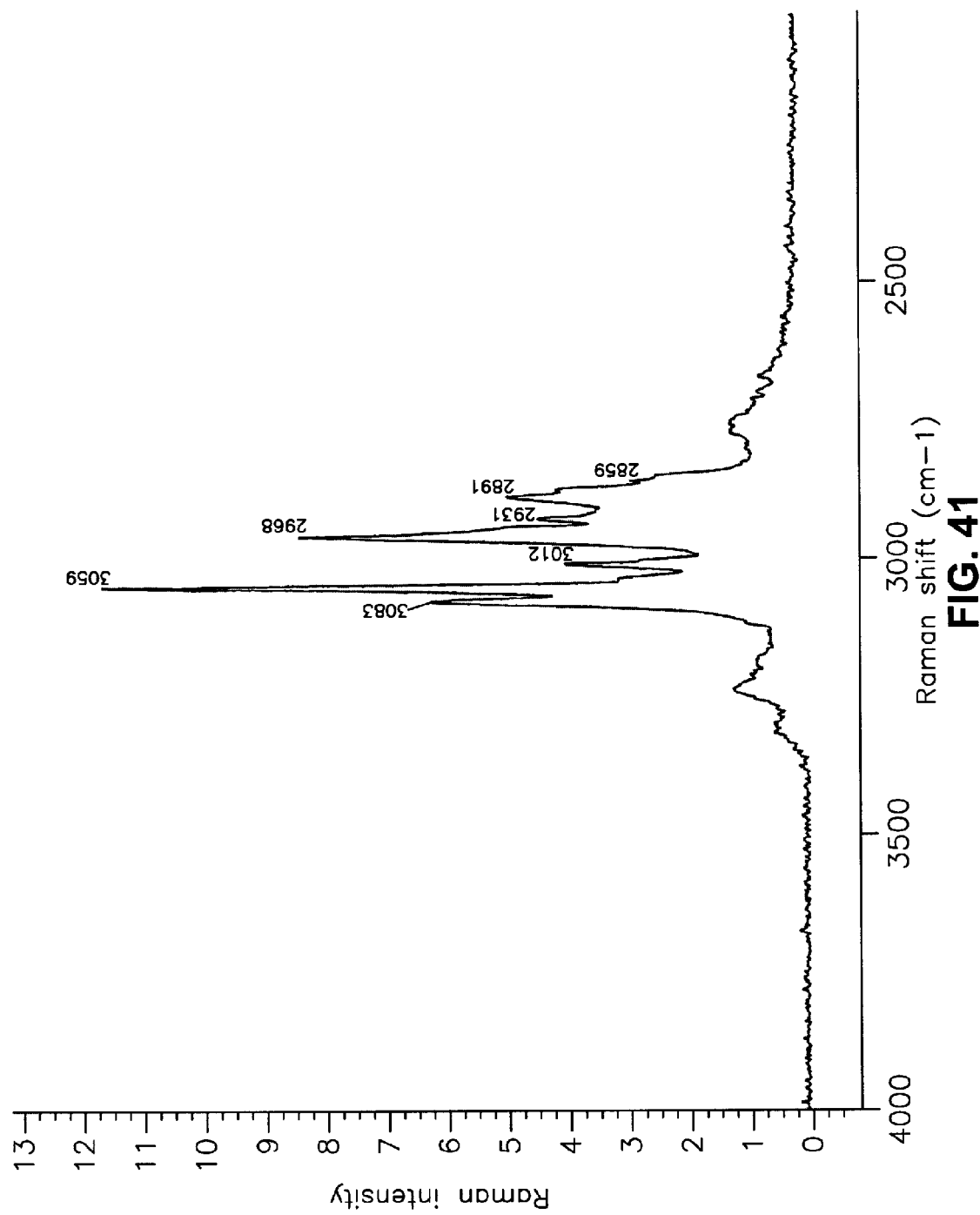
FIG. 41 is an FT-Raman spectrum for carvedilol hydrobromide 2-propanol solvate in the 4000-2000 $cm^{-1}$ region of the spectrum.
Figure 42:
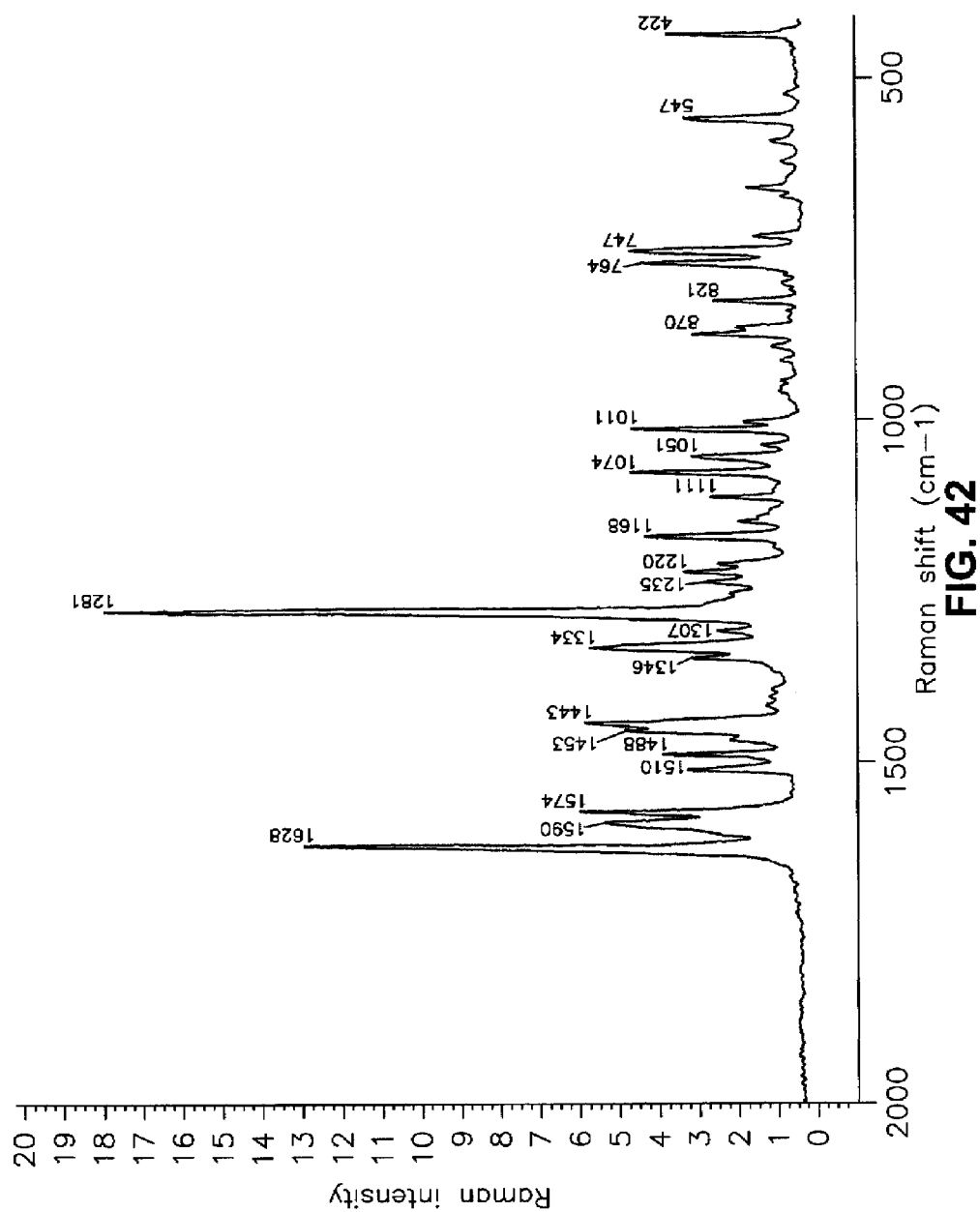
FIG. 42 is an FT-Raman spectrum for carvedilol hydrobromide 2-propanol solvate in the 2000-400 $cm^{-1}$ region of the spectrum.
Figure 43:
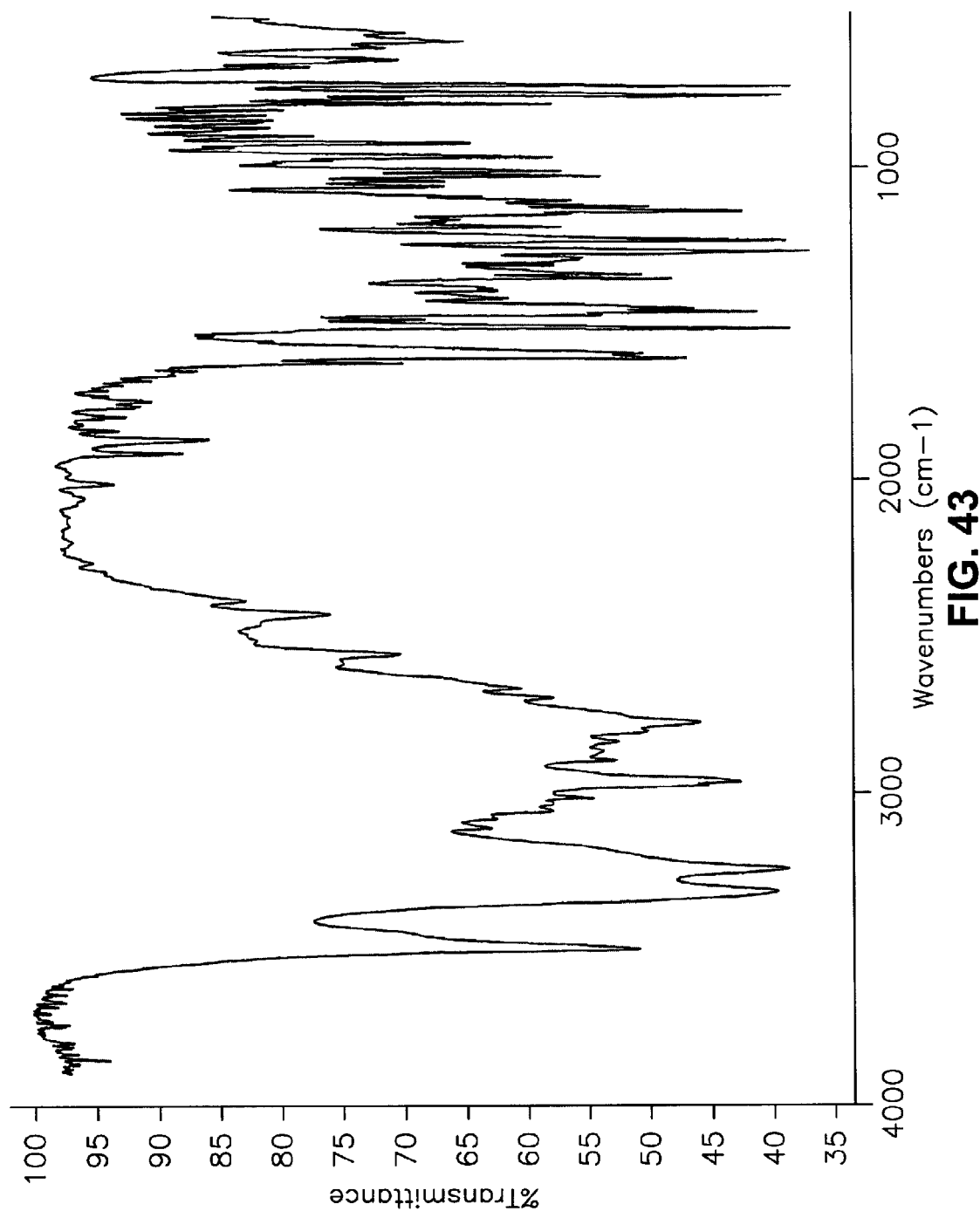
FIG. 43 is an FT-IR spectrum for carvedilol hydrobromide 2-propanol solvate.
Figure 44:
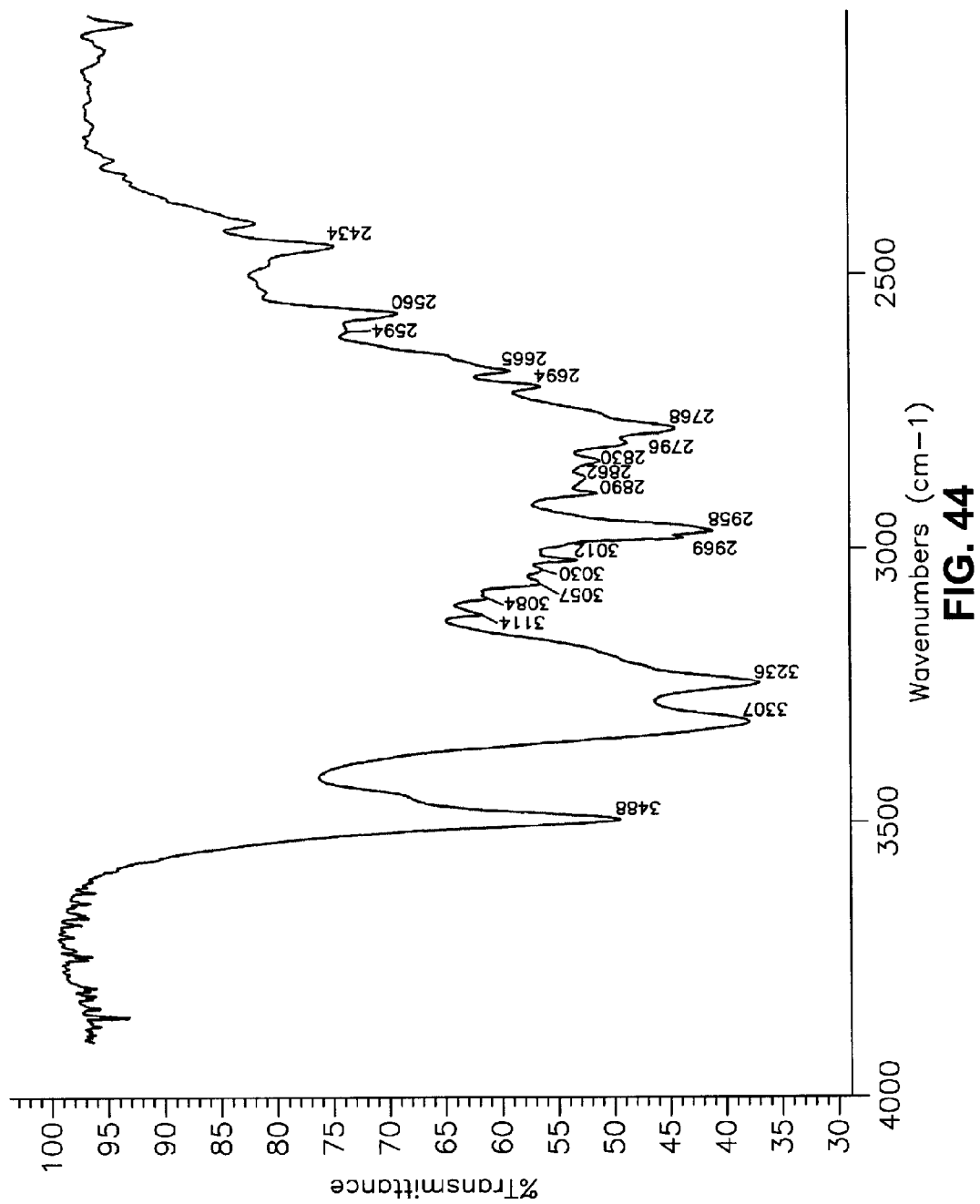
FIG. 44 is an FT-IR spectrum for carvedilol hydrobromide 2-propanol solvate in the 4000-2000 $cm^{-1}$ region of the spectrum.
Figure 45:
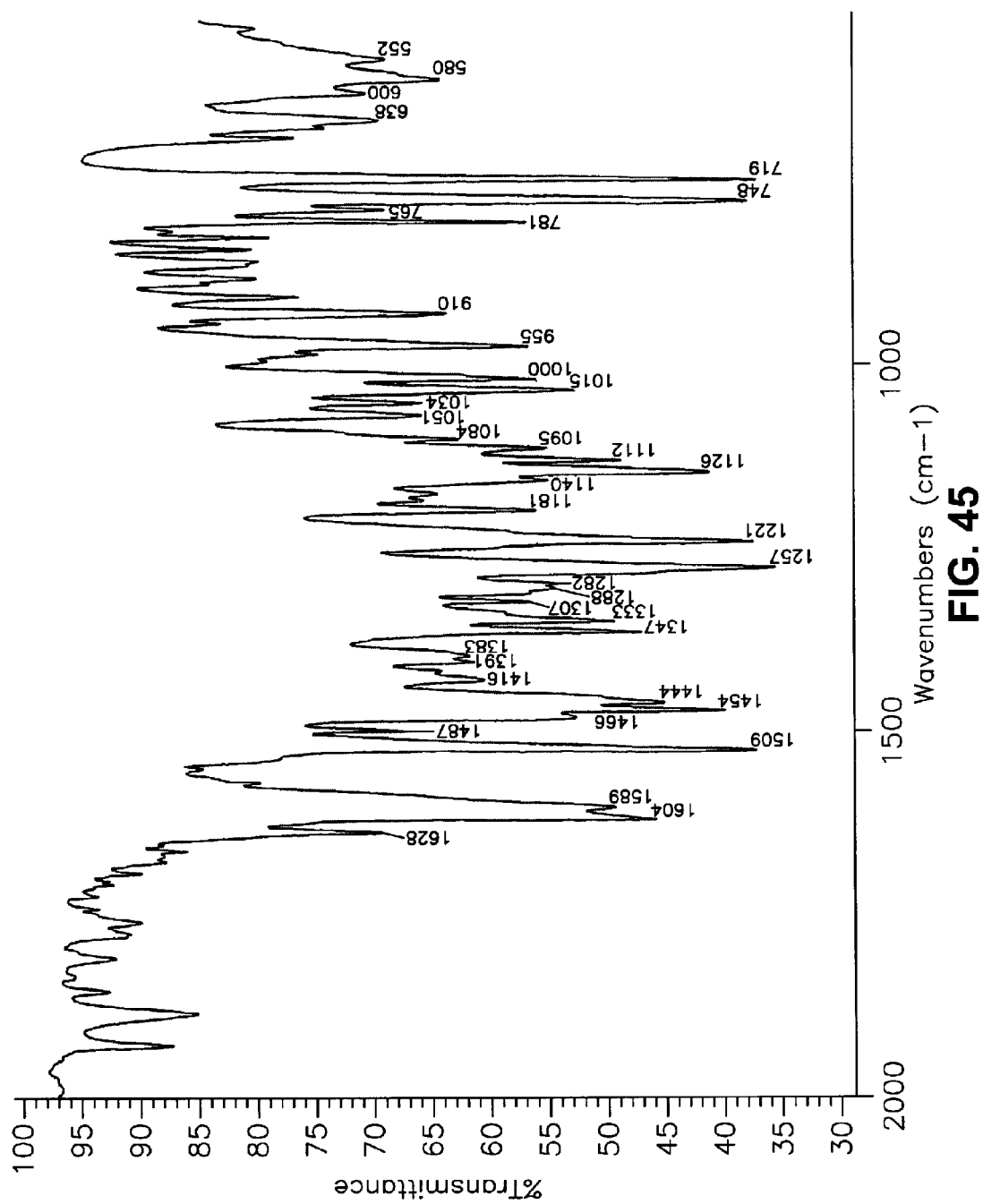
FIG. 45 is an FT-IR spectrum for carvedilol hydrobromide 2-propanol solvate in the 2000-500 $cm^{-1}$ region of the spectrum.

Crystalline carvedilol hydrobromide monohydrate further is identified by an infrared spectrum as shown substantially in FIG. 6.

Figure 67:
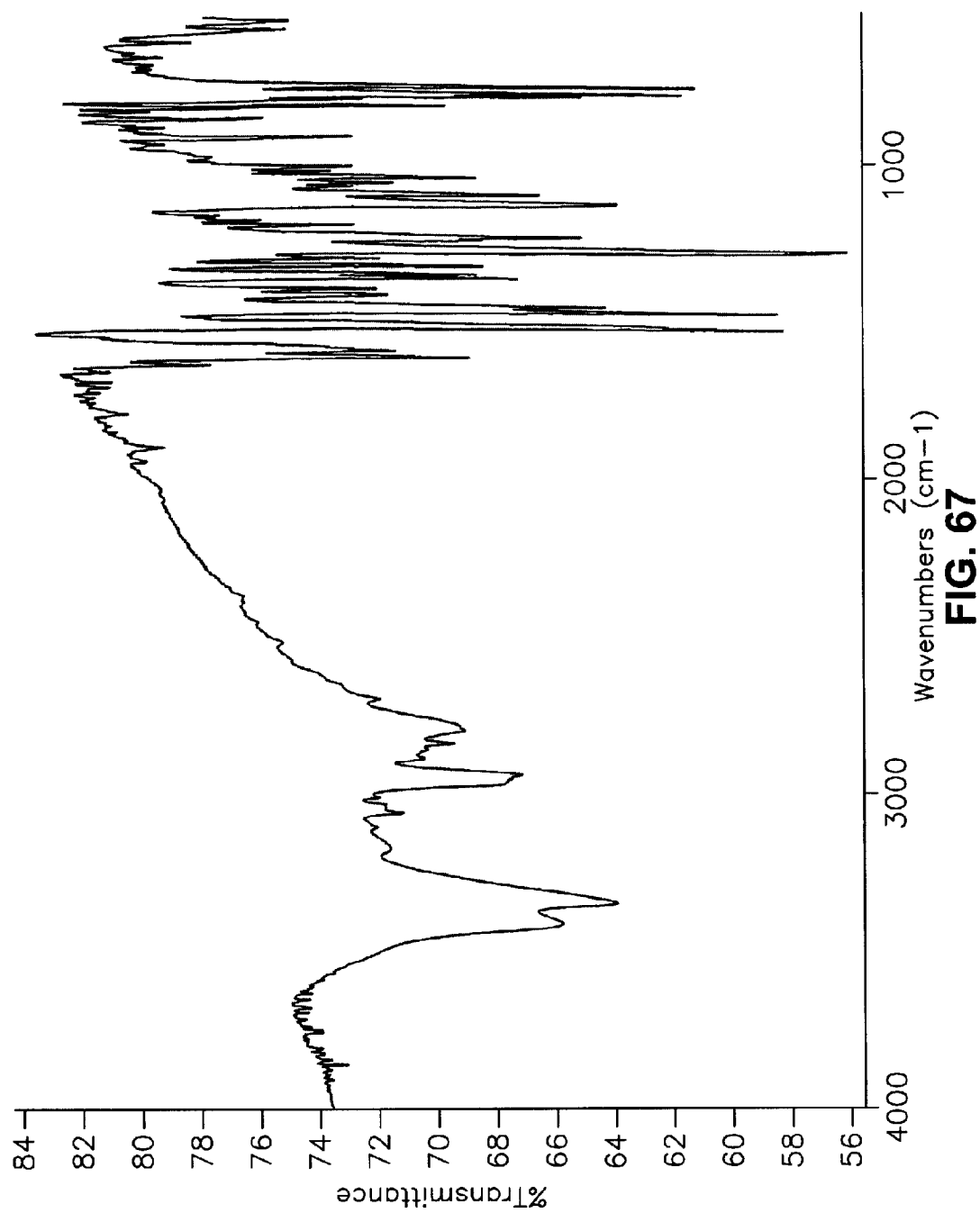
FIG. 67 is an FT-IR spectrum for carvedilol hydrobromide anhydrous.
Figure 68:
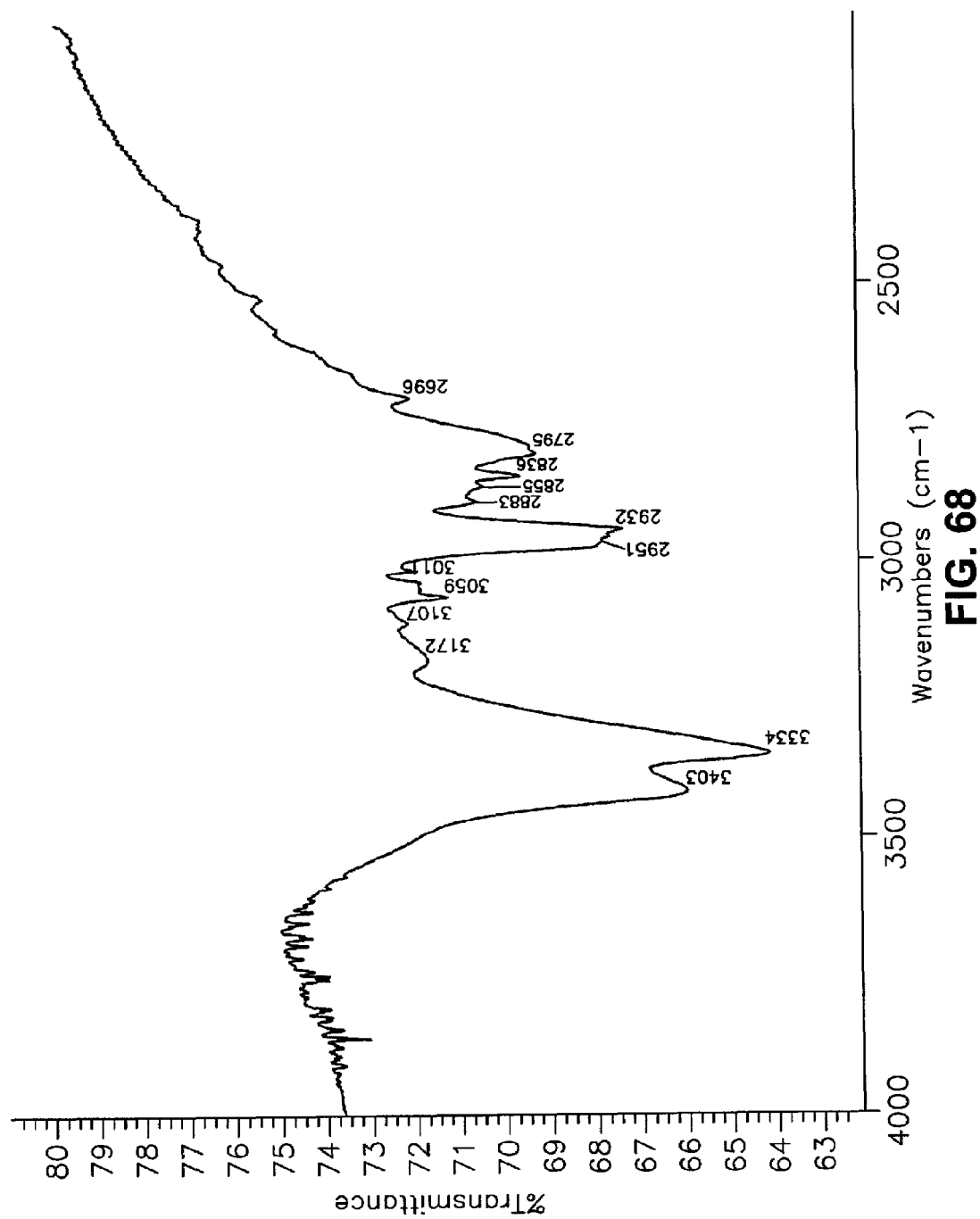
FIG. 68 is an FT-IR spectrum for carvedilol hydrobromide anhydrous in the 4000-2000 cm$^{-1}$ region of the spectrum.
Figure 69:
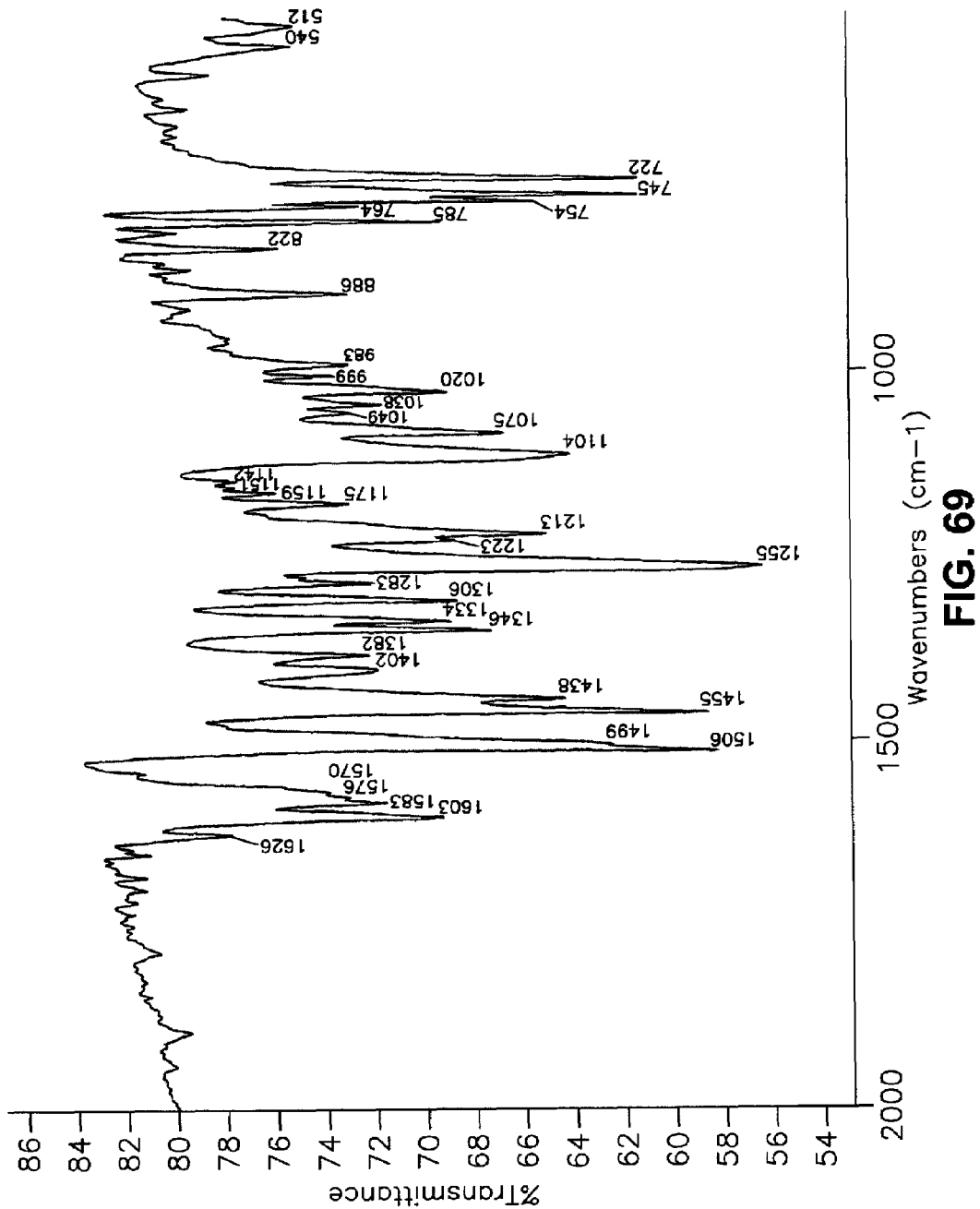
FIG. 69 is an FT-IR spectrum for carvedilol hydrobromide anhydrous in the 2000-500 cm$^{-1}$ region of the spectrum.

Carvedilol hydrobromide anhydrate also an infrared spectrum which comprises characteristic absorption bands expressed in wave numbers as shown substantially in FIG. 67.

Figure 3:
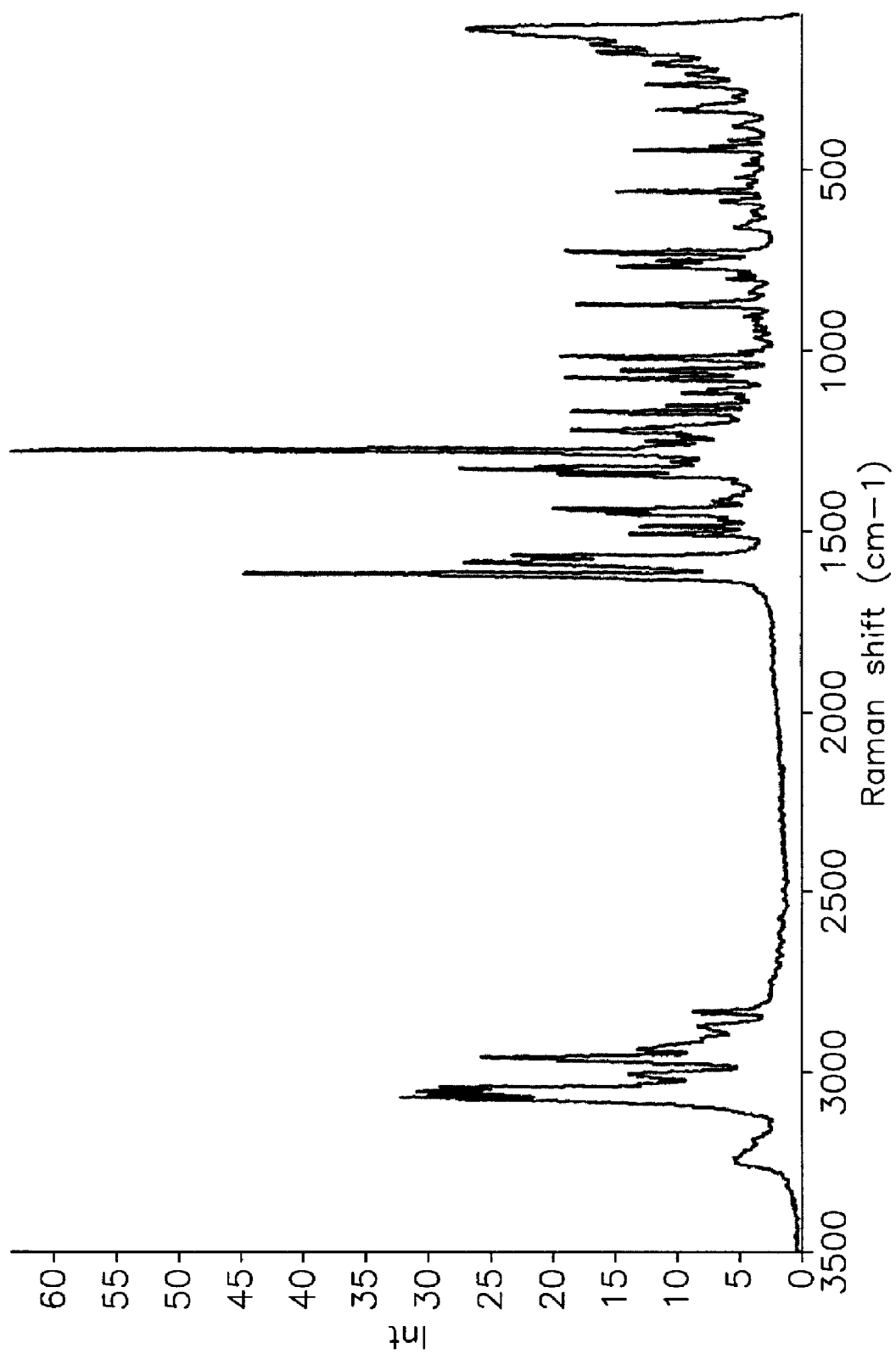
FIG. 3 is an FT-Raman spectrum for carvedilol hydrobromide monohydrate.
Figure 4:
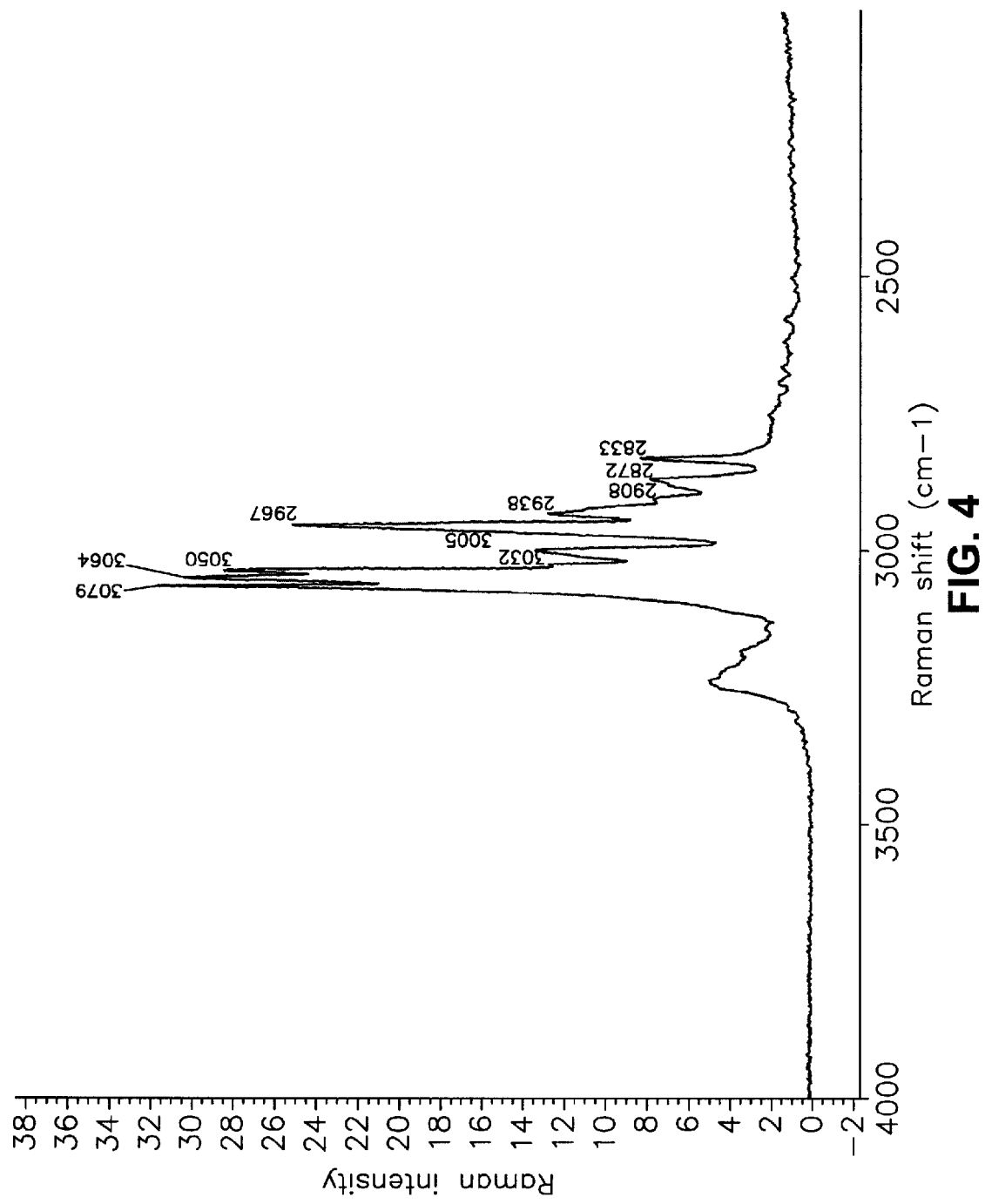
FIG. 4 is an FT-Raman spectrum for carvedilol hydrobromide monohydrate in the 4000-2000 $cm^{-1}$ region of the spectrum.
Figure 5:
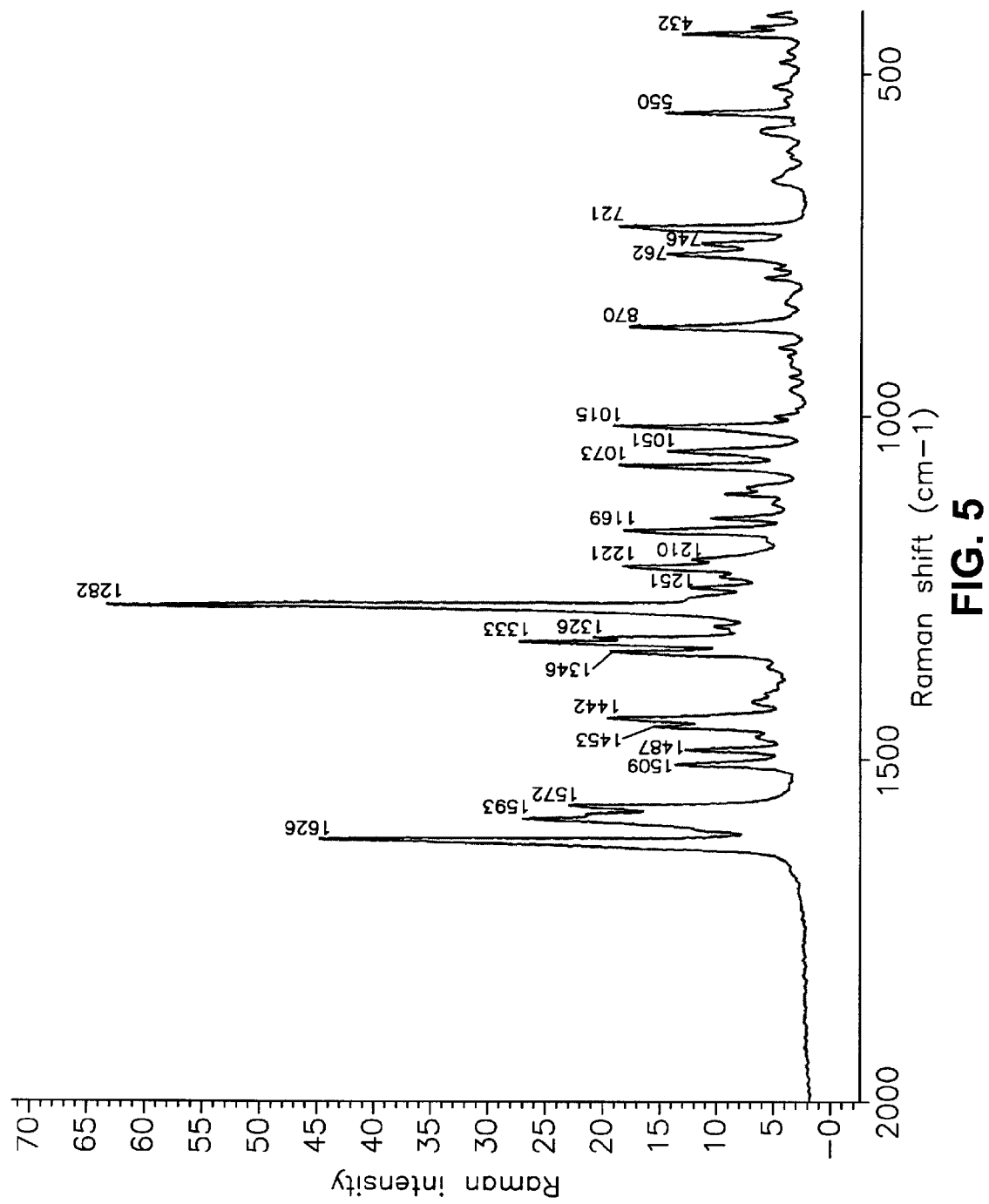
FIG. 5 is an FT-Raman spectrum for carvedilol hydrobromide monohydrate in the 2000-400 $cm^{-1}$ region of the spectrum.

Crystalline carvedilol hydrobromide monohydrate is identified also by a Raman spectrum as shown substantially in FIG. 3.

Figure 64:
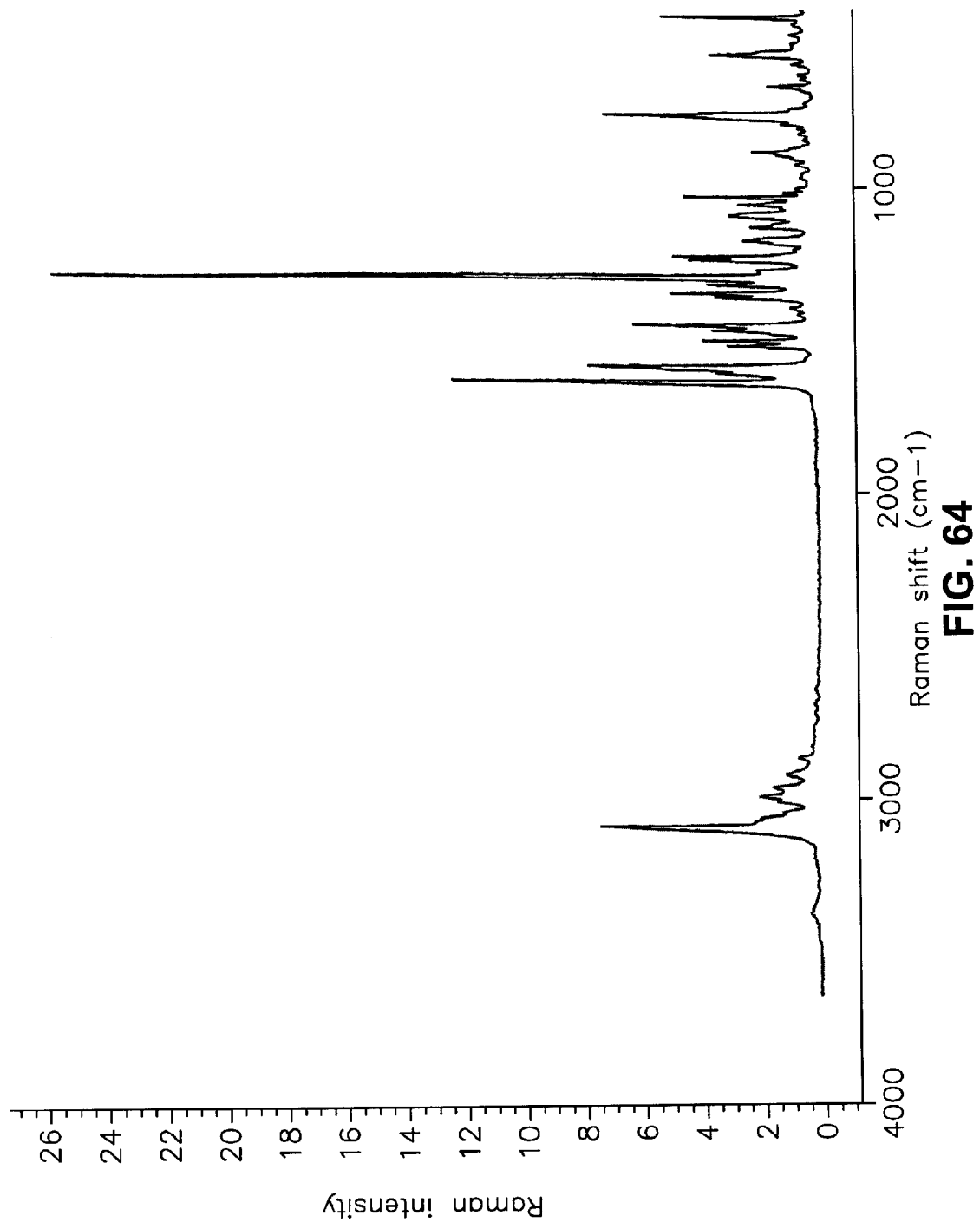
FIG. 64 is an FT-Raman spectrum for carvedilol hydrobromide anhydrous.
Figure 65:
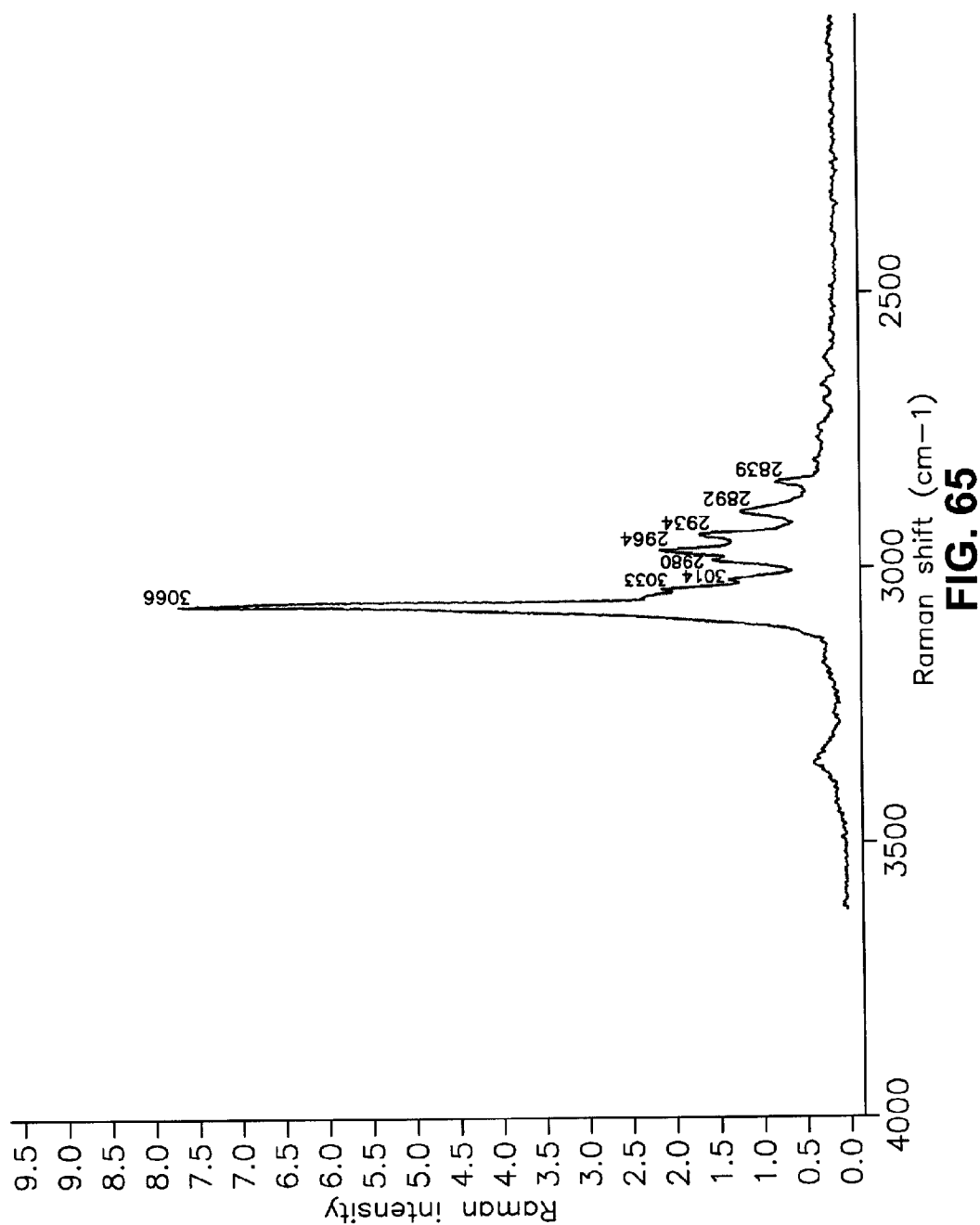
FIG. 65 is an FT-Raman spectrum for carvedilol hydrobromide anhydrous in the 4000-2000 cm$^{-1}$ region of the spectrum.
Figure 66:
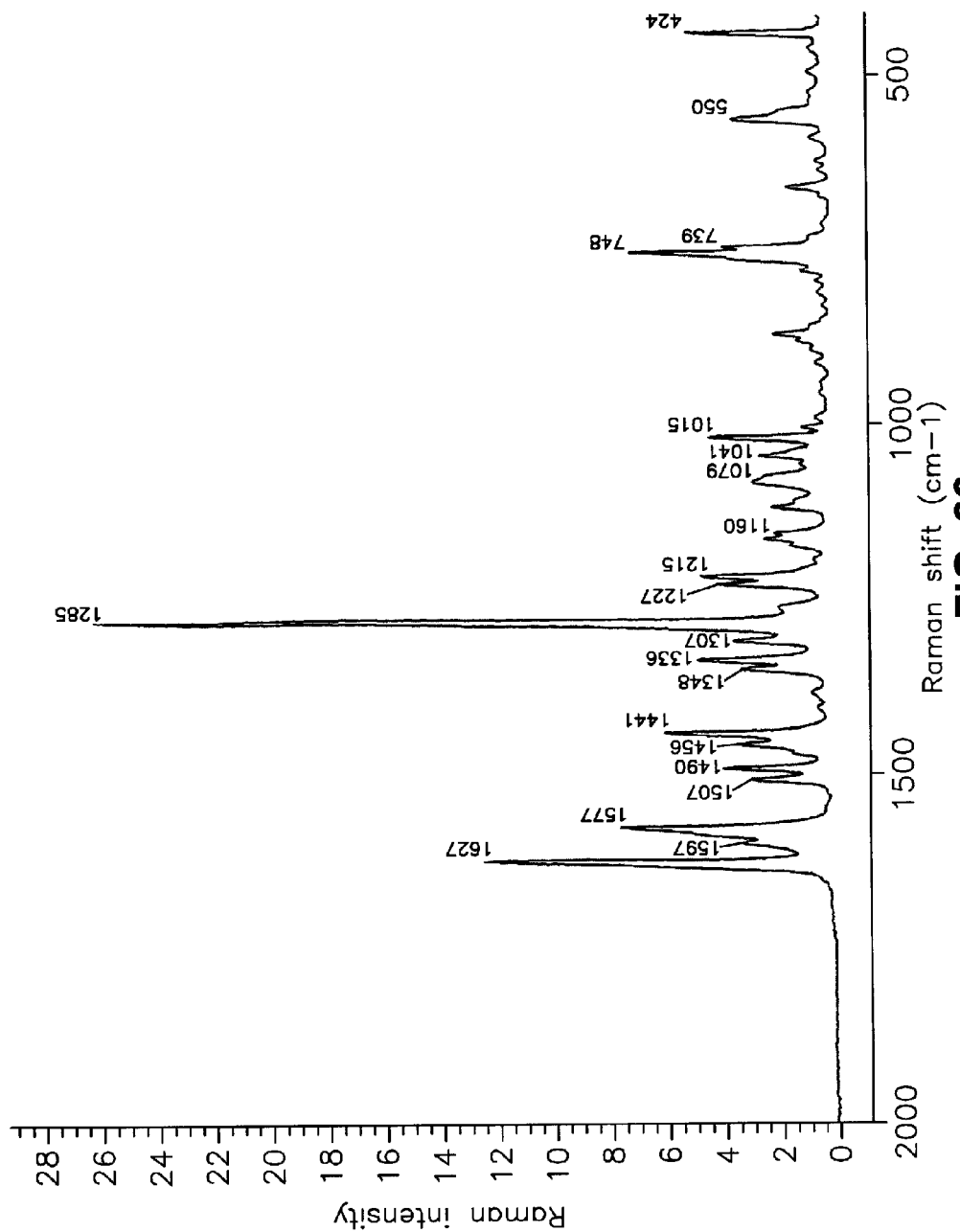
FIG. 66 is an FT-Raman spectrum for carvedilol hydrobromide anhydrous in the 2000-400 cm$^{-1}$ region of the spectrum.

Carvedilol hydrobromide anhydrate also a Raman spectrum which comprises characteristic peaks as shown substantially in FIG. 64.

Further, the present invention relates to pharmaceutical compositions, which contain the aforementioned salt and/or novel crystalline forms and/or solvates of carvedilol hydrobromide.

Importantly, the chemical and/or physical properties of carvedilol forms described herein, which include salt and/or novel crystalline forms of carvedilol, indicate that those forms may be particularly suitable for inclusion in medicinal agents, pharmaceutical compositions, etc.

For example, solubility of various carvedilol salts, anhydrates, and/or solvates as those described herein may facilitate provision or development of a dosage form from which the drug substance becomes available for bioabsorption throughout the gastrointestinal tract (i.e., in particular the lower small intestine and colon). In light of the foregoing, it may be possible to develop stable controlled release dosage forms containing such carvedilol hydrobromide monohydrate, anhydrates and/or solvates, etc., for once-per-day dosage, delayed release or pulsatile release to optimize therapy by matching pharmacokinetic performance with pharmacodynamic requirements.

Compounds or compositions within the scope of this invention include all compounds or compositions, wherein the compound of the present invention is contained in an amount effective to achieve its intended purpose. While individual needs vary, determination of optimal ranges of effective amounts of each component is within the skill of the art.

Moreover, the quantity of the compound or composition of the present invention administered will vary depending on the patient and the mode of administration and can be any effective amount.

Treatment regimen for the administration of the compounds and/or compositions of the present invention can also be determined readily by those with ordinary skill in art. The quantity of the compound and/or composition of the present invention administered may vary over a wide range to provide in a unit dosage an effective amount based upon the body weight of the patient per day to achieve the desired effect.

In particular, a composition of the present invention is presented as a unit dose and taken preferably from 1 to 2 times daily, most preferably once daily to achieve the desired effect.

Depending upon the treatment being effected, the compounds, and/or or compositions of the present invention can be administered orally, intravascularly, intraperitoneally, subcutaneously, intramuscularly or topically. Preferably, the composition is adapted for oral administration.

In general, pharmaceutical compositions of the present invention are prepared using conventional materials and techniques, such as mixing, blending and the like.

In accordance with the present invention, compounds and/or pharmaceutical composition can also include, but are not limited to, suitable adjuvants, carriers, excipients, or stabilizers, and can be in solid or liquid form such as, tablets, capsules, powders, solutions, suspensions, or emulsions.

Typically, the composition will contain a compound of the present invention, such as a salt of carvedilol or active compound(s), together with the adjuvants, carriers and/or excipients. In particular, a pharmaceutical composition of the present invention comprises an effective amount of a salt of carvedilol (i.e., such as carvedilol hydrobromide monohydrate), corresponding solvates (i.e., as identified herein) and/or anhydrates (i.e., carvedilol anhydrate) thereof, with any of the characteristics noted herein, in association with one or more non-toxic pharmaceutically acceptable carriers and/or diluents thereof, and if desired, other active ingredients.

In accordance with the present invention, solid unit dosage forms can be conventional types known in the art. The solid form can be a capsule and the like, such as an ordinary gelatin type containing the compounds of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder, such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, these active compounds can be incorporated with excipients and used in the form of tablets, capsules, elixirs, suspensions, syrups, and the like. The percentage of the compound in compositions can, of course, be varied as the amount of active compound in such therapeutically useful compositions is such that a suitable dosage will be obtained.

Typically in accordance with the present invention, the oral maintenance dose is between about 25 mg and about 50 mg, preferably given once daily. In accordance with the present invention, the preferred unit dosage forms include tablets or capsules.

The active compounds of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions of the present invention may also be administered in injectable dosages by solution or suspension of these materials in a physiologically acceptable diluent with a pharmaceutical adjuvant, carrier or excipients. Such adjuvants, carriers and/or excipients, include, but are not limited to sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The compounds and/or compositions prepared according to the present invention can be used to treat warm blooded animals, such as mammals, which include humans.

Conventional administration methods may be suitable for use in the present invention.

The present invention relates to a method for treatment of hypertension, congestive heart failure and angina in a mammal in need thereof, which method comprises administering to said mammal an effective amount of carvedilol hydrobromide monohydrate, or solvates thereof, with any of the characteristics noted herein.

The Examples set forth below are illustrative of the present invention and are not intended to limit, in any way, the scope of the present invention.

EXAMPLES

Example 1

Form 1

Carvedilol HBr Monohydrate

A suitable reactor is charged with acetone. The acetone solution is sequentially charged with carvedilol, water and 48% aqueous HBr. On addition of the water, the acetone slurry becomes a solution. The reaction mixture is stirred at room temperature. A solid precipitates during the course of the stir. The precipitate is filtered and the collected cake is washed with acetone. The cake is dried under vacuum to a constant weight. The cake is weighed and stored in a polyethylene container.

The single crystal x-ray data for carvedilol hydrobromide monohydrate is provided below.

TABLE 1

Sample and Crystal Data for Carvedilol Hydrobromide Monohydrate.

| | |
|---|---|
| Crystallization solvents | Acetone, water |
| Crystallization method | Slow cooling |
| Empirical formula | $C_{24}H_{29}BrN_2O_5$ |
| Formula weight | 505.40 |
| Temperature | 150(2) K |
| Wavelength | 0.71073 Å |
| Crystal size | 0.18 × 0.14 × 0.08 mm |
| Crystal habit | Clear colorless prism |
| Crystal system | Monoclinic |
| Space group | C2/c |
| Unit cell dimensions | a = 18.0356(3) Å $\alpha$ = 90° |
| | b = 20.8385(5) Å $\beta$ = 103.5680(10)° |
| | c = 12.9342(3) Å $\gamma$ = 90° |
| Volume | 4725.46(18) Å$^3$ |
| Z | 8 |
| Density (calculated) | 1.421 Mg/m$^3$ |
| Absorption coefficient | 1.777 mm$^{-1}$ |
| F(000) | 2096 |

TABLE 2

Data collection and structure refinement for Carvedilol Hydrobromide Monohydrate.

| | |
|---|---|
| Diffractometer | KappaCCD |
| Radiation source | Fine-focus sealed tube, MoK$_\alpha$ |
| Data collection method | CCD; rotation images; thick slices |
| Theta range for data collection | 3.42 to 23.27° |
| Index ranges | $0 \leq h \leq 20, 0 \leq k \leq 23, -14 \leq l \leq 13$ |
| Reflections collected | 30823 |
| Independent reflections | 3404 [R(int) = 0.042] |
| Coverage of independent reflections | 99.7% |
| Variation in check reflections | N/A |
| Absorption correction | Symmetry-related measurements |
| Max. and min. transmission | 0.8709 and 0.7404 |
| Structure solution technique | Direct methods |
| Structure solution program | SHELXTL V5.10 UNIX (Bruker, 1997) |
| Refinement technique | Full-matrix least-squares on $F^2$ |
| Refinement program | SHELXTL V5.10 UNIX (Bruker, 1997) |
| Function minimized | $\Sigma w(F_o^2 - F_c^2)^2$ |
| Data/restraints/parameters | 3404/11/336 |
| Goodness-of-fit on $F^2$ | 1.020 |
| $\Delta/\sigma_{max}$ | 0.000 |
| Final R indices | |
| 3071 data; I > 2σ(I) | R1 = 0.0353, wR2 = 0.0797 |
| all data | R1 = 0.0405, wR2 = 0.0829 |
| Weighting scheme | $w = 1/[\sigma^2(F_o^2) + [(0.0304P)^2 + 14.1564P]$ |
| | where $P = [MAX(F_o^2, 0) + 2F_c^2]/3$ |
| Largest diff. peak and hole | 0.786 and −0.914 e.Å$^{-3}$ |
| Refinement summary: | |
| Ordered Non-H atoms, XYZ | Freely refined |
| Ordered Non-H atoms, U | Anisotropic |
| H atoms (on carbon), XYZ | Idealized positions riding on attached atom |
| H atoms (on carbon), U | Appropriate constant times Ueq of attached atom |
| H atoms (on heteroatoms), XYZ | Freely refined |
| H atoms (on heteroatoms), U | Refined Isotropically |
| Disordered atoms, OCC | See Table 10 |
| Disordered atoms, XYZ | Refined with distance restaints |
| Disordered atoms, U | Anisotropic |

TABLE 3

Atomic Coordinates and Equivalent Isotropic Atomic Displacement Parameters (Å$^2$) for Carvedilol Hydrobromide Monohydrate. U(eq) is defined as one third of the trace of the orthogonalized $U_{ij}$ tensor.

|  | x/a | y/b | z/c | U(eq) |
|---|---|---|---|---|
| Br1 | 0.5000 | 0.22079(2) | −0.2500 | 0.04329(15) |
| Br2 | 0.0000 | 0.40821(2) | −0.2500 | 0.04510(16) |
| O1 | 0.19543(10) | 0.37037(10) | −0.00168(15) | 0.0328(5) |
| O2 | 0.08660(19) | 0.48508(15) | 0.1085(2) | 0.0312(7) |
| O2' | 0.0825(3) | 0.4816(3) | −0.0328(4) | 0.0311(13) |
| O3 | −0.19428(10) | 0.39492(10) | −0.01310(15) | 0.0347(5) |
| O4 | −0.24723(12) | 0.46974(11) | 0.11008(16) | 0.0404(5) |
| O99A | −0.0880(5) | 0.4236(3) | 0.1967(7) | 0.0430(19) |
| O99B | −0.0833(5) | 0.4514(4) | 0.1784(7) | 0.0431(19) |
| N1 | 0.34092(16) | 0.25072(13) | −0.1793(2) | 0.0390(7) |
| N2 | −0.03151(14) | 0.39706(13) | −0.0026(2) | 0.0314(6) |
| C1 | 0.26859(15) | 0.35551(14) | −0.0070(2) | 0.0301(7) |
| C2 | 0.33380(16) | 0.38188(15) | 0.0568(2) | 0.0339(7) |
| C3 | 0.40553(17) | 0.36537(16) | 0.0409(3) | 0.0402(8) |
| C4 | 0.41433(17) | 0.32249(16) | −0.0364(3) | 0.0401(8) |
| C5 | 0.34850(16) | 0.29538(15) | −0.0986(2) | 0.0343(7) |
| C6 | 0.26499(17) | 0.23737(14) | −0.2202(2) | 0.0343(7) |
| C7 | 0.23145(17) | 0.19604(15) | −0.3022(2) | 0.0401(8) |
| C8 | 0.15313(19) | 0.19096(15) | −0.3275(2) | 0.0412(8) |
| C9 | 0.10866(18) | 0.22594(14) | −0.2721(2) | 0.0364(7) |
| C10 | 0.14185(17) | 0.26731(14) | −0.1910(2) | 0.0323(7) |
| C11 | 0.22085(16) | 0.27356(13) | −0.1639(2) | 0.0300(7) |
| C12 | 0.27490(16) | 0.31103(13) | −0.0855(2) | 0.0294(6) |
| C13 | 0.18523(16) | 0.41746(14) | 0.0740(2) | 0.0301(7) |
| C14 | 0.10181(16) | 0.43671(13) | 0.0452(2) | 0.0305(7) |
| C15 | 0.05016(15) | 0.37919(14) | 0.0363(2) | 0.0289(6) |
| C16 | −0.08143(16) | 0.33991(14) | −0.0272(2) | 0.0361(7) |
| C17 | −0.16200(16) | 0.35626(16) | −0.0833(2) | 0.0380(7) |
| C18 | −0.27156(15) | 0.40680(14) | −0.0445(2) | 0.0300(6) |
| C19 | −0.30049(16) | 0.44705(14) | 0.0236(2) | 0.0316(7) |
| C20 | −0.37754(18) | 0.46060(16) | 0.0007(3) | 0.0409(8) |
| C21 | −0.42545(18) | 0.43467(17) | −0.0895(3) | 0.0499(9) |
| C22 | −0.39733(18) | 0.39593(17) | −0.1567(3) | 0.0504(9) |
| C23 | −0.31949(17) | 0.38199(15) | −0.1342(3) | 0.0388(7) |
| C24 | −0.2743(2) | 0.50999(17) | 0.1833(3) | 0.0482(9) |

TABLE 4

Selected Bond Lengths (Å) for Carvedilol Hydrobromide Monohydrate.

| O1-C1 | 1.373(3) | O1-C13 | 1.428(3) |
|---|---|---|---|
| O2-C14 | 1.366(4) | O2'-C14 | 1.360(6) |
| O3-C18 | 1.380(3) | O3-C17 | 1.435(3) |
| O4-C19 | 1.376(4) | O4-C24 | 1.433(4) |
| N1-C6 | 1.376(4) | N1-C5 | 1.381(4) |
| N2-C16 | 1.482(4) | N2-C15 | 1.488(4) |
| C1-C2 | 1.382(4) | C1-C12 | 1.399(4) |
| C2-C3 | 1.399(4) | C3-C4 | 1.378(5) |
| C4-C5 | 1.388(4) | C5-C12 | 1.415(4) |
| C6-C7 | 1.389(4) | C6-C11 | 1.416(4) |
| C7-C8 | 1.377(5) | C8-C9 | 1.399(4) |
| C9-C10 | 1.381(4) | C10-C11 | 1.391(4) |
| C11-C12 | 1.458(4) | C13-C14 | 1.517(4) |
| C14-C15 | 1.506(4) | C16-C17 | 1.503(4) |
| C18-C23 | 1.374(4) | C18-C19 | 1.403(4) |
| C19-C20 | 1.380(4) | C20-C21 | 1.388(5) |
| C21-C22 | 1.368(5) | C22-C23 | 1.396(4) |

TABLE 5

Selected bond angles (°) for Carvedilol Hydrobromide Monohydrate.

| C1-O1-C13 | 118.0(2) | C18-O3-C17 | 116.5(2) |
|---|---|---|---|
| C19-O4-C24 | 117.2(2) | C6-N1-C5 | 109.9(3) |
| C16-N2-C15 | 112.0(2) | O1-C1-C2 | 125.0(3) |
| O1-C1-C12 | 115.4(2) | C2-C1-C12 | 119.6(3) |
| C1-C2-C3 | 120.1(3) | C4-C3-C2 | 122.3(3) |
| C3-C4-C5 | 117.1(3) | N1-C5-C4 | 129.2(3) |
| N1-C5-C12 | 108.5(3) | C4-C5-C12 | 122.4(3) |
| N1-C6-C7 | 129.4(3) | N1-C6-C11 | 108.9(3) |
| C7-C6-C11 | 121.7(3) | C8-C7-C6 | 117.9(3) |
| C7-C8-C9 | 121.1(3) | C10-C9-C8 | 121.0(3) |
| C9-C10-C11 | 119.1(3) | C10-C11-C6 | 119.1(3) |
| C10-C11-C12 | 134.7(3) | C6-C11-C12 | 106.2(3) |
| C1-C12-C5 | 118.6(3) | C1-C12-C11 | 134.8(3) |
| C5-C12-C11 | 106.6(3) | O1-C13-C14 | 107.0(2) |
| O2'-C14-O2 | 83.4(3) | O2'-C14-C15 | 116.4(3) |
| O2-C14-C15 | 115.2(3) | O2'-C14-C13 | 115.6(3) |
| O2-C14-C13 | 112.0(3) | C15-C14-C13 | 111.6(2) |
| N2-C15-C14 | 111.8(3) | N2-C16-C17 | 113.0(3) |
| O3-C17-C16 | 108.1(2) | C23-C18-O3 | 125.0(3) |
| C23-C18-C19 | 120.1(3) | O3-C18-C19 | 114.9(2) |
| O4-C19-C20 | 125.4(3) | O4-C19-C18 | 115.1(2) |
| C20-C19-C18 | 119.4(3) | C19-C20-C21 | 119.8(3) |
| C22-C21-C20 | 120.9(3) | C21-C22-C23 | 119.7(3) |
| C18-C23-C22 | 120.0(3) | | |

TABLE 6

Hydrogen Bonds and Short C-H...X Contacts for Carvedilol Hydrobromide Monohydrate (Å and °).

| D-H...A | d(D-H) | d(H...A) | d(D...A) | <(DHA) |
|---|---|---|---|---|
| N1-H1N...Br1 | 0.76(3) | 2.53(4) | 3.269(3) | 166(3) |
| N2-H2NA...O99A | 0.83(4) | 2.29(4) | 3.037(10) | 149(3) |
| N2-H2NA...O99B | 0.83(4) | 2.13(4) | 2.943(10) | 165(4) |
| N2-H2NB...O2#1 | 0.89(5) | 2.17(4) | 2.873(4) | 135(4) |
| O2'-H2O'...Br2 | 0.67(5) | 2.65(7) | 3.237(6) | 149(12) |
| O99A-H99A...Br1#2 | 0.94(3) | 2.49(4) | 3.395(8) | 163(6) |
| O99B-H99B...Br2#1 | 0.94(3) | 2.38(3) | 3.320(8) | 173(6) |
| C15-H15A...O10.99 | 2.38 | 2.783(3) | 103.2 | |
| C15-H15B...Br1#2 | 0.99 | 2.85 | 3.738(3) | 149.3 |
| C16-H16A...Br1#2 | 0.99 | 2.88 | 3.760(3) | 148.2 |

Symmetry transformations used to generate equivalent atoms:
1 −x, −y + 1, −z
2 −x + 1/2, −y + 1/2, −z

TABLE 7

Selected torsion angles (°) for Carvedilol Hydrobromide Monohydrate.

| C13-O1-C1-C2 | 1.2(4) | C13-O1-C1-C12 | −177.5(2) |
|---|---|---|---|
| O1-C1-C2-C3 | −177.0(3) | C12-C1-C2-C3 | 1.7(4) |
| C1-C2-C3-C4 | −0.8(5) | C2-C3-C4-C5 | −0.5(5) |
| C6-N1-C5-C4 | −179.7(3) | C6-N1-C5-C12 | 0.8(3) |
| C3-C4-C5-N1 | −178.6(3) | C3-C4-C5-C12 | 0.8(4) |
| C5-N1-C6-C7 | 179.4(3) | C5-N1-C6-C11 | −0.9(3) |
| N1-C6-C7-C8 | 179.5(3) | C11-C6-C7-C8 | −0.1(4) |
| C6-C7-C8-C9 | −0.4(5) | C7-C8-C9-C10 | 0.8(5) |
| C8-C9-C10-C11 | −0.6(4) | C9-C10-C11-C6 | 0.0(4) |

TABLE 7-continued

Selected torsion angles (°) for Carvedilol Hydrobromide Monohydrate.

| | | | |
|---|---|---|---|
| C9-C10-C11-C12 | −179.9(3) | N1-C6-C11-C10 | −179.4(3) |
| C7-C6-C11-C10 | 0.3(4) | N1-C6-C11-C12 | 0.6(3) |
| C7-C6-C11-C12 | −179.7(3) | O1-C1-C12-C5 | 177.4(2) |
| C2-C1-C12-C5 | −1.4(4) | O1-C1-C12-C11 | −2.4(5) |
| C2-C1-C12-C11 | 178.8(3) | N1-C5-C12-C1 | 179.6(2) |
| C4-C5-C12-C1 | 0.1(4) | N1-C5-C12-C11 | −0.5(3) |
| C4-C5-C12-C11 | 180.0(3) | C10-C11-C12-C1 | −0.3(6) |
| C6-C11-C12-C1 | 179.8(3) | C10-C11-C12-C5 | 179.9(3) |
| C6-C11-C12-C5 | −0.1(3) | C1-O1-C13-C14 | 166.1(2) |
| O1-C13-C14-O2' | −82.6(4) | O1-C13-C14-O2 | −175.8(2) |
| O1-C13-C14-C15 | 53.4(3) | C16-N2-C15-C14 | 171.3(2) |
| O2'-C14-C15-N2 | −38.6(4) | O2-C14-C15-N2 | 56.6(4) |
| C13-C14-C15-N2 | −174.2(2) | C15-N2-C16-C17 | −170.5(2) |
| C18-O3-C17-C16 | −170.7(2) | N2-C16-C17-O3 | −63.3(3) |
| C17-O3-C18-C23 | 3.3(4) | C17-O3-C18-C19 | −177.3(3) |
| C24-O4-C19-C20 | 1.0(4) | C24-O4-C19-C18 | −178.7(3) |
| C23-C18-C19-O4 | −179.2(3) | O3-C18-C19-O4 | 1.4(4) |
| C23-C18-C19-C20 | 1.0(4) | O3-C18-C19-C20 | −178.3(3) |
| O4-C19-C20-C21 | 179.9(3) | C18-C19-C20-C21 | −0.4(5) |
| C19-C20-C21-C22 | −0.3(5) | C20-C21-C22-C23 | 0.3(6) |
| O3-C18-C23-C22 | 178.2(3) | C19-C18-C23-C22 | −1.1(5) |
| C21-C22-C23-C18 | 0.4(5) | | |

TABLE 8

Anisotropic Atomic Displacement Parameters (Å$^2$) for Carvedilol Hydrobromide Monohydrate.
The anisotropic atomic displacement factor exponent takes the form:
$-2\pi^2 [h^2 a^{*2} U_{11} + \ldots + 2hka^* b^* U_{12}]$

| | $U_{11}$ | $U_{22}$ | $U_{33}$ | $U_{23}$ | $U_{13}$ | $U_{12}$ |
|---|---|---|---|---|---|---|
| Br1 | 0.0484(3) | 0.0447(3) | 0.0464(3) | 0.000 | 0.0306(2) | 0.000 |
| Br2 | 0.0707(3) | 0.0413(3) | 0.0234(2) | 0.000 | 0.0111(2) | 0.000 |
| O1 | 0.0272(11) | 0.0408(12) | 0.0323(11) | 0.0067(9) | 0.0108(9) | −0.0009(9) |
| O2 | 0.0416(18) | 0.0306(18) | 0.0215(17) | −0.0006(14) | 0.0077(15) | 0.0059(14) |
| O2' | 0.038(3) | 0.028(3) | 0.031(3) | 0.001(3) | 0.014(3) | 0.000(3) |
| O3 | 0.0254(11) | 0.0473(13) | 0.0308(11) | −0.0091(9) | 0.0058(9) | −0.0001(9) |
| O4 | 0.0400(12) | 0.0500(14) | 0.0323(11) | −0.0076(10) | 0.0108(10) | 0.0019(10) |
| O99A | 0.042(3) | 0.044(5) | 0.040(4) | −0.004(4) | 0.004(3) | 0.002(4) |
| O99B | 0.033(3) | 0.061(6) | 0.035(4) | −0.004(4) | 0.007(2) | −0.010(4) |
| N1 | 0.0384(17) | 0.0449(17) | 0.0393(16) | 0.0053(13) | 0.0203(14) | 0.0112(13) |
| N2 | 0.0270(13) | 0.0341(15) | 0.0332(15) | 0.0015(13) | 0.0075(12) | 0.0033(11) |
| C1 | 0.0283(16) | 0.0324(16) | 0.0321(16) | 0.0078(13) | 0.0124(13) | 0.0005(12) |
| C2 | 0.0321(17) | 0.0381(17) | 0.0327(16) | 0.0056(13) | 0.0100(13) | −0.0014(13) |
| C3 | 0.0301(17) | 0.048(2) | 0.0412(18) | 0.0104(16) | 0.0051(14) | −0.0044(14) |
| C4 | 0.0290(17) | 0.0471(19) | 0.0470(19) | 0.0133(16) | 0.0148(15) | 0.0064(14) |
| C5 | 0.0324(17) | 0.0390(17) | 0.0343(16) | 0.0113(14) | 0.0132(14) | 0.0065(14) |
| C6 | 0.0391(18) | 0.0334(17) | 0.0339(17) | 0.0099(14) | 0.0161(14) | 0.0088(14) |
| C7 | 0.056(2) | 0.0324(17) | 0.0362(18) | 0.0011(14) | 0.0204(16) | 0.0098(15) |
| C8 | 0.055(2) | 0.0337(18) | 0.0357(18) | −0.0020(14) | 0.0119(16) | 0.0003(15) |
| C9 | 0.0411(18) | 0.0344(17) | 0.0348(17) | 0.0030(14) | 0.0111(14) | −0.0009(14) |
| C10 | 0.0362(17) | 0.0321(16) | 0.0323(16) | 0.0038(13) | 0.0155(14) | 0.0022(13) |
| C11 | 0.0377(17) | 0.0275(15) | 0.0277(15) | 0.0079(12) | 0.0136(13) | 0.0040(13) |
| C12 | 0.0305(16) | 0.0309(16) | 0.0295(15) | 0.0085(13) | 0.0122(13) | 0.0017(12) |
| C13 | 0.0311(16) | 0.0331(16) | 0.0265(15) | −0.0019(12) | 0.0078(12) | −0.0021(12) |
| C14 | 0.0325(16) | 0.0307(16) | 0.0290(16) | 0.0010(13) | 0.0083(13) | 0.0015(13) |
| C15 | 0.0263(15) | 0.0327(16) | 0.0289(15) | 0.0031(12) | 0.0090(12) | 0.0043(12) |
| C16 | 0.0322(16) | 0.0347(17) | 0.0390(18) | −0.0078(14) | 0.0036(14) | 0.0016(13) |
| C17 | 0.0298(16) | 0.0477(19) | 0.0342(17) | −0.0106(15) | 0.0031(13) | 0.0023(14) |
| C18 | 0.0246(15) | 0.0317(16) | 0.0337(16) | 0.0031(13) | 0.0069(13) | −0.0014(12) |
| C19 | 0.0299(16) | 0.0352(17) | 0.0313(16) | 0.0063(13) | 0.0103(13) | −0.0031(13) |
| C20 | 0.0379(18) | 0.0382(18) | 0.051(2) | 0.0048(15) | 0.0194(16) | 0.0033(15) |
| C21 | 0.0245(17) | 0.050(2) | 0.073(3) | 0.0038(19) | 0.0059(17) | 0.0012(15) |
| C22 | 0.0326(18) | 0.053(2) | 0.057(2) | −0.0075(18) | −0.0052(16) | −0.0012(16) |
| C23 | 0.0317(17) | 0.0407(18) | 0.0407(18) | −0.0045(14) | 0.0021(14) | −0.0004(14) |
| C24 | 0.065(2) | 0.050(2) | 0.0325(18) | −0.0027(15) | 0.0176(17) | 0.0098(17) |

TABLE 9

Hydrogen Atom Coordinates and Isotropic Atomic Displacement Parameters ($Å^2$) for Carvedilol Hydrobromide Monohydrate.

| | x/a | y/b | z/c | U |
|---|---|---|---|---|
| H2O | 0.086(3) | 0.471(3) | 0.155(4) | 0.047 |
| H2O' | 0.082(6) | 0.465(5) | −0.077(6) | 0.047 |
| H99A | −0.073(4) | 0.3802(19) | 0.201(6) | 0.064 |
| H99B | −0.060(4) | 0.490(2) | 0.205(6) | 0.065 |
| H99 | −0.1344(19) | 0.4409(13) | 0.157(3) | 0.065 |
| H1N | 0.373(2) | 0.2411(16) | −0.205(3) | 0.039(10) |
| H2NA | −0.043(2) | 0.4188(18) | 0.045(3) | 0.058(12) |
| H2NB | −0.036(2) | 0.422(2) | −0.060(4) | 0.077(14) |
| H2A | 0.3299 | 0.4112 | 0.1114 | 0.041 |
| H3A | 0.4497 | 0.3844 | 0.0850 | 0.048 |
| H4A | 0.4633 | 0.3119 | −0.0468 | 0.048 |
| H7A | 0.2616 | 0.1720 | −0.3395 | 0.048 |
| H8A | 0.1289 | 0.1632 | −0.3836 | 0.049 |
| H9A | 0.0548 | 0.2212 | −0.2906 | 0.044 |
| H10A | 0.1112 | 0.2912 | −0.1543 | 0.039 |
| H13A | 0.2180 | 0.4552 | 0.0713 | 0.036 |
| H13B | 0.1990 | 0.3994 | 0.1468 | 0.036 |
| H14 | 0.0925 | 0.4552 | −0.0281 | 0.037 |
| H14' | 0.0943 | 0.4596 | 0.1099 | 0.037 |
| H15A | 0.0642 | 0.3477 | −0.0132 | 0.035 |
| H15B | 0.0576 | 0.3585 | 0.1069 | 0.035 |
| H16A | −0.0819 | 0.3172 | 0.0400 | 0.043 |
| H16B | −0.0599 | 0.3103 | −0.0723 | 0.043 |
| H17A | −0.1625 | 0.3802 | −0.1496 | 0.046 |
| H17B | −0.1922 | 0.3165 | −0.1021 | 0.046 |
| H20A | −0.3977 | 0.4876 | 0.0466 | 0.049 |
| H21A | −0.4785 | 0.4439 | −0.1048 | 0.060 |
| H22A | −0.4306 | 0.3786 | −0.2183 | 0.060 |
| H23A | −0.2996 | 0.3553 | −0.1809 | 0.047 |
| H24A | −0.2310 | 0.5242 | 0.2397 | 0.072 |
| H24B | −0.3101 | 0.4858 | 0.2148 | 0.072 |
| H24C | −0.3002 | 0.5475 | 0.1455 | 0.072 |

TABLE 10

Site Occupation Factors that Deviate from Unity for Carvedilol Hydrobromide Monohydrate.

| Atom | sof | Atom | sof | Atom | sof |
|---|---|---|---|---|---|
| Br1 | 1 | Br2 | 1 | O1 | 1 |
| O2 | 0.65 | H2O | 0.65 | O2' | 0.35 |
| H2O' | 0.35 | O99A | 0.50 | H99A | 0.50 |
| O99B | 0.50 | H99B | 0.50 | H99 | 1 |
| H14 | 0.65 | H14' | 0.35 | | |

Example 2

Form 2

Carvedilol HBr (Dioxane Solvate)

Form 1 is slurried in dioxane between 0 and 40° C. for 2 days. The product is filtered and mildly dried.

Example 3

Form 3

Carvedilol HBr (1-pentanol Solvate)

Form 1 is slurried in 1-pentanol between 0° C. and 40° C. for 2 days. The product is filtered and mildly dried.

Example 4

Form 4

Carvedilol HBr (2-Methyl-1-Propanol Solvate)

Form 1 is slurried in 2-Methyl-1-Propanol between 0° C. and 40° C. for 2 days. The product is filtered and mildly dried.

Example 5

Form 5

Carvedilol HBr (Trifluoroethanol Solvate)

Form 1 is slurried in trifluoroethanol between 0° C. and 40° C. for 2 days. The product is filtered and mildly dried.

Example 6

Form 6

Carvedilol HBr (2-propanol Solvate)

Form 1 is slurried in 2-propanol between 0° C. and 40° C. for 2 days. The product is filtered and mildly dried.

Example 7

Form 7

Carvedilol HBr (n-propanol Solvate #1)

Carvedilol free base is dissolved in n-propanol/water (95:5), and stoichiometric hydrobromic acid is added. The solution is cooled, and crystallization ensues. The product is filtered, washed with process solvent, and dried.

Example 8

Form 8

Carvedilol HBr (n-propanol Solvate #2)

Carvedilol HBr monohydrate (Form 1) is dissolved in n-propanol at ambient temperature. The n-propanol is slowly evaporated off, giving a white solid.

Example 9

Form 9

Carvedilol HBr (Anhydrous and Solvent Free)

Carvedilol free base is dissolved in a solvent (dichloromethane, isopropyl acetate, and acetonitrile have been used) and anhydrous HBr is added (HBr in acetic acid or gaseous HBr). The solution is cooled, and crystallization ensues. The product is filtered, washed with process solvent, and dried.

Example 10

Form 10

Carvedilol HBr (Ethanol Solvate)

Carvedilol free base is dissolved in ethanol, and anhydrous HBr is added (HBr in acetic acid). The solution is cooled, and crystallization ensues. The product is filtered, washed with process solvent, and dried.

It is to be understood that the invention is not limited to the embodiments illustrated herein. The right is reserved to the illustrated embodiments and all modifications coming within the scope of the following claims.

The various references to journals, patents, and other publications which are cited herein comprise the state of the art and are incorporated herein by reference as though fully set forth.

What is claimed is:

1. A compound which is carvedilol hydrobromide monohydrate having characteristic peaks from 0° degrees 2-theta (2θ) to 35° degrees 2-theta (2θ) at about 6.5±0.2 (2θ), 10.3±0.2 (2θ), 15.7±0.2 (2θ), 16.3±0.2 (2θ), 19.8±0.2 (2θ), 20.1±0.2 (2θ), 21.9±0.2 (2θ), 25.2±0.2 (2θ), and 30.6±0.2 (2θ).

2. A compound which is carvedilol hydrobromide monohydrate having an x-ray diffraction pattern as substantially shown in FIG. 1.

3. A compound which is carvedilol hydrobromide monohydrate having an infrared spectrum, which comprises characteristic absorption bands expressed in wave numbers as substantially shown in FIG. 6.

4. A compound which is carvedilol hydrobromide monohydrate having a Raman spectrum, which comprises characteristic peaks as shown in FIG. 3.

5. A compound which is carvedilol hydrobromide dioxane solvate having characteristic peaks from 0° degrees 2-theta (2θ) to 35° degrees 2-theta (2Θ) at about 7.7±0.2 (2θ), 8.4±0.2 (2θ), 15.6±0.2 (2θ), 17.0±0.2 (2θ), 18.7±0.2 (2θ), 19.5±0.2 (2θ), 21.4±0.2 (2θ), 23.7±0.2 (2θ), and 27.9±0.2 (2θ).

6. A compound which is carvedilol hydrobromide dioxane solvate having an x-ray diffraction pattern as substantially shown in FIG. 78.

7. A compound which is carvedilol hydrobromide 1-pentanol solvate having characteristic peaks from 0° degrees 2-theta (2θ) to 35° degrees 2-theta (2θ) at about 7.5±0.2 (2θ), 7.8±0.2 (2θ), 15.2±0.2 (2θ), 18.9±0.2 (2θ), 22.1±0.2 (2θ), and 31.4±0.2 (2θ).

8. A compound which is carvedilol hydrobromide 1-pentanol solvate having an x-ray diffraction pattern as substantially shown in FIG. 79.

9. A compound which is carvedilol hydrobromide 2-methyl-1-propanol solvate having characteristic peaks from 0° degrees 2-theta (2θ) to 35° degrees 2-theta (2θ) at about 7.8±0.2 (2θ), 8.1±0.2 (2θ), 16.3±0.2 (2θ), 18.8±0.2 (2θ), 21.8±0.2 (2θ), and 28.5±0.2 (2θ).

10. A compound which is carvedilol hydrobromide 2-methyl-1-propanol solvate having an x-ray diffraction pattern as substantially shown in FIG. 80.

11. A compound which is carvedilol hydrobromide trifluoroethanol solvate having characteristic peaks from 0° degrees 2-theta (2θ) to 35° degrees 2-theta (2θ) at about 7.7±0.2 (2θ), 8.4±0.2 (2θ), 15.6±0.2 (2θ), 16.9±0.2 (2θ), 18.9±0.2 (2θ), 21.8±0.2 (2θ), 23.3±0.2 (2θ), 23.8±0.2 (2θ), and 32.7±0.2 (2θ).

12. A compound which is carvedilol hydrobromide trifluoroethanol solvate having an x-ray diffraction pattern as substantially shown in FIG. 81.

13. A compound which is carvedilol hydrobromide 2-propanol solvate having characteristic peaks from 0° degrees 2-theta (2θ) to 35° degrees 2-theta (2θ) at about 7.9±0.2 (2θ), 8.3±0.2 (2θ), 18.8±0.2 (2θ), 21.7±0.2 (2θ), 23.2±0.2 (2θ), 23.6±0.2 (2θ), and 32.1±0.2 (2θ).

14. A compound which is carvedilol hydrobromide 2-propanol solvate having an x-ray diffraction pattern as substantially shown in FIG. 82.

15. A compound which is carvedilol hydrobromide n-propanol solvate #1 having characteristic peaks from 0° degrees 2-theta (2θ) to 35° degrees 2-theta (2θ) at about 7.9±0.2 (2θ), 8.5±0.2 (2θ), 17.0±0.2 (2θ), 18.8±0.2 (2θ), 21.6±0.2 (2θ), 23.1±0.2 (2θ), 23.6±0.2 (2θ), and 21.2±0.2 (2θ).

16. A compound which is carvedilol hydrobromide n-propanol solvate #1 having an x-ray diffraction pattern as substantially shown in FIG. 46.

17. A compound which is carvedilol hydrobromide n-propanol solvate #2 having characteristic peaks from 0° degrees 2-theta (2θ) to 35° degrees 2-theta (2θ) at about 8.0±0.2 (2θ), 18.8±0.2 (2θ), 21.6±0.2 (2θ), 23.1±0.2 (2θ), 25.9±0.2 (2θ), 27.2±0.2 (2θ), 30.6±0.2 (2θ), and 32.2±0.2 (2θ).

18. A compound which is carvedilol hydrobromide n-propanol solvate #2 having an x-ray diffraction pattern as substantially shown in FIG. 54.

19. A compound which is carvedilol hydrobromide ethanol solvate having characteristic peaks from 0° degrees 2-theta (2θ) to 35° degrees 2-theta (2θ) at about 8.1±0.2 (2θ), 8.6±0.2 (2θ), 13.2±0.2 (2θ), 17.4±0.2 (2θ), 18.6±0.2 (2θ), 21.8±0.2 (2θ), 23.2±0.2 (2θ), 23.7±0.2 (2θ), and 27.4±0.2 (2θ).

20. A compound which is carvedilol hydrobromide ethanol solvate having an x-ray diffraction pattern as substantially shown in FIG. 70.

21. A compound which is carvedilol hydrobromide anhydrous having characteristic peaks from 0° degrees 2-theta (2θ) to 35° degrees 2-theta (2θ) at about 6.6±0.2 (2θ), 16.1±0.2 (2θ), 17.3±0.2 (2θ), 21.2±0.2 (2θ), 22.1±0.2 (2θ), 24.1±0.2 (2θ), and 27.9±0.2 (2θ).

22. A compound which is carvedilol hydrobromide anhydrous having an x-ray diffraction pattern as substantially shown in FIG. 62.

23. A compound which is carvedilol hydrobromide anhydrous having an infrared spectrum, which comprises characteristic absorption bands expressed in wave numbers as substantially shown in FIG. 67.

24. A compound which is carvedilol hydrobromide anhydrous having a Raman spectrum, which comprises characteristic peaks as substantially shown in FIG. 64.

25. A pharmaceutical composition, comprising the compound according to claim 1 and a pharmaceutically acceptable carrier.

26. A pharmaceutical composition, comprising the compound according to claim 21 and a pharmaceutically acceptable carrier.

27. A method of treating hypertension, congestive heart failure, or angina, which comprises administering to a subject in need thereof an effective amount of a compound according to claim 1.

28. A method of treating hypertension, congestive heart failure, or angina, which comprises administering to a subject in need thereof an effective amount of a compound according to claim 21.

29. A method of treating hypertension, congestive heart failure, or angina, which comprises administering to a subject in need thereof an effective amount of a pharmaceutical composition according to claim 25.

30. A method of treating hypertension, congestive heart failure, or angina, which comprises administering to a subject in need thereof an effective amount of a pharmaceutical composition according to claim 26.

* * * * *